(12) United States Patent
Verdine et al.

(10) Patent No.: US 8,957,026 B2
(45) Date of Patent: Feb. 17, 2015

(54) BETA-CATENIN TARGETING PEPTIDES AND USES THEREOF

(75) Inventors: Gregory L. Verdine, Boston, MA (US); Tom N. Grossmann, Dortmund (DE); Tsung-Han Johannes Yeh, Jamaica Plain, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/825,709

(22) PCT Filed: Sep. 22, 2011

(86) PCT No.: PCT/US2011/052755
§ 371 (c)(1),
(2), (4) Date: Jun. 10, 2013

(87) PCT Pub. No.: WO2012/040459
PCT Pub. Date: Mar. 29, 2012

(65) Prior Publication Data
US 2014/0005118 A1    Jan. 2, 2014

Related U.S. Application Data

(60) Provisional application No. 61/385,405, filed on Sep. 22, 2010.

(51) Int. Cl.
| | | |
|---|---|---|
| C07K 7/08 | (2006.01) | |
| C07K 14/47 | (2006.01) | |
| C07K 1/113 | (2006.01) | |
| A61K 38/00 | (2006.01) | |

(52) U.S. Cl.
CPC . *C07K 7/08* (2013.01); *C07K 14/47* (2013.01); *C07K 14/4703* (2013.01); *C07K 1/113* (2013.01); *A61K 38/00* (2013.01)
USPC ........ 514/19.3; 514/21.4; 514/21.5; 530/300; 530/326

(58) Field of Classification Search
None
See application file for complete search history.

(56) References Cited

U.S. PATENT DOCUMENTS

| | | |
|---|---|---|
| 4,270,537 A | 6/1981 | Romaine |
| 4,596,556 A | 6/1986 | Morrow et al. |
| 4,730,006 A | 3/1988 | Bohme et al. |
| 4,790,824 A | 12/1988 | Morrow et al. |
| 4,886,499 A | 12/1989 | Cirelli et al. |
| 4,940,460 A | 7/1990 | Casey et al. |
| 4,941,880 A | 7/1990 | Burns |
| 5,015,235 A | 5/1991 | Crossman |
| 5,064,413 A | 11/1991 | McKinnon et al. |
| 5,141,496 A | 8/1992 | Dalto et al. |
| 5,190,521 A | 3/1993 | Hubbard et al. |
| 5,312,335 A | 5/1994 | McKinnon et al. |
| 5,328,483 A | 7/1994 | Jacoby |
| 5,334,144 A | 8/1994 | Alchas et al. |
| 5,339,163 A | 8/1994 | Homma et al. |
| 5,364,851 A | 11/1994 | Joran |
| 5,383,851 A | 1/1995 | McKinnon et al. |
| 5,417,662 A | 5/1995 | Hjertman et al. |
| 5,446,128 A | 8/1995 | Kahn |
| 5,466,220 A | 11/1995 | Brenneman |
| 5,480,381 A | 1/1996 | Weston |
| 5,503,627 A | 4/1996 | McKinnon et al. |
| 5,520,639 A | 5/1996 | Peterson et al. |
| 5,527,288 A | 6/1996 | Gross et al. |
| 5,569,189 A | 10/1996 | Parsons |
| 5,599,302 A | 2/1997 | Lilley et al. |
| 5,622,852 A | 4/1997 | Korsmeyer |
| 5,649,912 A | 7/1997 | Peterson |
| 5,663,316 A | 9/1997 | Xudong |
| 5,704,911 A | 1/1998 | Parsons |
| 5,708,136 A | 1/1998 | Burrell et al. |
| 5,750,767 A | 5/1998 | Carpino et al. |
| 5,811,515 A | 9/1998 | Grubbs et al. |
| 5,824,483 A | 10/1998 | Houston, Jr. et al. |
| 5,834,209 A | 11/1998 | Korsmeyer |
| 5,856,445 A | 1/1999 | Korsmeyer |
| 5,874,529 A | 2/1999 | Gilon et al. |
| 5,893,397 A | 4/1999 | Peterson et al. |
| 5,922,863 A | 7/1999 | Grubbs et al. |
| 5,955,593 A | 9/1999 | Korsmeyer |
| 5,965,703 A | 10/1999 | Horne et al. |
| 5,993,412 A | 11/1999 | Deily et al. |
| 5,998,583 A | 12/1999 | Korsmeyer |
| 6,051,554 A | 4/2000 | Hornik et al. |
| 6,153,391 A | 11/2000 | Picksley et al. |

(Continued)

FOREIGN PATENT DOCUMENTS

| | | |
|---|---|---|
| WO | WO 96/34878 A1 | 11/1996 |
| WO | WO 97/13537 A1 | 4/1997 |

(Continued)

OTHER PUBLICATIONS

U.S. Appl. No. 13/680,905, filed Nov. 19, 2012, Verdine et al.
Invitation to Pay Additional Fees for PCT/US2010/001952, mailed Oct. 29, 2010.
International Search Report and Written Opinion for PCT/US2010/001952, mailed Feb. 2, 2011.
International Preliminary Report on Patentability for PCT/US2010/001952, mailed Jan. 26, 2012.
Extended European Search Report for EP 09800675.2, mailed Dec. 6, 2012.
Invitation to Pay Additional Fees for PCT/US2009/004260, mailed Mar. 19, 2010.
International Search Report and Written Opinion for PCT/US2009/004260, mailed Oct. 15, 2010.

(Continued)

*Primary Examiner* — Daniel C Gamett
(74) *Attorney, Agent, or Firm* — Wolf, Greenfield & Sacks, P.C.; C. Hunter Baker

(57) ABSTRACT

The invention relates to β-catenin targeting peptides comprising an α-helical segment that are optionally stapled or stitched, and pharmaceutical compositions thereof. Uses of the inventive β-catenin targeting polypeptides including methods for treatment of disease, such as diseases associated with aberrant Wnt signaling, including cancer, are also provided.

21 Claims, 16 Drawing Sheets

(56) References Cited

U.S. PATENT DOCUMENTS

| | | |
|---|---|---|
| 6,184,344 B1 | 2/2001 | Kent et al. |
| 6,271,198 B1 | 8/2001 | Braisted et al. |
| 6,326,354 B1 | 12/2001 | Gross et al. |
| 6,610,657 B1 | 8/2003 | Goueli |
| 6,613,874 B1 | 9/2003 | Mazur et al. |
| 6,703,382 B2 | 3/2004 | Wang et al. |
| 6,713,280 B1 | 3/2004 | Huang et al. |
| 6,849,428 B1 | 2/2005 | Evans et al. |
| 6,875,594 B2 | 4/2005 | Muir et al. |
| 7,064,193 B1 | 6/2006 | Cory et al. |
| 7,083,983 B2 | 8/2006 | Lane et al. |
| 7,084,244 B2 | 8/2006 | Gilon et al. |
| 7,183,059 B2 | 2/2007 | Verdine et al. |
| 7,192,713 B1 | 3/2007 | Verdine et al. |
| 7,202,332 B2 | 4/2007 | Arora et al. |
| 7,247,700 B2 | 7/2007 | Korsmeyer et al. |
| 7,538,190 B2 | 5/2009 | Robinson et al. |
| 7,705,118 B2 | 4/2010 | Arora et al. |
| 7,723,469 B2 | 5/2010 | Walensky et al. |
| 7,745,573 B2 | 6/2010 | Robinson et al. |
| 7,786,072 B2 | 8/2010 | Verdine et al. |
| 8,324,428 B2 | 12/2012 | Verdine et al. |
| 2004/0038901 A1 | 2/2004 | Basler et al. |
| 2004/0067503 A1 | 4/2004 | Tan et al. |
| 2004/0171809 A1 | 9/2004 | Korsmeyer et al. |
| 2005/0250680 A1 | 11/2005 | Walensky et al. |
| 2006/0008848 A1 | 1/2006 | Verdine et al. |
| 2006/0014675 A1 | 1/2006 | Arora et al. |
| 2008/0262200 A1 | 10/2008 | Nash |
| 2009/0047711 A1 | 2/2009 | Nash |
| 2009/0088553 A1 | 4/2009 | Nash |
| 2009/0149630 A1 | 6/2009 | Walensky et al. |
| 2009/0176964 A1 | 7/2009 | Walensky et al. |
| 2009/0326192 A1 | 12/2009 | Nash et al. |
| 2010/0081611 A1 | 4/2010 | Bradner et al. |
| 2010/0168388 A1 | 7/2010 | Bernal et al. |
| 2010/0184628 A1 | 7/2010 | Nash |
| 2010/0184645 A1 | 7/2010 | Verdine et al. |
| 2010/0216688 A1 | 8/2010 | Nash et al. |
| 2010/0234563 A1 | 9/2010 | Arora et al. |
| 2010/0298201 A1 | 11/2010 | Nash et al. |
| 2011/0028753 A1 | 2/2011 | Verdine et al. |
| 2011/0144303 A1 | 6/2011 | Nash et al. |
| 2011/0144306 A1 | 6/2011 | Verdine et al. |
| 2011/0223149 A1 | 9/2011 | Nash et al. |
| 2011/0263815 A1 | 10/2011 | Nash |
| 2012/0082636 A1 | 4/2012 | Walensky et al. |
| 2012/0172311 A1 | 7/2012 | Nash et al. |
| 2012/0190818 A1 | 7/2012 | Nash |
| 2012/0270800 A1 | 10/2012 | Verdine et al. |
| 2013/0005943 A1 | 1/2013 | Arora et al. |

FOREIGN PATENT DOCUMENTS

| | | |
|---|---|---|
| WO | WO 97/37705 A1 | 10/1997 |
| WO | WO 99/34850 A1 | 7/1999 |
| WO | WO 00/06187 A2 | 2/2000 |
| WO | WO 02/064790 A2 | 8/2002 |
| WO | WO 03/106491 A2 | 12/2003 |
| WO | WO 2004/041275 A1 | 5/2004 |
| WO | WO 2004/058804 A1 | 7/2004 |
| WO | WO 2005/040202 A2 | 5/2005 |
| WO | WO 2005/040202 A3 | 5/2005 |
| WO | WO 2005/044839 A2 | 5/2005 |
| WO | WO 2005/090388 A1 | 9/2005 |
| WO | WO 2005/118620 A2 | 12/2005 |
| WO | WO 2005/118620 A3 | 12/2005 |
| WO | WO 2005/118634 A2 | 12/2005 |
| WO | WO 2006/103666 A2 | 10/2006 |
| WO | WO 2007/141533 A2 | 12/2007 |
| WO | WO 2008/061192 A2 | 5/2008 |
| WO | WO 2008/095063 A1 | 8/2008 |
| WO | WO 2008/121767 A2 | 10/2008 |
| WO | WO 2010/011313 A2 | 1/2010 |
| WO | WO 2011/008260 A2 | 1/2011 |
| WO | WO 2012/040459 A2 | 3/2012 |
| WO | WO 2012/174423 A1 | 12/2012 |

OTHER PUBLICATIONS

International Preliminary Report on Patentability for PCT/US2009/004260, mailed Feb. 3, 2011.
Extended European Search Report for EP 12159110.1, mailed Jul. 20, 2012.
Extended European Search Report for EP 12159110.1, mailed Sep. 27, 2012.
International Search Report and Written Opinion for PCT/US2008/058575, mailed Nov. 17, 2008.
International Preliminary Report on Patentability for PCT/US2008/058575, mailed Oct. 8, 2009.
Invitation to Pay Additional Fees for PCT/US2011/052755, mailed Feb. 16, 2012.
International Search Report and Written Opinion for PCT/US2011/052755, mailed Apr. 25, 2012.
International Preliminary Report on Patentability for PCT/US2011/052755, mailed Apr. 4, 2013.
International Search Report and Written Opinion for PCT/US2012/042738, mailed Oct. 18, 2012.
International Search Report and Written Opinion for PCT/US2008/052580, mailed May 16, 2008.
Office Communication, mailed Apr. 22, 2013, for U.S. Appl. No. 13/055,279.
Office Communication, mailed Jan. 3, 2013, for U.S. Appl. No. 12/593,384.
Notice of Allowance, mailed May 30, 2013, for U.S. Appl. No. 12/593,384.
Office Communication, mailed Feb. 9, 2012, for U.S. Appl. No. 12/420,816.
Office Communication, mailed Feb. 17, 2011, for U.S. Appl. No. 12/796,212.
Office Communication, mailed Oct. 18, 2011, for U.S. Appl. No. 12/796,212.
Notice of Allowance, mailed Aug. 6, 2012, for U.S. Appl. No. 12/796,212.
[No Author Listed] Designing Custom Peptide. from SIGMA Genosys, p. 1. Accessed Jul. 27, 2012.
Adhikary et al., Transcriptional regulation and transformation by Myc proteins. Nat Rev Mol Cell Biol. Aug. 2005;6(8):635-45.
Agola et al., Rab GTPases as regulators of endocytosis, targets of disease and therapeutic opportunities. Clin Genet. Oct. 2011; 80(4):305-318.
Altschul et al., Basic local alignment search tool. J Mol Biol. Oct. 5, 1990;215(3):403-10.
Aman et al., cDNA cloning and characterization of the human interleukin 13 receptor alpha chain. J Biol Chem. Nov. 15, 1996;271(46):29265-70.
Andrews et al., Forming Stable Helical Peptides Using Natural and Artificial Amino Acids. Tetrahedron. 1999;55:11711-43.
Andrews et al., Kinetic analysis of the interleukin-13 receptor complex. J Biol Chem. Nov. 29, 2002;277(48):46073-8. Epub Sep. 26, 2002.
Armstrong et al., X=Y-ZH Systems as potential 1,3-dipoles. 5. Intramolecular cycloadditions of imines of a-amino acid esters. Tetrahedron. 1985;41(17):3547-58.
Attisano et al., TGFbeta and Wnt pathway cross-talk. Cancer Metastasis Rev. Jan.-Jun. 2004;23(1-2):53-61.
Babine et al., Molecular Recognition of Proteinminus signLigand Complexes: Applications to Drug Design. Chem Rev. Aug. 5, 1997;97(5):1359-1472.
Banerjee et al., Structure of a DNA glycosylase searching for lesions. Science. Feb. 24, 2006;311(5764):1153-7.
Banerjee et al., Structure of a repair enzyme interrogating undamaged DNA elucidates recognition of damaged DNA. Nature. Mar. 31, 2005;434(7033):612-8.
Bang et al., Total chemical synthesis of crambin. J Am Chem Soc. Feb. 11, 2004;126(5):1377-83.

(56) References Cited

OTHER PUBLICATIONS

Barandon et al., Reduction of infarct size and prevention of cardiac rupture in transgenic mice overexpressing FrzA. Circulation. Nov. 4, 2003;108(18):2282-9. Epub Oct. 27, 2003.
Barker et al., Mining the Wnt pathway for cancer therapeutics. Nat Rev Drug Discov. Dec. 2006;5(12):997-1014.
Beloken et al., Chiral Complexes of Ni(II), Cu(II) and Cu(I) as Reagents, Catalysts and Receptors for Asymmetric Synthesis and Chiral Recognition of Amino Acids. Pure & Appl Chem. 1992;64(12):1917-24.
Belokon et al., Improved procedures for the synthesis of (S)-2-[N-(N'-benzyl-prolyl)amino]benzophenone (BPB) and Ni(II) complexes of Schiff's bases derived from BPB and amino acids. Tetrahedron: Asymmetry. 1998;9:4249-52.
Bennett et al., Regulation of osteoblastogenesis and bone mass by Wnt10b. Proc Natl Acad Sci U S A. Mar. 1, 2005;102(9):3324-9. Epub Feb. 22, 2005.
Berendsen et al., A glimpse of the Holy Grail? Science. Oct. 23, 1998;282(5389):642-3.
Berge et al., Pharmaceutical salts. J Pharm Sci. Jan. 1977;66(1):1-19.
Bernal et al., Reactivation of the p53 tumor suppressor pathway by a stapled p53 peptide. J Am Chem Soc. Mar. 7, 2007;129(9):2456-7. Epub Feb. 7, 2007.
Biagini et al., Cross-metathesis of Unsaturated α-amino Acid Derivatives. J Chem Soc Perkin Trans. 1998;1:2485-99.
Bierzynski et al., A salt bridge stabilizes the helix formed by isolated C-peptide of Rnase A. Proc Natl Acad Sci U S A. Apr. 1982;79(8):2470-4.
Blackwell et al., Highly Efficient Synthesis of Covalently Cross-Linked Peptide Helices by Ring-Closing Metathesis. Angew Chem Int Ed. 1998;37(23):3281-84.
Blackwell et al., Ring-closing metathesis of olefinic peptides: design, synthesis, and structural characterization of macrocyclic helical peptides. J Org Chem. Aug. 10, 2001;66(16):5291-302.
Blundell et al., Atomic positions in rhombohedral 2-zinc insulin crystals. Nature. Jun. 25, 1971;231(5304):506-11.
Bode et al., Chemoselective amide ligations by decarboxylative condensations of N-alkylhydroxylamines and alpha-ketoacids. Angew Chem Int Ed Engl. Feb. 13, 2006;45(8):1248-52.
Boyden et al., High bone density due to a mutation in LDL-receptor-related protein 5. N Engl J Med. May 16, 2002 16;346(20):1513-21.
Bracken et al., Synthesis and Nuclear Magnetic Resonance Structure Determination of an α-Helical, Bicyclic, Lactam-Bridged Hexapeptide. J Am Chem Soc. 1994;116:6431-32.
Bradley et al., Limits of cooperativity in a structurally modular protein: response of the Notch ankyrin domain to analogous alanine substitutions in each repeat. J Mol Biol. Nov. 22, 2002;324(2):373-86.
Brandt et al., Dimeric fragment of the insulin receptor alpha-subunit binds insulin with full holoreceptor affinity. J Biol Chem. Apr. 13, 2001;276(15):12378-84. Epub Jan. 12, 2001.
Brubaker et al., Solution structure of the interacting domains of the Mad-Sin3 complex: implications for recruitment of a chromatin-modifying complex. Cell. Nov. 10, 2000;103(4):655-65.
Brusselle et al., Allergen-induced airway inflammation and bronchial responsiveness in wild-type and interleukin-4-deficient mice. Am J Respir Cell Mol Biol. Mar. 1995;12(3):254-9.
Burger et al., Synthesis of a-(trifluoromethy)-substituted a-amino acids. Part 7. An efficient synthesis for a-trifluoromethyl-substituted w-carboxy a-amino acids. Chemiker-Zeitung. 1990;114(3):101-04. German.
Caricasole et al., The Wnt pathway, cell-cycle activation and beta-amyloid: novel therapeutic strategies in Alzheimer's disease? Trends Pharmacol Sci. May 2003;24(5):233-8.
Carillo et al., The Multiple Sequence Alignment Problem in Biology. SIAM J Applied Math. 1988;48:1073-82.
Carlson et al., Specificity landscapes of DNA binding molecules elucidate biological function. Proc Natl Acad Sci U S A. Mar. 9, 2010;107(10):4544-9. doi: 10.1073/pnas.0914023107. Epub Feb. 22, 2010.

Chen et al., Determination of the helix and beta form of proteins in aqueous solution by circular dichroism. Biochemistry. Jul. 30, 1974;13(16):3350-9.
Chen et al., Small molecule-mediated disruption of Wnt-dependent signaling in tissue regeneration and cancer. Nat Chem Biol. Feb. 2009;5(2):100-7. Epub Jan. 4, 2009.
Cheng et al., Emerging role of RAB GTPases in cancer and human disease. Cancer Res. Apr. 1, 2005;65(7):2516-9.
Cheng et al., The RAB25 small GTPase determines aggressiveness of ovarian and breast cancers. Nat Med. Nov. 2004;10(11):1251-6. Epub Oct. 24, 2004.
Cheon et al., Beta-Catenin stabilization dysregulates mesenchymal cell proliferation, motility, and invasiveness and causes aggressive fibromatosis and hyperplastic cutaneous wounds. Proc Natl Acad Sci U S A. May 14, 2002;99(10):6973-8. Epub Apr. 30, 2002.
Chia et al., Emerging roles for Rab family GTPases in human cancer. Biochim Biophys Acta. Apr. 2009;1795(2):110-6.
Chiaramonte et al., Studies of murine schistosomiasis reveal interleukin-13 blockade as a treatment for established and progressive liver fibrosis. Hepatology. Aug. 2001;34(2):273-82.
Christodoulides et al., WNT10B mutations in human obesity. Diabetologia. Apr. 2006;49(4):678-84. Epub Feb. 14, 2006.
Clark et al., Supramolecular Design by Covalent Capture. Design of a Peptide Cylinder via Hydrogen-Bond-Promoted Intermolecular Olefin Metathesis. J Am Chem Soc. 1995;117:12364-65.
Clevers, Wnt/beta-catenin signaling in development and disease. Cell. Nov. 3, 2006;127(3):469-80.
Cohn et al., Cutting Edge: IL-4-independent induction of airway hyperresponsiveness by Th2, but not Th1, cells. J Immunol. Oct. 15, 1998;161(8):3813-6.
Cole et al., Transcription-independent functions of MYC: regulation of translation and DNA replication. Nat Rev Mol Cell Biol. Oct. 2008;9(10):810-5. Epub Aug. 13, 2008.
Cong et al., A protein knockdown strategy to study the function of beta-catenin in tumorigenesis. BMC Mol Biol. Sep. 29, 2003;4:10.
Cossu et al., Wnt signaling and the activation of myogenesis in mammals EMBO J. Dec. 15, 1999;18(24):6867-72.
Cusack et al., 2,4,6-Tri-isopropylbenzenesulphonyl Hydrazide: A Convenient Source of Di-imide. Tetrahedron. 1976;32:2157-62.
David et al., Expressed protein ligation. Method and applications. Eur J Biochem. Feb. 2004;271(4):663-77.
Dawson et al., Synthesis of proteins by native chemical ligation. Science. Nov. 4, 1994;266(5186):776-9.
De Guzman et al., Structural basis for cooperative transcription factor binding to the CBP coactivator. J Mol Biol. Feb. 3, 2006;355(5):1005-13. Epub Oct. 5, 2005.
De Meyts et al., Insulin interactions with its receptors: experimental evidence for negative cooperativity. Biochem Biophys Res Commun. Nov. 1, 1973;55(1):154-61.
De Meyts, The structural basis of insulin and insulin-like growth factor-I receptor binding and negative co-operativity, and its relevance to mitogenic versus metabolic signalling. Diabetologia. Sep. 1994;37 Suppl 2:S135-48.
Debinski et al., Retargeting interleukin 13 for radioimmunodetection and radioimmunotherapy of human high-grade gliomas. Clin Cancer Res. Oct. 1999;5(10 Suppl):3143s-3147s.
Denmark et al., Cyclopropanation with Diazomethane and Bis(oxazoline)palladium(II) Complexes. J Org Chem. May 16, 1997;62(10):3375-3389.
Devereux et al., A comprehensive set of sequence analysis programs for the VAX. Nucleic Acids Res. Jan. 11, 1984;12(1 Pt 1):387-95.
Doron et al., Probiotics: their role in the treatment and prevention of disease. Expert Rev Anti Infect Ther. 2006;4:261-75.
Eisenmesser et al., Solution structure of interleukin-13 and insights into receptor engagement. J Mol Biol. Jun. 29, 2001;310(1):231-41.
Ellis et al., Design, synthesis, and evaluation of a new generation of modular nucleophilic glycine equivalents for the efficient synthesis of sterically constrained alpha-amino acids. J Org Chem. Oct. 27, 2006;71(22):8572-8.
Erlanson et al., The leucine zipper domain controls the orientation of AP-1 in the NFAT.AP-1.DNA complex. Chem Biol. Dec. 1996;3(12):981-91.

(56) References Cited

OTHER PUBLICATIONS

Evans et al., The Rise of Azide—Alkyne 1,3-Dipolar 'Click' Cycloaddition and its Application to Polymer Science and Surface Modification. Australian Journal of Chemistry. 2007;60:384-95.
Favrin et al., Two-state folding over a weak free-energy barrier. Biophys J. Sep. 2003;85(3):1457-65.
Fischback et al., Specific biochemical inactivation of oncogenic Ras proteins by nucleoside diphosphate kinase. Cancer Res. Jul. 15, 2003;63(14):4089-94.
Fischer et al., The HIV-1 Rev activation domain is a nuclear export signal that accesses an export pathway used by specific cellular RNAs. Cell. Aug. 11, 1995;82(3):475-83.
Fisher et al., Myc/Max and other helix-loop-helix/leucine zipper proteins bend DNA toward the minor groove. Proc Natl Acad Sci U S A. Dec. 15, 1992;89(24):11779-83.
Formaggio et al., Inversion of 3(10)-helix screw sense in a (D-alpha Me)Leu homo-tetrapeptide induced by a guest D-(alpha Me)Val residue. J Pept Sci. Nov.-Dec. 1995;1(6):396-402.
Fromme et al., Structural basis for removal of adenine mispaired with 8-oxoguanine by MutY adenine DNA glycosylase. Nature. Feb. 12, 2004;427(6975):652-6.
Fuchs et al., Socializing with the neighbors: stem cells and their niche. Cell. Mar. 19, 2004;116(6):769-78.
Furstner et al., Alkyne Metathesis: Development of a Novel Molybdenum-Based Catalyst System and Its Application to the Total Synthesis of Epothilone A and C. Chem Euro J. 2001;7(24):5299-5317.
Furstner et al., Mo[N(t-Bu)(AR)]3 Complexes As Catalyst Precursors: In Situ Activation and Application to Metathesis Reactions of Alkynes and Diynes. J Am Chem Soc. 1999;121:9453-54.
Furstner et al., Nozaki—Hiyama—Kishi Reactions Catalytic in Chromium. J Am Chem Soc. 1996:118:12349-57.
Gallivan et al., A neutral, water-soluble olefin metathesis catalyst based on an N-heterocyclic carbene ligand. Tetrahedron Letters. 2005;46:2577-80.
Gante, Peptidomimetics—Tailored Enzyme Inhibitors. J Angew Chem Int Ed Engl. 1994;33:1699-1720.
Gat et al., De Novo hair follicle morphogenesis and hair tumors in mice expressing a truncated beta-catenin in skin. Cell. Nov. 25, 1998;95(5):605-14.
Gavathiotis et al., BAX activation is initiated at a novel interaction site. Nature. Oct. 23, 2008;455(7216):1076-81.
Gentle et al., Direct production of proteins with N-terminal cysteine for site-specific conjugation. Bioconjug Chem. May-Jun. 2004;15(3):658-63.
Gerber-Lemaire et al., Glycosylation pathways as drug targets for cancer: glycosidase inhibitors. Mini Rev Med Chem. Sep. 2006;6(9):1043-52.
Giannis et al., Peptidomimetics for Receptor Ligands—Discovery, Development, and Medical Perspectives. Angew Chem Int Ed Engl. 1993;32:1244-67.
Gong et al., LDL receptor-related protein 5 (LRP5) affects bone accrual and eye development. Cell. Nov. 16, 2001;107(4):513-23.
Goodson et al., Potential Growth Antagonists. I. Hydantoins and Disubstituted Glycines. J Org Chem. 1960;25:1920-24.
Görlich et al., Transport between the cell nucleus and the cytoplasm. Annu Rev Cell Dev Biol. 1999;15:607-60.
Goun et al., Molecular transporters: synthesis of oligoguanidinium transporters and their application to drug delivery and real-time imaging. Chembiochem. Oct. 2006;7(10):1497-515.
Greenfield et al., Computed circular dichroism spectra for the evaluation of protein conformation. Biochemistry. Oct. 1969;8(10):4108-16.
Greenlee et al., A General Synthesis of α-vinyl-α-amino acids. Tetrahedron Letters. 1978;42:3999-40002.
Grubbs et al., Ring-Closing Metathesis and Related Processes in Organic Synthesis. Acc Chem Res. 1995;28:446-52.
Grünig et al., Requirement for IL-13 independently of IL-4 in experimental asthma. Science. Dec. 18, 1998;282(5397):2261-3.
Guinn et al., Synthesis and characterization of polyamides containing unnatural amino acids. Biopolymers. May 1995;35(5):503-12.

Harper et al., Efficacy of a bivalent L1 virus-like particle vaccine in prevention of infection with human papillomavirus types 16 and 18 in young women: a randomized controlled trial. Lancet. Nov. 13-19, 2004;364(9447):1757-65.
Harris et al., Synthesis of proline-modified analogues of the neuroprotective agent glycyl-l-prolyl-glutamic acid (GPE). Tetrahedron. 2005;61:10018-35.
Hartmann et al., Dual roles of Wnt signaling during chondrogenesis in the chicken limb. Development. Jul. 2000;127(14):3141-59.
Hartmann, A Wnt canon orchestrating osteoblastogenesis. Trends Cell Biol. Mar. 2006;16(3):151-8. Epub Feb. 7, 2006.
Hellman et al., Electrophoretic mobility shift assay (EMSA) for detecting protein-nucleic acid interactions. Nat Protoc. 2007;2(8):1849-61.
Henchey et al., Contemporary strategies for the stabilization of peptides in the α-helical conformation. Curr Opin Chem Biol. 2008;12:692-97.
Hipfner et al., Connecting proliferation and apoptosis in development and disease. Nat Rev Mol Cell Biol. Oct. 2004;5(10):805-15.
Hoang et al., Dickkopf 3 inhibits invasion and motility of Saos-2 osteosarcoma cells by modulating the Wnt-beta-catenin pathway. Cancer Res. Apr. 15, 2004;64(8):2734-9.
Holford et al., Adding 'splice' to protein engineering. Structure. Aug. 15, 1998;6(8):951-6.
Huang et al., How insulin binds: the B-chain alpha-helix contacts the L1 beta-helix of the insulin receptor. J Mol Biol. Aug. 6, 2004;341(2):529-50.
Huang et al., Tankyrase inhibition stabilizes axin and antagonizes Wnt signalling. Nature. Oct. 1, 2009;461(7264):614-20. Epub Sep. 16, 2009.
Jackson et al., General Approach to the Synthesis of Short α-Helical Peptides. J Am Chem Soc. 1991;113:9391-92.
Jamieson et al., Granulocyte-macrophage progenitors as candidate leukemic stem cells in blast-crisis CML. N Engl J Med. Aug. 12, 2004;351(7):657-67.
Jensen et al., Activation of the insulin receptor (IR) by insulin and a synthetic peptide has different effects on gene expression in IR-transfected L6 myoblasts. Biochem J. Jun. 15, 2008;412(3):435-45. doi: 10.1042/BJ20080279.
Jordan et al., Wnt4 overexpression disrupts normal testicular vasculature and inhibits testosterone synthesis by repressing steroidogenic factor 1/beta-catenin synergy. Proc Natl Acad Sci U S A. Sep. 16, 2003;100(19):10866-71. Epub Aug. 29, 2003.
Junutula et al., Molecular characterization of Rab11 interactions with members of the family of Rab11-interacting proteins. J Biol Chem. Aug. 6, 2004;279(32):33430-7. Epub Jun. 1, 2004.
Karwoski et al., Lysinonorleucine cross-link formation in alpha amino heptenoic acid-substituted peptide derivatives. Biopolymers. 1978;17(5):1119-27.
Katoh et al., Cross-talk of WNT and FGF signaling pathways at GSK3beta to regulate beta-catenin and SNAIL signaling cascades. Cancer Biol Ther. Sep. 2006;5(9):1059-64. Epub Sep. 4, 2006.
Katsu et al., The human frizzled-3 (FZD3) gene on chromosome 8p21, a receptor gene for Wnt ligands, is associated with the susceptibility to schizophrenia. Neurosci Lett. Dec. 15, 2003;353(1):53-6.
Kaul et al., Stereochemical control of peptide folding. Bioorg Med Chem. Jan. 1999;7(1):105-17.
Kawamoto, Targeting the BCL9/B9L binding interaction with beta-catenin as a potential anticancer strategy. PhD Thesis. Jun. 3, 2010. Available at http://deepblue.lib.umich.edu/handle/2027.42/75846 last accessed Apr. 9, 2012. Abstract only. 2 pages.
Kazmaier, Sythesis of Quaternary Amino Acids Containing β, γ- as well as γ,δ-Unsaturated Side Chains via Chelate-Enolate Claisen Rearrangement. Tetrahedron Letters. 1996;37(30):5351-4.
Kelly-Welch et al., Interleukin-4 and Interleukin-13 Signaling Connections Maps. Science. 2003;300:1527-28.
Kim et al., Stereochemical effects of all-hydrocarbon tethers in i,i+4 stapled peptides. Bioorg Med Chem Lett. May 1, 2009;19(9):2533-6. Epub Mar. 13, 2009.
Kim et al., Synthesis of all-hydrocarbon stapled α-helical peptides by ring-closing olefin metathesis. Nat Protoc. Jun. 2011;6(6):761-71. doi: 10.1038/nprot.2011.324. Epub May 12, 2011.

(56) References Cited

OTHER PUBLICATIONS

Kimmerlin et al., '100 years of peptide synthesis': ligation methods for peptide and protein synthesis with applications to beta-peptide assemblies. J Pept Res. Feb. 2005;65(2):229-60.
Kinzler et al., Identification of FAP locus genes from chromosome 5q21. Science. Aug. 9, 1991;253(5020):661-5.
Kinzler et al., Lessons from hereditary colorectal cancer. Cell. Oct. 18, 1996;87(2):159-70.
Knackmuss et al., Specific inhibition of interleukin-13 activity by a recombinant human single-chain immunoglobulin domain directed against the IL-13 receptor alpha1 chain. Biol Chem. Mar. 2007;388(3):325-30.
Kohler et al., DNA specificity enhanced by sequential binding of protein monomers. Proc Natl Acad Sci U S A. Oct. 12, 1999;96(21):11735-9.
Kolb et al., Click Chemistry: Diverse Chemical Function from a Few Good Reactions. Angew Chem Int Ed Engl. Jun. 1, 2001;40(11):2004-2021.
Kondo et al., Frizzled 4 gene (FZD4) mutations in patients with familial exudative vitreoretinopathy with variable expressivity. Br J Ophthalmol. Oct. 2003;87(10):1291-5.
Korcsmáros et al., Uniformly curated signaling pathways reveal tissue-specific cross-talks and support drug target discovery. Bioinformatics. Aug. 15, 2010;26(16):2042-50. Epub Jun. 11, 2010.
Korinek et al., Depletion of epithelial stem-cell compartments in the small intestine of mice lacking Tcf-4. Nat Genet. Aug. 1998;19(4):379-83.
Kotha et al., Modification of constrained peptides by ring-closing metathesis reaction. Bioorg Med Chem Lett. Jun. 4, 2001;11(11):1421-3.
Kouzarides, Acetylation: a regulatory modification to rival phosphorylation? EMBO J. Mar. 15, 2000;19(6):1176-9.
Kozlovsky et al., GSK-3 and the neurodevelopmental hypothesis of schizophrenia. Eur Neuropsychopharmacol. Feb. 2002;12(1):13-25.
Kristensen et al., Expression and characterization of a 70-kDa fragment of the insulin receptor that binds insulin. Minimizing ligand binding domain of the insulin receptor. J Biol Chem. Jul. 10, 1998;273(28):17780-6.
Kristensen et al., Functional reconstitution of insulin receptor binding site from non-binding receptor fragments. J Biol Chem. May 24, 2002;277(21):18340-5. Epub Mar. 18, 2002.
Kurose et al., Cross-linking of a B25 azidophenylalanine insulin derivative to the carboxyl-terminal region of the alpha-subunit of the insulin receptor. Identification of a new insulin-binding domain in the insulin receptor. J Biol Chem. Nov. 18, 1994;269(46):29190-7.
Kussie et al., Structure of the MDM2 oncoprotein bound to the p53 tumor suppressor transactivation domain. Science. Nov. 8, 1996;274(5289):948-53.
Kutchukian et al., All-atom model for stabilization of alpha-helical structure in peptides by hydrocarbon staples. J Am Chem Soc. Apr. 8, 2009;131(13):4622-7.
Lacombe et al., Reduction of Olefins on Solid Support Using Diimide. Tetranderon Lett. 1998;39:6785-86.
Lammi et al., Mutations in AXIN2 cause familial tooth agenesis and predispose to colorectal cancer. Am J Hum Genet. May 2004;74(5):1043-50. Epub Mar. 23, 2004.
Laporte et al., Molecular and structural basis of cytokine receptor pleiotropy in the interleukin-4/13 system. Cell. Jan. 25, 2008;132(2):259-72.
Le Geuzennec et al., Molecular characterization of Sin3 PAH-domain interactor specificity and identification of PAH partners. Nucleic Acids Res. 2006;34(14):3929-37. Epub Aug. 12, 2006.
Le Geuzennec et al., Molecular determinants of the interaction of Mad with the PAH2 domain of mSin3. J Biol Chem. Jun. 11, 2004;279(24):25823-9. Epub Mar. 26, 2004.
Leduc et al., Helix-stabilized cyclic peptides as selective inhibitors of steroid receptor—coactivator interactions. Proc Natl Acad Sci USA. 2003;100(20):11273-78.
Liang et al., Wnt5a inhibits B cell proliferation and functions as a tumor suppressor in hematopoietic tissue. Cancer Cell. Nov. 2003;4(5):349-60.
Liskamp, Conformationally restricted amino acids and dipeptides, (non)peptidomimetics and secondary structure mimetics. Recl Travl Chim Pays-Bas. 1994;113:1-19.
Little et al., A Mutation in the LDL Receptor-Related Protein 5 Gene Results in the Autosomal Dominant High-Bone-Mass Trait. Am J Hum Genet. 2002;70:11-19.
Liu et al., Chemical Ligation Approach to Form a Peptide Bond between Unprotected Peptide Segments. Concept and Model Study. J Am Chem Soc. 1994;116(10):4149-53.
Liu et al., Targeted degradation of beta-catenin by chimeric F-box fusion proteins. Biochem Biophys Res Commun. Jan. 23, 2004;313(4):1023-9.
Lo et al., Phosphorylation by the beta-catenin/MAPK complex promotes 14-3-3-mediated nuclear export of TCF/POP-1 in signal-responsive cells in C. elegans. Cell. Apr. 2, 2004;117(1):95-106.
Logan et al., The Wnt signaling pathway in development and disease. Annu Rev Cell Dev Biol. 2004;20:781-810.
Losey et al., Crystal structure of *Staphylococcus aureus* tRNA adenosine deaminase TadA in complex with RNA. Nat Struct Mol Biol. Feb. 2006;13(2):153-9. Epub Jan. 15, 2006.
Lou et al., The first three domains of the insulin receptor differ structurally from the insulin-like growth factor 1 receptor in the regions governing ligand specificity. Proc Natl Acad Sci U S A. Aug. 15, 2006;103(33):12429-34. Epub Aug. 7, 2006.
Loughlin et al., Functional variants within the secreted frizzled-related protein 3 gene are associated with hip osteoarthritis in females. Proc Natl Acad Sci U S A. Jun. 29, 2004;101(26):9757-62. Epub Jun. 21, 2004.
Luo et al., Wnt signaling and human diseases: what are the therapeutic implications? Lab Invest. Feb. 2007;87(2):97-103. Epub Jan. 8, 2007.
Luscher et al., The basic region/helix-loop-helix/leucine zipper domain of Myc proto-oncoproteins: function and regulation. Oncogene. May 13, 1999;18(19):2955-66.
Luu et al, Wnt/beta-catenin signaling pathway as a novel cancer drug target. Curr Cancer Drug Targets. Dec. 2004;4(8):653-71.
MacMillan, Evolving strategies for protein synthesis converge on native chemical ligation. Angew Chem Int Ed Engl. Nov. 27, 2006;45(46):7668-72.
Marshall et al., Back to the future: ribonuclease A. Biopolymers. 2008;90(3):259-77.
McKern et al., Structure of the insulin receptor ectodomain reveals a folded-over conformation. Nature. Sep. 14, 2006;443(7108):218-21. Epub Sep. 6, 2006.
McNamara et al., Peptides constrained by an aliphatic linkage between two C(alpha) sites: design, synthesis, and unexpected conformational properties of an i,(i+4)-linked peptide. J Org Chem. Jun. 29, 2001;66(13):4585-94.
Menting et al., A thermodynamic study of ligand binding to the first three domains of the human insulin receptor: relationship between the receptor alpha-chain C-terminal peptide and the site 1 insulin mimetic peptides. Biochemistry. Jun. 16, 2009;48(23):5492-500. doi: 10.1021/bi900261q.
Meyers et al., Formation of mutually exclusive Rab11 complexes with members of the family of Rab11-interacting proteins regulates Rab11 endocytic targeting and function. J Biol Chem. Dec. 13, 2002;277(50):49003-10. Epub Oct. 9, 2002.
Miloux et al., Cloning of the human IL-13 alpha1 chain and reconstitution with the IL4R alpha of a functional IL-4/IL-13 receptor complex. FEBS Lett. Jan. 20, 1997;401(2-3):163-6.
Miyaoka et al., Increased expression of Wnt-1 in schizophrenic brains. Schizophr Res. Jul. 27, 1999;38(1):1-6.
Moellering et al., Direct inhibition of the NOTCH transcription factor complex. Nature. Nov. 12, 2009;462(7270):182-8.
Moon et al., WNT and beta-catenin signalling: diseases and therapies. Nat Rev Genet. Sep. 2004;5(9):689-99.
Morin, Beta-catenin signaling and cancer. Bioessays. Dec. 1999;21(12):1021-30.
Moy et al., Solution structure of human IL-13 and implication for receptor binding. J Mol Biol. Jun. 29, 2001;310(1):219-30.

(56) References Cited

OTHER PUBLICATIONS

Mudher et al., Alzheimer's disease-do tauists and baptists finally shake hands? Trends Neurosci. Jan. 2002;25(1):22-6.
Muir et al., Expressed protein ligation: a general method for protein engineering. Proc Natl Acad Sci U S A. Jun. 9, 1998;95(12):6705-10.
Muir, Semisynthesis of proteins by expressed protein ligation. Annu Rev Biochem. 2003;72:249-89. Epub Feb. 27, 2003.
Mynarcik et al., Alanine-scanning mutagenesis of a C-terminal ligand binding domain of the insulin receptor alpha subunit. J Biol Chem. 1996 Feb. 2, 1996;271(5):2439-42.
Mynarcik et al., Identification of common ligand binding determinants of the insulin and insulin-like growth factor 1 receptors. Insights into mechanisms of ligand binding. J Biol Chem. Jul. 25, 1997;272(30):18650-5.
Myung et al., The ubiquitin-proteasome pathway and proteasome inhibitors. Med Res Rev. Jul. 2001;21(4):245-73.
Nair et al., X-ray structures of Myc-Max and Mad-Max recognizing DNA. Molecular bases of regulation by proto-oncogenic transcription factors. Cell. Jan. 24, 2003;112(2):193-205.
Nakashima et al., Cross-talk between Wnt and bone morphogenetic protein 2 (BMP-2) signaling in differentiation pathway of C2C12 myoblasts. J Biol Chem. Nov. 11, 2005;280(45):37660-8. Epub Sep. 2, 2005.
Ngo et al., Computational complexity, protein structure prediction, and the levinthal paradox. In: The Protein Folding Problem and Tertiary Structure Prediction. K. Mem, Jr., et al. Eds. 1994:433-506.
Niemann et al., Homozygous WNT3 mutation causes tetra-amelia in a large consanguineous family. Am J Hum Genet. Mar. 2004;74(3):558-63. Epub Feb. 5, 2004.
Nilsson et al., Staudinger ligation: a peptide from a thioester and azide. Org Lett. Jun. 29, 2000;2(13):1939-41.
Nishisho et al., Mutations of chromosome 5q21 genes in FAP and colorectal cancer patients. Science. Aug. 9, 1991;253(5020):665-9.
Node et al., Hard Acid and Soft Nucleophile Systems. 3. Dealkylation of Esters with Aluminum Halide-Thiol and Aluminum Halide-Sulfide Stustems. J Org Chem. 1981;46:1991-93.
Okamura et al., Redundant regulation of T cell differentiation and TCRalpha gene expression by the transcription factors LEF-1 and TCF-1. Immunity. Jan. 1998;8(1):11-20.
Olson et al., Sizing up the heart: development redux in disease. Genes Dev. Aug. 15, 2003;17(16):1937-56. Epub Jul. 31, 2003.
Pakotiprapha et al., Crystal structure of *Bacillus stearothermophilus* UvrA provides insight into ATP-modulated dimerization, UvrB interaction, and DNA binding. Mol Cell. Jan. 18, 2008;29(1):122-33. Epub Dec. 27, 2007.
Perantoni, Renal development: perspectives on a Wnt-dependent process. Semin Cell Dev Biol. Aug. 2003;14(4):201-8.
Phelan et al., A General Method for Constraining Short Peptides to an α-Helical Conformation. J Am Chem Soc. 1997;119(3):455-60.
Picksley et al., Immunochemical analysis of the interaction of p53 with MDM2;—fine mapping of the MDM2 binding site on p53 using synthetic peptides. Oncogene. Sep. 1994;9(9):2523-9.
Pillutla et al., Peptides identify the critical hotspots involved in the biological activation of the insulin receptor. J Biol Chem. Jun. 21, 2002;277(25):22590-4. Epub Apr. 18, 2002.
Polakis, The oncogenic activation of beta-catenin. Curr Opin Genet Dev. Feb. 1999;9(1):15-21.
Qiu et al., Convenient, Large-Scale Asymmetric Synthesis of Enantiomerically Pure trans-Cinnamylglycine and -α-Alanine. Tetrahedron. 2000;56:2577-82.
Rawlinson et al., CRM1-mediated nuclear export of dengue virus RNA polymerase NS5 modulates interleukin-8 induction and virus production. J Biol Chem. Jun. 5, 2009;284(23):15589-97. Epub Mar. 18, 2009.
Reya et al., Wnt signalling in stem cells and cancer. Nature. Apr. 14, 2005;434(7035):843-50.
Rich et al., Synthesis of the cytostatic cyclic tetrapeptide, chlamydocin. Tetranderon Letts. 1983;24(48):5305-08.

Robitaille et al., Mutant frizzled-4 disrupts retinal angiogenesis in familial exudative vitreoretinopathy. Nat Genet. Oct. 2002;32(2):326-30. Epub Aug. 12, 2002.
Rodova et al., The polycystic kidney disease-1 promoter is a target of the beta-catenin/T-cell factor pathway. J Biol Chem. Aug. 16, 2002;277(33):29577-83. Epub Jun. 4, 2002.
Roos et al., Synthesis of α-Substituted α-Amino Acids via Cationic Intermediates. J Org Chem. 1993;58:3259-68.
Ross et al., Inhibition of adipogenesis by Wnt signaling. Science. Aug. 11, 2000;289(5481):950-3.
Rudinger, Characteristics of the amino acids as components of a peptide hormone sequence. In: Peptide Hormones. J. A. Parsons, ed. University Park Press. Jun. 1976:1-7.
Sampietro et al., Crystal structure of a beta-catenin/BCL9/Tcf4 complex. Mol Cell. Oct. 20, 2006;24(2):293-300.
Satoh et al., AXIN1 mutations in hepatocellular carcinomas, and growth suppression in cancer cells by virus-mediated transfer of AXIN1. Nat Genet. Mar. 2000;24(3):245-50.
Sattler et al., Structure of Bcl-xL-Bak peptide complex: recognition between regulators of apoptosis. Science. Feb. 14, 1997;275(5302):983-6.
Saxon et al., Cell surface engineering by a modified Staudinger reaction. Science. Mar. 17, 2000;287(5460):2007-10.
Schäffer et al., A novel high-affinity peptide antagonist to the insulin receptor. Biochem Biophys Res Commun. Nov. 14, 2008;376(2):380-3. doi: 10.1016/j.bbrc.2008.08.151. Epub Sep. 7, 2008.
Schäffer et al., Assembly of high-affinity insulin receptor agonists and antagonists from peptide building blocks. Proc Natl Acad Sci U S A. Apr. 15, 2003;100(8):4435-9. Epub Apr. 8, 2003.
Schafmeister et al., An All-Hydrocarbon Cross-Linking System for Enhancing the Helicity and Metabolic Stability of Peptides. J Am Chem Soc. 2000;122:5891-92.
Scheffzek et al., The Ras-RasGAP complex: structural basis for GTPase activation and its loss in oncogenic Ras mutants. Science. Jul. 18, 1997;277(5324):333-8.
Schinzel et al., The phosphate recognition site of *Escherichia coli* maltodextrin phosphorylase. FEBS Lett. Jul. 29, 1991;286(1-2):125-8.
Schmiedeberg et al., Reversible backbone protection enables combinatorial solid-phase ring-closing metathesis reaction (RCM) in peptides. Org Lett. Jan. 10, 2002;4(1):59-62.
Scholtz et al., The mechanism of alpha-helix formation by peptides. Annu Rev Biophys Biomol Struct. 1992;21:95-118.
Schrock et al., Tungsten(VI) Neopentylidyne Complexes. Organometallics. 1982;1:1645-51.
Seabra et al., Rab GTPases, intracellular traffic and disease. Trends Mol Med. Jan. 2002;8(1):23-30.
Shair, A closer view of an oncoprotein-tumor suppressor interaction. Chem Biol. Nov. 1997;4(11):791-4.
Shiba et al., Structural basis for Rab11-dependent membrane recruitment of a family of Rab11-interacting protein 3 (FIP3)/Arfophilin-1. Proc Natl Acad Sci U S A. Oct. 17, 2006;103(42):15416-21. Epub Oct. 9, 2006.
Si et al., CCN1/Cyr61 is regulated by the canonical Wnt signal and plays an important role in Wnt3A-induced osteoblast differentiation of mesenchymal stem cells. Mol Cell Biol. Apr. 2006;26(8):2955-64.
Siddle et al., Specificity in ligand binding and intracellular signalling by insulin and insulin-like growth factor receptors. Biochem Soc Trans. Aug. 2001;29(Pt 4):513-25.
Skinner et al., Basic helix-loop-helix transcription factor gene family phylogenetics and nomenclature. Differentiation. Jul. 2010;80(1):1-8. doi: 10.1016/j.diff.2010.02.003. Epub Mar. 10, 2010.
Smith et al., Structural resolution of a tandem hormone-binding element in the insulin receptor and its implications for design of peptide agonists. Proc Natl Acad Sci U S A. Apr. 13, 2010;107(15):6771-6. doi: 10.1073/pnas.1001813107. Epub Mar. 26, 2010.
Soucek et al., Modelling Myc inhibition as a cancer therapy. Nature. Oct. 2, 2008;455(7213):679-83. Epub Aug. 17, 2008.
Stein et al., Rab proteins and endocytic trafficking: potential targets for therapeutic intervention. Adv Drug Deliv Rev. Nov. 14, 2003;55(11):1421-37.

(56) References Cited

OTHER PUBLICATIONS

Stenmark et al., The Rab GTPase family. Genome Biol. 2001;2(5):3007.1-3007.7.
Still et al., Semianalytical Treatment of Solvation for Molecular Mechanics and Dynamics. J Am Chem Soc. 1990;112:6127-29.
Stueanaes et al., Beta-adrenoceptor stimulation potentiates insulin-stimulated PKB phosphorylation in rat cardiomyocytes via cAMP and PKA. Br J Pharmacol. May 2010;160(1):116-29. doi: 10.1111/j.1476-5381.2010.00677.x.
Su et al., Eradication of pathogenic beta-catenin by Skp1/Cullin/F box ubiquitination machinery. Proc Natl Acad Sci U S A. Oct. 28, 2003;100(22):12729-34. Epub Oct. 16, 2003.
Surinya et al., Role of insulin receptor dimerization domains in ligand binding, cooperativity, and modulation by anti-receptor antibodies. J Biol Chem. May 10, 2002;277(19):16718-25. Epub Mar. 1, 2002.
Takeda et al., Human sebaceous tumors harbor inactivating mutations in LEF1. Nat Med. Apr. 2006;12(4):395-7. Epub Mar. 26, 2006.
Tanaka, Design and synthesis of non-proteinogenic amino acids and secondary structures of their peptides. Yakugaku Zasshi. Oct. 2006:126(10):931-44. Japanese.
Thompson et al., Mutants of interleukin 13 with altered reactivity toward interleukin 13 receptors. J Biol Chem. Oct. 15, 1999;274(42):29944-50.
Tian et al., The role of the Wnt-signaling antagonist DKK1 in the development of osteolytic lesions in multiple myeloma. N Engl J Med. Dec. 25, 2003;349(26):2483-94.
Tolbert et al., New methods for proteomic research: preparation of proteins with N-terminal cysteines for labeling and conjugation. Angew Chem Int Ed Engl. Jun. 17, 2002;41(12):2171-4.
Toomes et al., Mutations in LRP5 or FZD4 underlie the common familial exudative vitreoretinopathy locus on chromosome 11q. Am J Hum Genet. Apr. 2004;74(4):721-30. Epub Mar. 11, 2004.
Tornøe et al., Peptidotriazoles on solid phase: [1,2,3]-triazoles by regiospecific copper(i)catalyzed 1,3-dipolar cycloadditions of terminal alkynes to azides. J Org Chem. May 3, 2002;67(9):3057-64.
Torrance et al., Combinatorial chemoprevention of intestinal neoplasia. Nat Med. Sep. 2000;6(9):1024-8.
Tsuji et al., Antiproliferative activity of REIC/Dkk-3 and its significant down-regulation in non-small-cell lung carcinomas. Biochem Biophys Res Commun. Nov. 23, 2001;289(1):257-63.
Uesugi et al., The alpha-helical FXXPhiPhi motif in p53: TAF interaction and discrimination by MDM2. Proc Natl Acad Sci U S A. Dec. 21, 1999;96(26):14801-6.
Vaickus et al., Immune markers in hematologic malignancies. Crit Rev Oncol Hematol. Dec. 1991;11(4):267-97.
Van Genderen et al., Development of several organs that require inductive epithelial-mesenchymal interactions is impaired in LEF-1-deficient mice. Genes Dev. Nov. 15, 1994;8(22):2691-703.
Van Gijn et al., The wnt-frizzled cascade in cardiovascular disease. Cardiovasc Res. Jul. 2002;55(1):16-24.
Varallo et al., Beta-catenin expression in Dupuytren's disease: potential role for cell-matrix interactions in modulating beta-catenin levels in vivo and in vitro. Oncogene. 2003 Jun. 12, 2003;22(24):3680-4.
Venancio et al., Reconstructing the ubiquitin network: cross-talk with other systems and identification of novel functions. Genome Biol. 2009;10(3):R33. Epub Mar. 30, 2009.
Verdine et al., The challenge of drugging undruggable targets in cancer: lessons learned from targeting BCL-2 family members. Clin Cancer Res. Dec. 15, 2007;13(24):7264-70.
Verma et al., Small interfering RNAs directed against beta-catenin inhibit the in vitro and in vivo growth of colon cancer cells. Clin Cancer Res. Apr. 2003;9(4):1291-300.
Voet et al., Biochemistry. Second Edition. John Wiley & Sons, Inc. 1995:235-241.
Walensky et al., A stapled BID BH3 helix directly binds and activates BAX. Mol Cell. Oct. 20, 2006;24(2):199-210.
Walensky et al., Activation of apoptosis in vivo by a hydrocarbon-stapled BH3 helix. Science. Sep. 3, 2004;305(5689):1466-70.
Walter et al., Critical role for IL-13 in the development of allergen-induced airway hyperreactivity. J Immunol. Oct. 15, 2001;167(8):4668-75.
Wang et al., Inhibition of p53 degradation by Mdm2 acetylation. FEBS Lett. Mar. 12, 2004;561(1-3):195-201.
Wang, 4-Alkyl-2-trichloromethyloxazolidin-5-ones: Valuable Precursors to Enantiomerically Pure C- and N-Protected α-Alkyl Prolines. Synlett. 1999;1:33-36.
Wei et al., Disorder and structure in the Rab11 binding domain of Rab11 family interacting protein 2. Biochemistry. Jan. 27, 2009;48(3):549-57. doi: 10.1021/bi8020197.
Wilen et al., Strategies in Optical Resolution. Tetrahedron. 1977;33:2725-36.
Wilen, Tables of Resolving Agents and Optical Resolutions. E.L. Eliel, ed. Universtify of Notre Dame Press, Notre Dame, IN. 1972:268-98.
Williams et al., Asymmetric Synthesis of Monosubstituted and α,α-Disubstituted α-Amino Acids via Diastereoselective Glycine Enolate Alkylations. J Am Chem Soc. 1991;113:9276-86.
Wills-Karp et al., Interleukin-13: central mediator of allergic asthma. Science. Dec. 18, 1998;282(5397):2258-61.
Wills-Karp, Interleukin-13 in asthma pathogenesis. Immunol Rev. Dec. 2004;202:175-90.
Wills-Karp, The gene encoding interleukin-13: a susceptibility locus for asthma and related traits. Respir Res. 2000;1(1):19-23. Epub Jul. 17, 2000.
Wilson et al., The FIP3-Rab11 protein complex regulates recycling endosome targeting to the cleavage furrow during late cytokinesis. Mol Biol Cell. Feb. 2005;16(2):849-60. Epub Dec. 15, 2004.
Xi et al., Use of DNA and peptide nucleic acid molecular beacons for detection and quantification of rRNA in solution and in whole cells. Appl Environ Microbiol. Sep. 2003;69(9):5673-8.
Xing et al., Crystal structure of a beta-catenin/axin complex suggests a mechanism for the beta-catenin destruction complex. Genes Dev. Nov. 15, 2003;17(22):2753-64. Epub Nov. 4, 2003.
Yang et al., Synthesis and helical structure of lactam bridged BH3 peptides derived from pro-apoptotic Bcl-2 family proteins. Bioorg Med Chem Lett. 2004;14:1403-06.
Yang et al., Therapeutic dosing with anti-interleukin-13 monoclonal antibody inhibits asthma progression in mice. J Pharmacol Exp Ther. Apr. 2005;313(1):8-15. Epub Jan. 11, 2005.
Yu et al., The role of Axin2 in calvarial morphogenesis and craniosynostosis. Development. Apr. 2005;132(8): 1995-2005.
Zhou et al., Identification of Ubiquitin Target Proteins Using Cell-Based Arrays. J Proteome Res. 2007;6:4397-4406.
Zhou et al., Lymphoid enhancer factor 1 directs hair follicle patterning and epithelial cell fate. Genes Dev. Mar. 15, 1995;9(6):700-13.
Zhou et al., Tyrosine kinase inhibitor STI-571/Gleevec down-regulates the beta-catenin signaling activity. Cancer Lett. Apr. 25, 2003;193(2):161-70.
Zimm et al., Theory of the Phase Transition between Helix and Random Coil in Polypeptide Chains. J Chem Phys. 1959;31:526-35.
Zor et al., Solution structure of the KIX domain of CBP bound to the transactivation domain of c-Myb. J Mol Biol. Mar. 26, 2004;337(3):521-34.

TCF4* (NP_110383: 16-50): (SEQ ID NO:59)
  FITC-βAla D E L I S F K D E G E Q E βAla βAla E R D L A D V K S S L V N-NH$_2$
Axin (NP_077381: 469-483): (SEQ ID NO:60)
  FITC-βAla E N P E S I L D E H V Q R V M-NH$_2$ ax-WT (SEQ ID NO:60)
  FITC-βAla E N P E [S] I L D [E] H V [Q R] V M-NH$_2$

STAX-1 (SEQ ID NO:61)
  FITC-βAla E N P E R$^8$ I L D E H V S$^5$ R V M-NH$_2$

STAX-2 (SEQ ID NO:62)
  FITC-βAla E N P E S I L D S$^5$ H V Q S$^5$ V M-NH$_2$

STAX-3 (SEQ ID NO:63)
  FITC-βAla E N P E S$^5$ I L D S$^5$ H V Q R V M-NH$_2$ phage library (4.5 million):

XXXX SILD EHVQ RVMR
XXPE XXLD EHVQ RVMR
XXPE SIXX EHVQ RVMR
XXPE SILD XXVQ RVMR
XXPE SILD EHXX RVMR
XXPE SILD EHVQ XXMR
XXPE SILD EHVQ RVXX
ENXX XXLD EHVQ RVMR
ENXX SIXX EHVQ RVMR
ENXX SILD XXVQ RVMR
ENXX SILD EHXX RVMR
ENXX SILD EHVQ XXMR
ENXX SILD EHVQ RVXX
ENPE XXXX EHVQ RVMR
ENPE XXLD XXVQ RVMR
ENPE XXLD EHXX RVMR
ENPE XXLD EHVQ XXMR
ENPE XXLD EHVQ RVXX
ENPE SIXX XXVQ RVMR
ENPE SIXX EHXX RVMR
ENPE SIXX EHVQ XXMR
ENPE SIXX EHVQ RVXX
ENPE SILD XXXX RVMR
ENPE SILD XXVQ XXMR
ENPE SILD XXVQ RVXX
ENPE SILD EHXX XXMR
ENPE SILD EHXX RVXX
ENPE SILD EHVQ XXXX

Fig. 6A results:

1 RWPE SILD EHWE RVMR (SEQ ID NO:28)
2 VSPE SILD EHVQ RVWG (SEQ ID NO:29)
3 EWPE SILD EHWH RVMR (SEQ ID NO:30)
4 RLPE SILD EHVQ RVWP (SEQ ID NO:31)
5 ENLQ SILD EHVQ RWMR (SEQ ID NO:32)
6 ENPE SILD EHFD KWMR (SEQ ID NO:33)
9 ENPE SILD QHWV RWMR (SEQ ID NO:34)
10 ENSW SILD EHVQ RVWG (SEQ ID NO:35)
11 RYPE SILD EHVQ RWMR (SEQ ID NO:36)
12 QKPE SILD EHVQ RVWP (SEQ ID NO:37)
13 TWPE SILD EHWE RVMR (SEQ ID NO:38)
14 ENWQ SILD EHMQ RVFR (SEQ ID NO:39)
15 RLPE SILD EHVQ RWMR (SEQ ID NO:40)
16 QVPE SILD EHVQ RVWG (SEQ ID NO:41)
17 ENPE SILD EHVQ RWMR (SEQ ID NO:42)
18 ENPE SILD EHVQ RWMR (SEQ ID NO:43)
19 ENSQ SILD EHVQ RVWG (SEQ ID NO:44)
20 ENWQ SILD EHVQ RVWR (SEQ ID NO:45)
21 RYPE SILD EHVQ RWMR (SEQ ID NO:46)
22 KNPE SILD EHVQ RWMR (SEQ ID NO:47)
23 ENPE SILD EHWE RVMR (SEQ ID NO:48)
24 ENAQ SILD EHVQ RWMR (SEQ ID NO:49)
25 ENPE SILD EHMQ RVFE (SEQ ID NO:50)
26 ENSE SILD EHVQ RVWG (SEQ ID NO:51)
27 ENPE SILD EHLQ RVWQ (SEQ ID NO:52)
28 ENFQ SILD EHVQ RWMR (SEQ ID NO:53)
29 RLPE SILD EHVQ RVWR (SEQ ID NO:54)
30 WYPE SILD EHLL RVMR (SEQ ID NO:55)
31 ENPE SILD EHIL RVEK (SEQ ID NO:56)
32 WVPE SILD EHVQ RVWG (SEQ ID NO:57)
33 LQPE SILD EHVQ RVWH (SEQ ID NO:58)

Fig. 6B axin-WT (SEQ ID NO:1)
FITC-βAla  E N P E S I L D E H V Q R V M R -NH$_2$ phage-01 (SEQ ID NO:28)
FITC-βAla  [R W] P E S I L D E H [W E] R V M R -NH$_2$ phage-04 (SEQ ID NO:31)
FITC-βAla  [R L] P E S I L D E H V Q R V [W P] -NH$_2$ phage-17/18 (SEQ ID NO:42; SEQ ID NO:43)
FITC-βAla  E N P E S I L D E H V Q R V [W] R -NH$_2$

| | | | $K_d$ | charge at ph 7.5 |
|---|---|---|---|---|
| ax-WT | FITC-βAla | E N P E S I L D E H V Q R V M -NH₂ | ~5 μM | -4.0 |
| STAX-3 | FITC-βAla | E N P E S⁵ I L D S⁵ H V Q R V M -NH₂ | 60.3±6.2 nM | -3.0 |
| STAX-058 | FITC-βAla | P E S⁵ I L D S⁵ H V Q R V M -NH₂ | 69.5±7.3 nM | -2.0 |
| STAX-071 | FITC-PEG₁ | P E S⁵ I L D S⁵ H V R R V M R-NH₂ | 82.4±6.8 nM | 0.1 |
| STAX-081 | FITC-PEG₁ | P Q S⁵ I L D S⁵ H V R R V M R-NH₂ | 132±12 nM | 1.1 |
| STAX-083 | FITC-PEG₁ | P Q S⁵ I L D S⁵ H V R R W M R-NH₂ | 11.7±1.1 nM | 1.1 |
| STAX-082 | FITC-PEG₁ | P Q S⁵ I L D S⁵ H V R R V W R-NH₂ | 15.8±1.5 nM | 1.1 |
| STAX-090 | FITC-PEG₁ | R W P Q S⁵ I L D S⁵ H V R R V W R-NH₂ | 7.5±1.1 nM | 2.1 |
| STAX-147 | FITC-PEG₁ | R R W P Q S⁵ I L D S⁵ H V R R V W R-NH₂ | 12.7±2.1 nM | 3.1 |
| STAX-148 | FITC-PEG₁ | R W P R S⁵ I L D S⁵ H V R R V W R-NH₂ | 62.5±11.5 nM | 3.1 |
| STAX-149 | FITC-PEG₁ | R R W P R S⁵ I L D S⁵ H V R R V W R-NH₂ | 53.3±8.9 nM | 4.1 |
| STAX-150 | FITC-PEG₁ | R W P Q S⁵ I L D S⁵ H V R R W Nle R-NH₂ | 13.2±2.7 nM | 2.1 |
| STAX-151 | FITC-PEG₁ | R W P R S⁵ I L D S⁵ H V R R W Nle R-NH₂ | 70.1±15.8 nM | 3.1 |
| STAX-152 | FITC-PEG₁ | R W P Q S⁵ I L D S⁵ H V R R R W R-NH₂ | 55.2±23.2 nM | 3.1 |
| STAX-153 | FITC-PEG₁ | R W P R S⁵ I L D S⁵ H V R R R W R-NH₂ | 384±117 nM | 4.1 |

Fig. 9A

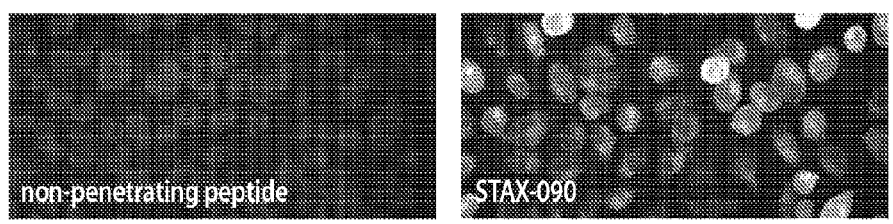

Fig. 9B

|   |   |   | $K_d$ | charge at ph 7.5 |
|---|---|---|---|---|
| STAX-083 | FITC-PEG$_1$ | P Q S⁵ I L D S⁵ H V R R W M R-NH$_2$ | 11.7±1.1 nM | 1.1 |
| STAX-082 | FITC-PEG$_1$ | P Q S⁵ I L D S⁵ H V R R V W R-NH$_2$ | 15.8±1.5 nM | 1.1 |
| STAX-090 | FITC-PEG$_1$ | R W P Q S⁵ I L D S⁵ H V R R V W R-NH$_2$ | 7.5±1.1 nM | 2.1 |
| STAX-147 | FITC-PEG$_1$ | R R W P Q S⁵ I L D S⁵ H V R R V W R-NH$_2$ | 12.7±2.1 nM | 3.1 |
| STAX-160 | FITC-PEG$_1$ | R R W P R S⁵ I L H S⁵ D V R R V A R-NH$_2$ | ~9 μM | 3.1 |
Fig. 10A
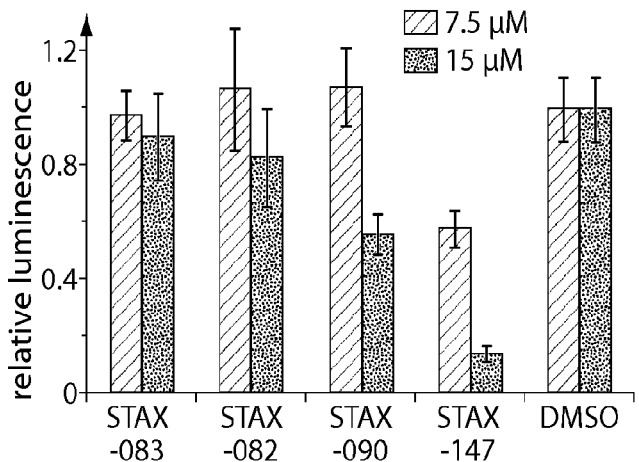
Fig. 10B
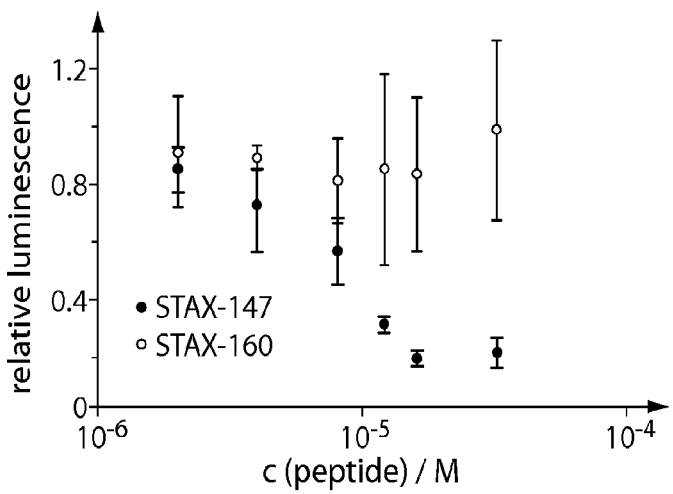
Fig. 10C

| | | | $K_d$ (of FITC analog): |
|---|---|---|---|
| STAX-147 | Biotin-PEG₁ | R R W P Q S⁵I L D S⁵H V R R V W R-NH₂ | (13 nM) |
| STAX-159 | Biotin-PEG₁ | R R W P Q S⁵I L [H] S⁵[D] V R R V W R-NH₂ | (~4 μM) |
| STAX-160 | Biotin-PEG₁ | R R W P Q S⁵I L [H] S⁵[D] V R R V [A] R-NH₂ | (~9 μM) |
| STAX-161 | Biotin-PEG₁ | R R [A] P Q S⁵I L [H] S⁵[D] V R R V [A] R-NH₂ | (>10 μM) |

STAX-159 = SEQ ID NO:64
STAX-160 = SEQ ID NO:65
STAX-161 = SEQ ID NO:66

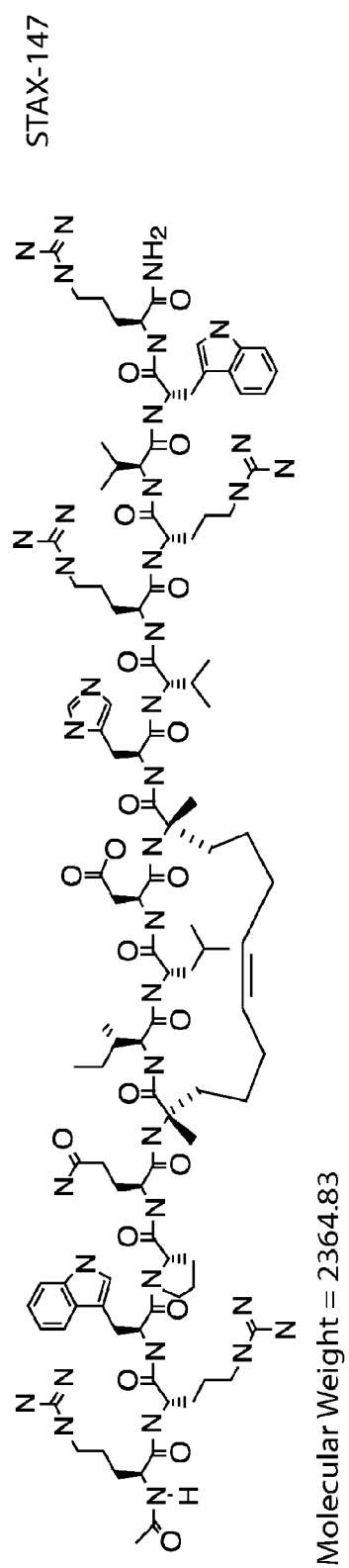
STAX-147
Molecular Weight = 2364.83
Exact Mass = 2362
Molecular Formula = C110H174N38O21
Molecular Composition = C 55.87% H 7.42% N 22.51% O 14.21%
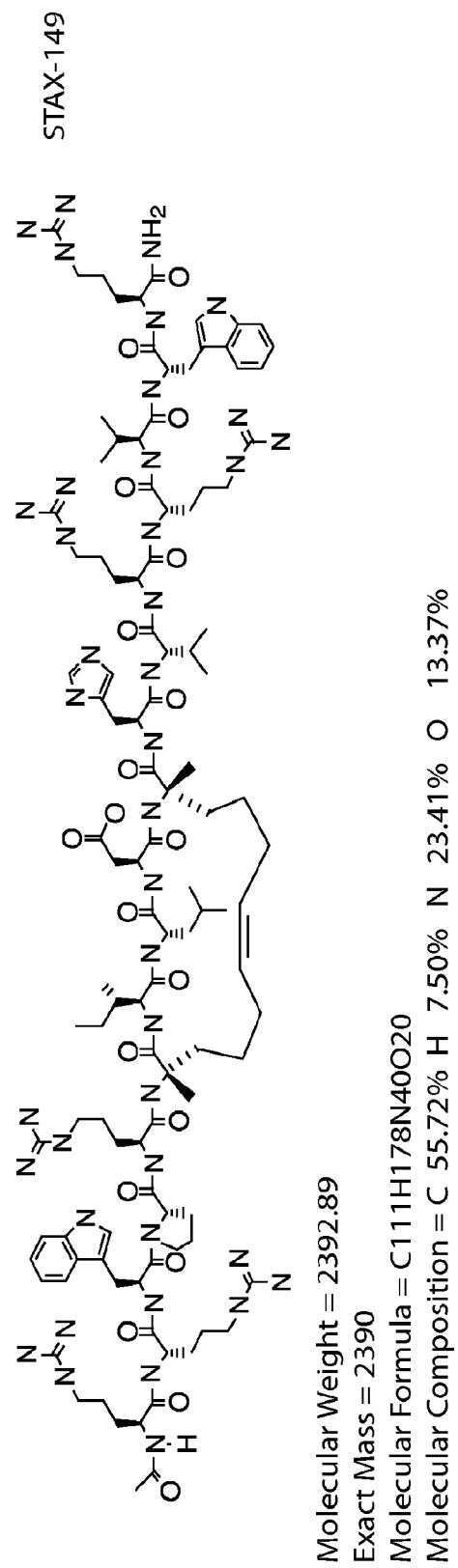
STAX-149
Molecular Weight = 2392.89
Exact Mass = 2390
Molecular Formula = C111H178N40O20
Molecular Composition = C 55.72% H 7.50% N 23.41% O 13.37%
Fig. 14

BETA-CATENIN TARGETING PEPTIDES AND USES THEREOF

RELATED APPLICATIONS

The present application is a national stage filing under 35 U.S.C. §371 of international PCT application, PCT/US2011/052755, filed Sep. 22, 2011, which claims priority under 35 U.S.C. §119(e) to U.S. provisional patent application, U.S. Ser. No. 61/385,405, filed Sep. 22, 2010, which is incorporated herein by reference.

BACKGROUND OF THE INVENTION

The WNT (Wingless and INT-1) signal transduction cascade is mediated by Wnt proteins and is involved in cell survival and proliferation as well as cell fate and movement. [1, 2] In the absence of Wnt proteins the transcriptional regulator β-catenin is recruited into a destruction complex that contains Adenomatous Polyposis Coli (APC) and Axin (FIG. 1a). This event facilitates the phosphorylation of β-catenin by casein kinase 1 (CK1) and glycogen synthase kinase-3β (GSK-3) leading to ubiquitination and proteasomal degradation of β-catenin. Therefore, in the inactive state, cells maintain low levels of β-catenin. In the nucleus, target genes of the pathway are kept in a repressed state by interacting with T-cell factors (TCF) in association with co-repressors such as Groucho. The activation of signaling is facilitated by segregation of Wnt proteins which act on target cells by binding to the Frizzeld (Fz)/low density lipoprotein related receptor (LRP) complex at the cell surface (FIG. 1b). The formation of the receptor complex involves the binding of Dishevelled (Dsh) and Axin. This inhibits the formation of the destruction complex and allows accumulation of β-catenin in the cytosol and nucleus where it interacts with DNA-bound TCF to activate the transcription of target genes.

SUMMARY OF THE INVENTION

Wnt-dependent signaling is involved in embryonic development as well as tissue self-renewal, and its deregulation is associated with several forms of cancer. The carcinogenic activation of Wnt signaling is commonly triggered by a reduced ability of a cell to degrade β-catenin. Restoring this ability would impact cancers that depend on deregulated Wnt signaling to grow. The manipulation of requisite protein-protein interactions is one approach to interfere with the pathway, using an isolated peptide of a protein to antagonize such interactions. A peptide's bioactive conformation, combining structural elements such as alpha-helices, beta-sheets, turns, and/or loops, is important as it allows for selective biological recognition of receptors, enzymes, and nucleic acids, thereby influencing cell-cell communication and/or controlling vital cellular functions, such as metabolism, immune defense, and cell division (Babine et al., Chem. Rev. (1997) 97:1359). Small peptides usually exhibit little or no secondary structure when excised from the stabilizing protein context thereby becoming subjected to rapid degradation by proteases under physiological conditions, displaying poor cell permeability, and exhibiting a lack of binding affinity and/or specificity resulting from conformational flexibility. The alpha-helix, for example, is one of the major structural components of peptides that has a propensity for unraveling and forming random coils, which are, in most cases, biologically less active, or even inactive, and are highly susceptible to proteolytic degradation.

"Peptide stapling" is a term coined for a synthetic methodology used to covalently join two olefin-containing side chains present in a polypeptide chain using an olefin metathesis reaction (J. Org. Chem. (2001) 66(16); Blackwell et al., Angew. Chem. Int. Ed. (1998) 37:3281). Stapling of a peptide using a hydrocarbon cross-linker created from an olefin metathesis reaction has been shown to help maintain a peptide's native conformation, particularly under physiological conditions (U.S. Pat. Nos. 7,192,713; 7,723,469; 7,786,072; U.S. Patent Application Publication Nos: 2010-0184645; 2010-0168388; 2010-0081611; 2009-0176964; 2009-0149630; 2006-0008848; PCT Application Publication Nos: WO 2010/011313; WO 2008/121767; WO 2008/095063; WO 2008/061192; WO 2005/044839; Schafmeister et al., J. Am. Chem. Soc. (2000) 122:5891-5892; Walensky et al., Science (2004) 305:1466-1470; each of which is incorporated herein by reference in their entirety). The stapled peptide strategy in which an all-hydrocarbon cross-link is generated by olefin metathesis is an efficient approach to increase the helical character of peptides to target α-helical binding motifs. Unlike their unstapled analogues these hydrocarbon-stapled peptides have shown to be α-helical, protease-resistant, and cell permeable.

Provided herein are peptides that target β-catenin. In certain embodiments, these peptides are stapled α-helical peptides, but the inventive peptides also include peptides that do not comprise peptide staple(s). In certain embodiments, the peptides that target β-catenin comprise portions of increased helicity generated through means other than stapling, such as lactam and disulfide cross-links as well as α-methylation, N-caps, and hydrogen bond surrogates (Henchey et al., Chem. Biol. (2008), 12: 692-7). Hydrocarbon-stapled α-helical peptides [7, 8] are suitable for targeting helical interaction motifs [8-13], and they have proven capable of antagonizing intracellular protein protein-interactions [10-13]. In certain embodiments, these peptides may be used to restore the ability of cells to degrade β-catenin, e.g. in cells that have lost their ability to degrade β-catenin. Such cells include cancer cells exhibiting, for example, inactivation of the destruction complex or loss of β-catenin phosphorylation sites [2, 3]. So far, the most downstream acting compounds capable of antagonizing deregulated Wnt signaling inhibit Tankyrase thereby stabilizing Axin and supporting the formation of the destruction complex [4, 5].

In certain embodiments, the peptides provided herein that target β-catenin comprise sequences that are approximately 5, 6, 7, 8, 9, 10, 11, 12, 13, 14, 15, 16, 17, 18, 19, 20, 21, 22, 23, 24, 25, 26, 27, 28, 29, or 30 amino acids long. In other embodiments, the peptides are approximately 5-10, 5-20, 5-30, 5-40, 5-50, 5-60, 5-70, 5-80, 5-90, or 5-100 amino acids long. In yet other embodiments, the peptides are approximately 100, 150, 200, 250, 300, 350, 400, 450, or 500 amino acids long. In certain embodiments, the peptides provided herein that target β-catenin comprise sequences that are derived from an α-helical segment of Axin that binds to β-catenin. In certain embodiments, the peptides are used to antagonize the protein-protein interaction between the transcription factor TCF and the transcriptional regulator β-catenin. In certain embodiments, the peptides are used to antagonize the protein-protein interaction between Axin and β-catenin.

In certain embodiments, the peptides comprise non-natural amino acids containing olefin-bearing tethers (FIG. 3a) to generate an all-hydrocarbon staple by olefin metathesis thereby increasing the helical character of the peptide (FIG. 3b). This strategy has been described previously, for example in U.S. Patent Application Publication Nos. 2005-02506890 and 2006-0008848. In certain embodiments, the peptides comprise peptide staples to stabilize bioactive α-helical conformation.

In certain embodiments, the β-catenin binding peptide comprises an α-helical segment, wherein the polypeptide comprises the amino acid sequence:

$X_1X_2X_3X_4X_5Y_1X_6X_7X_8Y_2X_9X_{10}X_{11}X_{12}X_{13}X_{14}X_{15}$, wherein $X_1$ is selected from the group consisting of R, K and no amino acid;
$X_2$ is selected from the group consisting of R, K, W and no amino acid;
$X_3$ is selected from the group consisting of W, Y and Q;
$X_4$ is selected from the group consisting of P, S, W, A, F and L;
$X_5$ is selected from the group consisting of E, Q, R and W;
$X_6$ is selected from the group consisting of I and L;
$X_7$ is selected from the group consisting of I and L;
$X_8$ is selected from the group consisting of D and N;
$X_9$ is selected from the group consisting of H and W;
$X_{10}$ is selected from the group consisting of V, W, L, M, F, and I;
$X_{11}$ is selected from the group consisting of Q, E, L, D, H, R, S, and V;
$X_{12}$ is selected from the group consisting of R, S, and K;
$X_{13}$ is selected from the group consisting of V, I, L, W, F and H;
$X_{14}$ is selected from the group consisting of M, norleucine, I, L, W, F and H;
$X_{15}$ is selected from the group consisting of R, G, P, E, H, K, Q, and no amino acid; and
$Y_1$ is selected from the group S, $S^5$, $R^5$, and $Y_2$ is selected from the group E, $S^5$, and $R^5$.

In certain embodiments, the peptide comprises the amino acid sequence:

$X_1X_2X_3X_4X_5Y_1X_6X_7X_8Y_2X_9X_{10}X_{11}X_{12}X_{13}X_{14}X_{15}$, wherein the amino acid of $X_{1, 2, 11, 12, 15}$ is a positively charged amino acid and/or the amino acid of $X_{3, 4, 5, 6, 7, 9, 10, 13, 14}$ is a bulky, hydrophobic amino acid.

In certain embodiments, the β-catenin binding peptide comprises an α-helical segment, wherein the polypeptide comprises the amino acid sequence:

$X_1X_2X_3XL_fX_5X_6X_7X_8X_9X_{10}X_{11}X_{12}X_{13}X_{14}X_{15}X_{16}$, wherein $X_1$ is selected from the group consisting of R, V, E, Q, T, K, W, and L;
$X_2$ is selected from the group consisting of W, S, L, N, Y, K, V, and Q:
$X_3$ is selected from the group consisting of P, L, S, W, A, and F;
$X_4$ is selected from the group consisting of E, Q, and W;
$X_5$ is S;
$X_6$ is I;
$X_7$ is L;
$X_8$ is D;
$X_9$ is selected from the group consisting of E and Q;
$X_{10}$ is H;
$X_{11}$ is selected from the group consisting of W, V, F, M, L, and I;
$X_{12}$ is selected from the group consisting of E, Q, H, D, V, and L;
$X_{13}$ is selected from the group consisting of R and K;
$X_{14}$ is selected from the group consisting of V and W;
$X_{15}$ is selected from the group consisting of M, W, F, and E; and
$X_{16}$ is selected from the group consisting of R, G, P, E, and Q, with the proviso that the sequence is not the wild-type sequence from Axin, ENPESILDEHVQRVMR (SEQ ID NO: 1) (amino acids 469-484 of rat axin) or ENPESILDEHVQRVLR (SEQ ID NO: 2) (amino acids 465-480 of human axin).

In certain embodiments, the peptides of the amino acid sequence, $X_1X_2X_3X_4X_5X_6X_7X_8X_9X_{10}X_{11}X_{12}X_{13}X_{14}X_{15}X_{16}$, are modified to induce and/or stabilize an α-helical conformation. In certain embodiments, the modification is a peptide staple, a lactam cross-link, a disulfide cross-link, α-methylation, N-caps, or a hydrogen bond surrogate. In certain embodiments, the peptides are selected from the group consisting of the amino acid sequences as set forth in FIG. 6b.

In certain embodiments, the peptides are modified to render the peptides cell permeable. Cell permeability of an inventive peptide may be increased, for example by a) introducing one or more amino acid substitutions introducing an additional R, Q, or W residue, and/or b) adding one or more additional R, Q, or W residues at the N- and/or C-terminus of the polypeptide. The inventive β-catenin targeting peptides may be modified further, for example by acetylation of the N-terminus, addition of a linker molecule (such as (β-Ala or $PEG_1$), a labeling moiety (e.g. FITC), an affinity tag (such as biotin, FLAG, 6×His, or myc), and/or a targeting moiety (e.g. integrin, antibody, or antibody fragment).

In certain embodiments, the peptides comprise an amino acid sequence selected form the group consisting of the sequences: ENPES⁵ILDS⁵HVQRVM (SEQ ID NO:14), PES⁵ILDS⁵HVQRVM (SEQ ID NO:15), PES⁵ILDS⁵HVRRVMR (SEQ ID NO:16), PQS⁵ILDS⁵HVRRVMR (SEQ ID NO:17), PQS⁵ILDS⁵HVRRWMR (SEQ ID NO:18), PQS⁵ILDS⁵HVRRVWR (SEQ ID NO:19), RWPQS⁵ILDS⁵HVRRVWR (SEQ ID NO:20), RRWPQS⁵ILDS⁵HVRRVWR (SEQ ID NO:21), RWPRS⁵ILDS⁵HVRRVWR (SEQ ID NO:22), RRWPRS⁵ILDS⁵HVRRVWR (SEQ ID NO:23), RWPQS⁵ILDS⁵HVRRWNleR (SEQ ID NO:24), RWPRS⁵ILDS⁵HVRRWNleR (SEQ ID NO:25), RWPQS⁵ILDS⁵HVRRRWR (SEQ ID NO:26), RWPRS⁵ILDS⁵HVRRRWR (SEQ ID NO:27).

Further provided herein are pharmaceutical compositions comprising the inventive β-catenin targeting polypeptide optionally comprising a pharmaceutically acceptable excipient.

Further provided herein are in vivo and in vitro methods of modulating Wnt-mediated transcription, wherein the method include contacting a cell in vivo or in vitro with a β-catenin targeting polypeptide. In certain embodiments, these methods may be used to inhibit Wnt-mediated transcription, for example in cell that exhibit aberrant expression of genes that that are activated by the Wnt-signaling pathway. In certain embodiments, these methods may be used to specifically disrupt the interaction between β-catenin and TCF (e.g., TCF4) thereby down-regulating β-catenin mediated transcriptional activation of Wnt-signaling pathway target genes. Such methods may also be used to inhibit cell proliferation that is dependent on aberrant Wnt-signaling. In certain embodiments, these methods are used to inhibit cell proliferation of cancer cells that exhibit aberrant expression of genes that that are activated by the Wnt-signaling pathway and/or elevated β-catenin protein levels.

Further provided herein are methods of treating a cancer that exhibits Wnt-signaling dependent growth in a subject. These methods include administering to a subject a pharmaceutical composition comprising a β-catenin targeting peptide as described herein in an amount sufficient to treat the cancer. In certain embodiments, diseases that are not cancer are treated by administering to a subject a pharmaceutical composition comprising a β-catenin targeting peptide as described herein in an amount sufficient to treat the disease.

Further provided herein are β-catenin targeting polypeptides or pharmaceutical composition comprising β-catenin targeting polypeptides for use in treatment of a cancer that exhibits Wnt-signaling dependent growth in a subject or for treatment of a disease that is not cancer.

This application refers to various issued patents, published patent applications, journal articles, and other publications, all of which are incorporated herein by reference.

Definitions

Definitions of specific functional groups and chemical terms are described in more detail below. For purposes of this invention, the chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; Carruthers, *Some Modern Methods of Organic Synthesis*, 3$^{rd}$ Edition, Cambridge University Press, Cambridge, 1987.

"Stapling" or "hydrocarbon-stapling," as used herein, introduces into a peptide at least two moieties capable of undergoing reaction to promote carbon-carbon bond formation that can be contacted with a reagent to generate at least one cross-linker between the at least two moieties. Stapling provides a constraint on a secondary structure, such as an alpha helix structure. The length and geometry of the cross-linker can be optimized to improve the yield of the desired secondary structure content. The constraint provided can, for example, prevent the secondary structure to unfold and/or can reinforce the shape of the secondary structure. A secondary structure that is prevented from unfolding is, for example, more stable.

A "stapled" peptide is a peptide comprising a selected number of standard or non-standard amino acids, further comprising at least two moieties capable of undergoing reaction to promote carbon-carbon bond formation, that has been contacted with a reagent to generate at least one cross-linker between the at least two moieties, which modulates, for example, peptide stability.

A "stitched" peptide, as used herein, is a stapled peptide comprising more than one, that is multiple (two, three, four, five, six, etc.) cross-linked moieties.

The compounds, proteins, or peptides of the present invention (e.g., amino acids, and unstapled, partially stapled, and stapled peptides and proteins, and unstitched, partially stitched, and stitched peptides and proteins) may exist in particular geometric or stereoisomeric forms. The present invention contemplates all such compounds, including cis- and trans-isomers, R- and S-enantiomers, diastereomers, (D)- and (L)-isomers, the racemic mixtures thereof, and other mixtures thereof, as falling within the scope of the invention.

Where an isomer/enantiomer is preferred, it may, in some embodiments, be provided substantially free of the corresponding enantiomer, and may also be referred to as "optically enriched." "Optically enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); Wilen, *Tables of Resolving Agents and Optical Resolutions* p. 268 (E. L. Eliel, Ed., Univ. of Notre Dame Press, Notre Dame, Ind. 1972).

It will be appreciated that the compounds of the present invention, as described herein, may be substituted with any number of substituents or functional moieties. In general, the term "substituted" whether preceded by the term "optionally" or not, and substituents contained in formulas of this invention, refer to the replacement of hydrogen radicals in a given structure with the radical of a specified substituent. When more than one position in any given structure may be substituted with more than one substituent selected from a specified group, the substituent may be either the same or different at every position. As used herein, the term "substituted" is contemplated to include substitution with all permissible substituents of organic compounds, any of the substituents described herein (for example, aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, etc.), and any combination thereof (for example, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like) that results in the formation of a stable moiety. The present invention contemplates any and all such combinations in order to arrive at a stable substituent/moiety. Additional examples of generally applicable substituents are illustrated by the specific embodiments shown in the Examples, which are described herein. For purposes of this invention, heteroatoms such as nitrogen may have hydrogen substituents and/or any suitable substituent as described herein which satisfy the valencies of the heteroatoms and results in the formation of a stable moiety.

As used herein, substituent names which end in the suffix "-ene" refer to a biradical derived from the removal of two hydrogen atoms from the substituent. Thus, for example, acyl is acylene; alkyl is alkylene; alkenyl is alkenylene; alkynyl is alkynylene; heteroalkyl is heteroalkylene, heteroalkenyl is heteroalkenylene, heteroalkynyl is heteroalkynylene, aryl is arylene, and heteroaryl is heteroarylene.

The term "acyl," as used herein, refers to a group having the general formula —C(=O)R$^A$, —C(=O)OR$^A$, —C(=O)—O—C(=O)R$^A$, —C(=O)SR$^A$, —C(=O)N(R$^A$)$_2$, —C(=S) R$^A$, —C(=S)N(R$^A$)$_2$, and —C(=S)S(R$^A$), —C(=NR$^A$)R$^A$, —C(=NR$^A$)OR$^A$, —C(=NR$^A$)SR$^A$, and —C(=NR$^A$)N (R$^A$)$_2$, wherein R$^A$ is hydrogen; halogen; substituted or unsubstituted hydroxyl; substituted or unsubstituted thiol; substituted or unsubstituted amino; substituted or unsubstituted acyl, cyclic or acyclic, substituted or unsubstituted, branched or unbranched aliphatic; cyclic or acyclic, substituted or unsubstituted, branched or unbranched heteroaliphatic; cyclic or acyclic, substituted or unsubstituted, branched or unbranched alkyl; cyclic or acyclic, substituted or unsubstituted, branched or unbranched alkenyl; substituted or unsubstituted alkynyl; substituted or unsubstituted aryl, substituted or unsubstituted heteroaryl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, mono- or di-aliphaticamino, mono- or di-heteroaliphaticamino, mono- or di-alkylamino, mono- or di-heteroalkylamino, mono- or di-arylamino, or mono- or di-heteroarylamino; or two $R^A$ groups taken together form a 5- to 6-membered heterocyclic ring. Exemplary acyl groups include aldehydes (—CHO), carboxylic acids (—CO$_2$H), ketones, acyl halides, esters, amides, imines, carbonates, carbamates, and ureas. Acyl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "acyloxy" refers to a "substituted hydroxyl" of the formula (—OR$^i$), wherein $R^i$ is an optionally substituted acyl group, as defined herein, and the oxygen moiety is directly attached to the parent molecule.

The term "acylene," as used herein, refers to an acyl group having the general formulae: —R$^O$—(C=X$^1$)—R$^O$—, —R$^O$—X$^2$(C=X$^1$)—R$^O$—, or —R$^O$—X$^2$(C=X$^1$)X$^3$—R$^O$—, where X$^1$, X$^2$, and X$^3$ is, independently, oxygen, sulfur, or NR$^r$, wherein R$^r$ is hydrogen or aliphatic, and R$^O$ is an optionally substituted alkylene, alkenylene, alkynylene, heteroalkylene, heteroalkenylene, or heteroalkynylene group, as defined herein. Exemplary acylene groups wherein R$^O$ is alkylene includes —(CH$_2$)$_T$—O(C=O)—(CH$_2$)$_T$—; (CH$_2$)$_T$—NR$^r$(C=O)—(CH$_2$)$_T$—; —(CH$_2$)$_T$—O(C=NR$^r$)—(CH$_2$)$_T$—; —(CH$_2$)$_T$—NR$^r$(C=NR$^r$)—(CH$_2$)$_T$—; —(CH$_2$)$_T$—(C=O)—(CH$_2$)$_T$—; —(CH$_2$)$_T$—(C=NR$^r$)—(CH$_2$)$_T$—; —(CH$_2$)$_T$—S(C=S)—(CH$_2$)$_T$—; —(CH$_2$)$_T$—NR$^r$(C=S)—(CH$_2$)$_T$—; —(CH$_2$)$_T$—S(C=NR$^r$)—(CH$_2$)$_T$—; —(CH$_2$)$_T$—O(C=S)—(CH$_2$)$_T$—; —(CH$_2$)$_T$—(C=S)—(CH$_2$)$_T$—; or —(CH$_2$)$_T$—S(C=O)—(CH$_2$)$_T$—, and the like, which may bear one or more substituents; and wherein each instance of xx is, independently, an integer between 0 to 20. Acylene groups may be cyclic or acyclic, branched or unbranched, substituted or unsubstituted. Acylene substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "aliphatic," as used herein, includes both saturated and unsaturated, nonaromatic, straight chain (i.e., unbranched), branched, acyclic, and cyclic (i.e., carbocyclic) hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl," "alkynyl," and the like. Furthermore, as used herein, the terms "alkyl," "alkenyl," "alkynyl," and the like encompass both substituted and unsubstituted groups. In certain embodiments, as used herein, "aliphatic" is used to indicate those aliphatic groups (cyclic, acyclic, substituted, unsubstituted, branched or unbranched) having 1-20 carbon atoms. Aliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkyl," as used herein, refers to saturated, straight- or branched-chain hydrocarbon radicals derived from a hydrocarbon moiety containing between one and twenty carbon atoms by removal of a single hydrogen atom. In some embodiments, the alkyl group employed in the invention contains 1-20 carbon atoms. In another embodiment, the alkyl group employed contains 1-15 carbon atoms. In another embodiment, the alkyl group employed contains 1-10 carbon atoms. In another embodiment, the alkyl group employed contains 1-8 carbon atoms. In another embodiment, the alkyl group employed contains 1-5 carbon atoms. Examples of alkyl radicals include, but are not limited to, methyl, ethyl, n-propyl, isopropyl, n-butyl, iso-butyl, sec-butyl, sec-pentyl, iso-pentyl, tert-butyl, n-pentyl, neopentyl, n-hexyl, sec-hexyl, n-heptyl, n-octyl, n-decyl, n-undecyl, dodecyl, and the like, which may bear one or more substituents. Alkyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkylene," as used herein, refers to a biradical derived from an alkyl group, as defined herein, by removal of two hydrogen atoms. Alkylene groups may be cyclic or acyclic, branched or unbranched, substituted or unsubstituted. Alkylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenyl," as used herein, denotes a monovalent group derived from a straight- or branched-chain hydrocarbon moiety having at least one carbon-carbon double bond by the removal of a single hydrogen atom. In certain embodiments, the alkenyl group employed in the invention contains 2-20 carbon atoms. In some embodiments, the alkenyl group employed in the invention contains 2-15 carbon atoms. In another embodiment, the alkenyl group employed contains 2-10 carbon atoms. In still other embodiments, the alkenyl group contains 2-8 carbon atoms. In yet other embodiments, the alkenyl group contains 2-5 carbons. Alkenyl groups include, for example, ethenyl, propenyl, butenyl, 1-methyl-2-buten-1-yl, and the like, which may bear one or more substituents. Alkenyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkenylene," as used herein, refers to a biradical derived from an alkenyl group, as defined herein, by removal of two hydrogen atoms. Alkenylene groups may be cyclic or acyclic, branched or unbranched, substituted or unsubstituted. Alkenylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynyl," as used herein, refers to a monovalent group derived from a straight- or branched-chain hydrocarbon having at least one carbon-carbon triple bond by the removal of a single hydrogen atom. In certain embodiments, the alkynyl group employed in the invention contains 2-20 carbon atoms. In some embodiments, the alkynyl group employed in the invention contains 2-15 carbon atoms. In another embodiment, the alkynyl group employed contains 2-10 carbon atoms. In still other embodiments, the alkynyl group contains 2-8 carbon atoms. In still other embodiments, the alkynyl group contains 2-5 carbon atoms. Representative alkynyl groups include, but are not limited to, ethynyl, 2-propynyl (propargyl), 1-propynyl, and the like, which may bear one or more substituents. Alkynyl group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "alkynylene," as used herein, refers to a biradical derived from an alkynylene group, as defined herein, by removal of two hydrogen atoms. Alkynylene groups may be cyclic or acyclic, branched or unbranched, substituted or unsubstituted. Alkynylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "amino," as used herein, refers to a group of the formula (—$NH_2$). A "substituted amino" refers either to a mono-substituted amine (—$NHR^h$) of a disubstituted amine (—$NR^h_2$), wherein the $R^h$ substituent is any substituent as described herein that results in the formation of a stable moiety (e.g., a suitable amino protecting group; aliphatic, alkyl, alkenyl, alkynyl, heteroaliphatic, heterocyclic, aryl, heteroaryl, acyl, amino, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). In certain embodiments, the $R^h$ substituents of the disubstituted amino group (—$NR^h_2$) form a 5- to 6-membered heterocyclic ring.

The term "alkoxy" refers to a "substituted hydroxyl" of the formula (—$OR^i$), wherein $R^i$ is an optionally substituted alkyl group, as defined herein, and the oxygen moiety is directly attached to the parent molecule.

The term "alkylthioxy" refers to a "substituted thiol" of the formula (—$SR^r$), wherein $R^r$ is an optionally substituted alkyl group, as defined herein, and the sulfur moiety is directly attached to the parent molecule.

The term "alkylamino" refers to a "substituted amino" of the formula (—$NR^h_2$), wherein $R^h$ is, independently, a hydrogen or an optionally substituted alkyl group, as defined herein, and the nitrogen moiety is directly attached to the parent molecule.

The term "aryl," as used herein, refer to stable aromatic mono- or polycyclic ring system having 3-20 ring atoms, of which all the ring atoms are carbon, and which may be substituted or unsubstituted. In certain embodiments of the present invention, "aryl" refers to a mono, bi, or tricyclic $C_4$-$C_{20}$ aromatic ring system having one, two, or three aromatic rings which include, but not limited to, phenyl, biphenyl, naphthyl, and the like, which may bear one or more substituents. Aryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "arylene," as used herein refers to an aryl biradical derived from an aryl group, as defined herein, by removal of two hydrogen atoms. Arylene groups may be substituted or unsubstituted. Arylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted). Additionally, arylene groups may be incorporated as a linker group into an alkylene, alkenylene, alkynylene, heteroalkylene, heteroalkenylene, or heteroalkynylene group, as defined herein.

The term "arylalkyl," as used herein, refers to an aryl substituted alkyl group, wherein the terms "aryl" and "alkyl" are defined herein, and wherein the aryl group is attached to the alkyl group, which in turn is attached to the parent molecule. An exemplary arylalkyl group includes benzyl.

The term "aryloxy" refers to a "substituted hydroxyl" of the formula (—$OR^i$), wherein $R^i$ is an optionally substituted aryl group, as defined herein, and the oxygen moiety is directly attached to the parent molecule.

The term "arylamino" refers to a "substituted amino" of the formula (—$NR^h{}_2$), wherein $R^h$ is, independently, a hydrogen or an optionally substituted aryl group, as defined herein, and the nitrogen moiety is directly attached to the parent molecule.

The term "arylthioxy" refers to a "substituted thiol" of the formula (—$SR^r$), wherein $R^r$ is an optionally substituted aryl group, as defined herein, and the sulfur moiety is directly attached to the parent molecule.

The term "azido," as used herein, refers to a group of the formula (—$N_3$).

The term "cyano," as used herein, refers to a group of the formula (—CN).

The terms "halo" and "halogen," as used herein, refer to an atom selected from fluorine (fluoro, —F), chlorine (chloro, —Cl), bromine (bromo, —Br), and iodine (iodo, —I).

The term "heteroaliphatic," as used herein, refers to an aliphatic moiety, as defined herein, which includes both saturated and unsaturated, nonaromatic, straight chain (i.e., unbranched), branched, acyclic, cyclic (i.e., heterocyclic), or polycyclic hydrocarbons, which are optionally substituted with one or more functional groups, and that contain one or more oxygen, sulfur, nitrogen, phosphorus, or silicon atoms, e.g., in place of carbon atoms. In certain embodiments, heteroaliphatic moieties are substituted by independent replacement of one or more of the hydrogen atoms thereon with one or more substituents. As will be appreciated by one of ordinary skill in the art, "heteroaliphatic" is intended herein to include, but is not limited to, heteroalkyl, heteroalkenyl, heteroalkynyl, heterocycloalkyl, heterocycloalkenyl, and heterocycloalkynyl moieties. Thus, the term "heteroaliphatic" includes the terms "heteroalkyl," "heteroalkenyl," "heteroalkynyl," and the like. Furthermore, as used herein, the terms "heteroalkyl," "heteroalkenyl," "heteroalkynyl," and the like encompass both substituted and unsubstituted groups. In certain embodiments, as used herein, "heteroaliphatic" is used to indicate those heteroaliphatic groups (cyclic, acyclic, substituted, unsubstituted, branched or unbranched) having 1-20 carbon atoms. Heteroaliphatic group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkyl," as used herein, refers to an alkyl moiety, as defined herein, which contain one or more oxygen, sulfur, nitrogen, phosphorus, or silicon atoms, e.g., in place of carbon atoms.

The term "heteroalkylene," as used herein, refers to a biradical derived from an heteroalkyl group, as defined herein, by removal of two hydrogen atoms. Heteroalkylene groups may be cyclic or acyclic, branched or unbranched, substituted or unsubstituted. Heteroalkylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroalkenyl," as used herein, refers to an alkenyl moiety, as defined herein, which contain one or more oxygen, sulfur, nitrogen, phosphorus, or silicon atoms, e.g., in place of carbon atoms.

The term "heteroalkenylene," as used herein, refers to a biradical derived from an heteroalkenyl group, as defined herein, by removal of two hydrogen atoms. Heteroalkenylene groups may be cyclic or acyclic, branched or unbranched, substituted or unsubstituted.

The term "heteroalkynyl," as used herein, refers to an alkynyl moiety, as defined herein, which contain one or more oxygen, sulfur, nitrogen, phosphorus, or silicon atoms, e.g., in place of carbon atoms.

The term "heteroalkynylene," as used herein, refers to a biradical derived from an heteroalkynyl group, as defined herein, by removal of two hydrogen atoms. Heteroalkynylene groups may be cyclic or acyclic, branched or unbranched, substituted or unsubstituted.

The term "heteroalkylamino" refers to a "substituted amino" of the formula (—$NR^h{}_2$), wherein $R^h$ is, independently, a hydrogen or an optionally substituted heteroalkyl group, as defined herein, and the nitrogen moiety is directly attached to the parent molecule.

The term "heteroalkyloxy" refers to a "substituted hydroxyl" of the formula (—$OR^i$), wherein $R^i$ is an optionally substituted heteroalkyl group, as defined herein, and the oxygen moiety is directly attached to the parent molecule.

The term "heteroalkylthioxy" refers to a "substituted thiol" of the formula (—$SR^r$), wherein $R^r$ is an optionally substituted heteroalkyl group, as defined herein, and the sulfur moiety is directly attached to the parent molecule.

The term "heterocyclic," "heterocycles," or "heterocyclyl," as used herein, refers to a cyclic heteroaliphatic group. A heterocyclic group refers to a non-aromatic, partially unsaturated or fully saturated, 3- to 10-membered ring system, which includes single rings of 3 to 8 atoms in size, and bi- and tri-cyclic ring systems which may include aromatic five- or six-membered aryl or heteroaryl groups fused to a non-aromatic ring. These heterocyclic rings include those having from one to three heteroatoms independently selected from oxygen, sulfur, and nitrogen, in which the nitrogen and sulfur heteroatoms may optionally be oxidized and the nitrogen heteroatom may optionally be quaternized. In certain embodiments, the term heterocyclic refers to a non-aromatic 5-, 6-, or 7-membered ring or polycyclic group wherein at least one ring atom is a heteroatom selected from O, S, and N (wherein the nitrogen and sulfur heteroatoms may be optionally oxidized), and the remaining ring atoms are carbon, the radical being joined to the rest of the molecule via any of the ring atoms. Heterocycyl groups include, but are not limited to, a bi- or tri-cyclic group, comprising fused five, six, or seven-membered rings having between one and three heteroatoms independently selected from the oxygen, sulfur, and nitrogen, wherein (i) each 5-membered ring has 0 to 2 double bonds, each 6-membered ring has 0 to 2 double bonds, and each 7-membered ring has 0 to 3 double bonds, (ii) the nitrogen and sulfur heteroatoms may be optionally oxidized, (iii) the nitrogen heteroatom may optionally be quaternized, and (iv) any of the above heterocyclic rings may be fused to an aryl or heteroaryl ring. Exemplary heterocycles include azacyclopropanyl, azacyclobutanyl, 1,3-diazatidinyl, piperidinyl, piperazinyl, azocanyl, thiaranyl, thietanyl, tetrahydrothiophenyl, dithiolanyl, thiacyclohexanyl, oxiranyl, oxetanyl, tetrahydrofuranyl, tetrahydropuranyl, dioxanyl, oxathiolanyl, morpholinyl, thioxanyl, tetrahydronaphthyl, and the like, which may bear one or more substituents. Substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroaryl," as used herein, refer to stable aromatic mono- or polycyclic ring system having 3-20 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include, but are not limited to pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl, oxadiaziolyl, and the like, which may bear one or more substituents. Heteroaryl substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, sulfinyl, sulfonyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylene," as used herein, refers to a biradical derived from an heteroaryl group, as defined herein, by removal of two hydrogen atoms. Heteroarylene groups may be substituted or unsubstituted. Additionally, heteroarylene groups may be incorporated as a linker group into an alkylene, alkenylene, alkynylene, heteroalkylene, heteroalkenylene, or heteroalkynylene group, as defined herein. Heteroarylene group substituents include, but are not limited to, any of the substituents described herein, that result in the formation of a stable moiety (e.g., aliphatic, alkyl, alkenyl, alkynyl, heteroaliphatic, heterocyclic, aryl, heteroaryl, acyl, oxo, imino, thiooxo, cyano, isocyano, amino, azido, nitro, hydroxyl, thiol, halo, aliphaticamino, heteroaliphaticamino, alkylamino, heteroalkylamino, arylamino, heteroarylamino, alkylaryl, arylalkyl, aliphaticoxy, heteroaliphaticoxy, alkyloxy, heteroalkyloxy, aryloxy, heteroaryloxy, aliphaticthioxy, heteroaliphaticthioxy, alkylthioxy, heteroalkylthioxy, arylthioxy, heteroarylthioxy, acyloxy, and the like, each of which may or may not be further substituted).

The term "heteroarylamino" refers to a "substituted amino" of the ($-NR^h_2$), wherein $R^h$ is, independently, a hydrogen or an optionally substituted heteroaryl group, as defined herein, and the nitrogen moiety is directly attached to the parent molecule.

The term "heteroaryloxy" refers to a "substituted hydroxyl" of the formula ($-OR^i$), wherein $R^i$ is an optionally substituted heteroaryl group, as defined herein, and the oxygen moiety is directly attached to the parent molecule.

The term "heteroarylthioxy" refers to a "substituted thiol" of the formula ($-SR^r$), wherein $R^r$ is an optionally substituted heteroaryl group, as defined herein, and the sulfur moiety is directly attached to the parent molecule.

The term "hydroxy" or "hydroxyl," as used herein, refers to a group of the formula (—OH). A "substituted hydroxyl" refers to a group of the formula ($-OR^i$), wherein $R^i$ can be any substituent which results in a stable moiety (e.g., a suitable hydroxyl protecting group; aliphatic, alkyl, alkenyl, alkynyl, heteroaliphatic, heterocyclic, aryl, heteroaryl, acyl, nitro, alkylaryl, arylalkyl, and the like, each of which may or may not be further substituted).

The term "imino," as used herein, refers to a group of the formula ($=NR^r$), wherein $R^r$ corresponds to hydrogen or any substituent as described herein, that results in the formation of a stable moiety (for example, a suitable amino protecting group; aliphatic, alkyl, alkenyl, alkynyl, heteroaliphatic, heterocyclic, aryl, heteroaryl, acyl, amino, hydroxyl, alkylaryl, arylalkyl, and the like, each of which may or may not be further substituted).

The term "isocyano," as used herein, refers to a group of the formula (—NC).

The term "nitro," as used herein, refers to a group of the formula ($-NO_2$).

The term "oxo," as used herein, refers to a group of the formula (=O).

As used herein, the term "resin" refers to a resin useful for solid phase synthesis. Solid phase synthesis is a well-known synthetic technique; see generally, Atherton, E., Sheppard, R. C. *Solid Phase Peptide Synthesis: A Practical Approach*, IRL Press, Oxford, England, 1989, and Stewart J. M., Young, J. D. *Solid Phase Peptide Synthesis*, 2nd edition, Pierce Chemical Company, Rockford, 1984, the entire contents of each of which are hereby incorporated herein by reference. Exemplary resins which may be employed by the present invention include, but are not limited to:

(1) alkenyl resins (e.g., REM resin, vinyl sulfone polymer-bound resin, vinyl-polystyrene resin);

(2) amine functionalized resins (e.g., amidine resin, N-(4-Benzyloxybenzyl)hydroxylamine polymer bound, (aminomethyl)polystyrene, polymer bound (R)-(+)-a-methylbenzylamine, 2—Chlorotrityl Knorr resin, 2-N-Fmoc-Aminodibenzocyclohepta-1,4-diene, polymer-bound resin, 4-[4-(1-Fmoc-aminoethyl)-2-methoxy-5-nitrophenoxy]butyramidomethyl-polystyrene resin, 4-Benzyloxybenzylamine, polymer-bound, 4-Carboxybenzenesulfonamide, polymer-bound, Bis(tert-butoxycarbonyl)thiopseudourea, polymer-bound, Dimethylaminomethyl-polystyrene, Fmoc-3-amino-3-(2-nitrophenyl)propionic acid, polymer-bound, N-Methyl aminomethylated polystyrene, PAL resin, Sieber amide resin, tert-Butyl N-(2-mercaptoethyl)carbamate, polymer-bound, Triphenylchloromethane-4-carboxamide polymer bound);

(3) benzhydrylamine (BHA) resins (e.g., 2—Chlorobenzhydryl chloride, polymer-bound, HMPB-benzhydrylamine polymer bound, 4-Methylbenzhydrol, polymer-bound, Benzhydryl chloride, polymer-bound, Benzhydrylamine polymer-bound);

(4) Br-functionalized resins (e.g., 4-(Benzyloxy)benzyl bromide polymer bound, 4-Bromopolystyrene, Brominated PPOA resin, Brominated Wang resin, Bromoacetal, polymer-bound, Bromopolystyrene, HypoGel® 200 Br, Polystyrene A-Br for peptide synthesis, Selenium bromide, polymer-bound, TentaGel HL-Br, TentaGel MB-Br, TentaGel S-Br, TentaGel S-Br);

(5) Chloromethyl resins (e.g., 5-[4-(Chloromethyl)phenyl]pentyl]styrene, polymer-bound, 4-(Benzyloxy)benzyl chloride polymer bound, 4-Methoxybenzhydryl chloride, polymer-bound);

(6) CHO-functionalized resins (e.g., (4-Formyl-3-methoxyphenoxymethyl)polystyrene, (4-Formyl-3-methoxyphenoxymethyl)polystyrene, 3-Benzyloxybenzaldehyde, polymer-bound, 4-Benzyloxy-2,6-dimethoxybenzaldehyde, polymer-bound, Formylpolystyrene, HypoGel® 200 CHO, Indole resin, Polystyrene A—CH(OEt)$_2$, TentaGel HL—CH(OEt)$_2$);

(7) Cl-functionalized resins (e.g., Benzoyl chloride polymer bound, (chloromethyl)polystyrene, Merrifield's resin);

(8) CO$_2$H functionalized resins (e.g., Carboxyethylpolystryrene, HypoGel® 200 COOH, Polystyrene AM—COOH, TentaGel HL—COOH, TentaGel MB—COOH, TentaGel S-COOH);

(9) Hypo-Gel resins (e.g., HypoGel® 200 FMP, Hypo-Gel® 200 PHB, HypoGel® 200 Trt-OH, HypoGel® 200 HMB);

(10) I-functionalized resins (e.g., 4-Iodophenol, polymer-bound, Iodopolystyrene); Janda-Jels™ (JandaJel$^a$-Rink amide, JandaJel-NH$_2$, JandaJel—Cl, JandaJel-4-Mercaptophenol, JandaJel-OH, JandaJel-1-(3-Dimethylaminopropyl)-3-ethylcarbodiimide, JandaJel-1,3,4,6,7,8-hexahydro-2H-pyrimido-[1,2-α]pyrimidine, JandaJel-morpholine, JandaJel-polypyridine, JandaJel-Triphenylphosphine, JandaJel-Wang);

(11) MBHA resins (3[4'-(Hydroxymethyl)phenoxy]propionic acid-4-methylbenzhydrylamine resin, 4-(Hydroxymethyl)phenoxyacetic acid polymer-bound to MBHA resin, HMBA-4-methylbenzhydrylamine polymer bound, 4-Methylbenzhydrylamine hydrochloride polymer bound Capacity (amine));

(12) NH$_2$ functionalized resins ((Aminomethyl)polystyrene, (Aminomethyl)polystyrene, HypoGel® 200 NH2, Polystyrene AM-NH$_2$, Polystyrene Microspheres 2-aminoethylated, Polystyrol Microspheres 2-bromoethylated, Polystyrol Microspheres 2-hydroxyethylated, TentaGel HL-NH$_2$, Tentagel M Br, Tentagel M NH$_2$, Tentagel M OH, TentaGel MB-NH$_2$, TentaGel S-NH$_2$, TentaGel S-NH$_2$);

(13) OH-functionalized resins (e.g., 4-hydroxymethylbenzoic acid, polymer-bound, Hydroxymethyl Resins, OH-functionalized Wang Resins);

(14) oxime resins (e.g., 4—Chlorobenzophenone oxime polymer bound, Benzophenone oxime polymer bound, 4-Methoxybenzophenone oxime polymer bound);

(15) PEG resins (e.g., ethylene glycol polymer bound);

(16) Boc-/Blz peptide synthesis resins (e.g., Boc-Lys(Boc)-Lys[Boc-Lys(Boc)]-Cys(Acm)-b-Ala-O-PAM resin, Boc-Lys(Fmoc)-Lys[Boc-Lys(Fmoc)]-b-Ala-O-Pam resin, Boc-Lys(Boc)-Lys[Boc-Lys(Boc)]-Lys{Boc-Lys(Boc)-Lys[Boc-Lys(Boc)]}-b-Ala-O-PAM resin, Boc-Lys(Fmoc)-Lys[Boc-Lys(Fmoc)]-Lys[Boc-Lys(Fmoc)]-Lys{Boc-Lys(Fmoc)]}-b-Ala-O-PAM resin, Boc-Lys(Boc)-Lys[Boc-Lys(Boc)]-Lys{Boc-Lys(Boc)-Lys[Boc-Lys(Boc)]}—Cys(Acm)-b-Ala-O-PAM resin, Preloaded PAM resins);

(17) Fmoc-/t-Bu peptide synthesis resins (e.g., Fmoc-Lys(Fmoc)-Lys[Fmoc-Lys(Fmoc)]-b-Ala-O-Wang resin, Fmoc-Lys(Fmoc)-Lys[Fmoc-Lys(Fmoc)]-Lys{Fmoc-Lys(Fmoc)-Lys[Fmoc-Lys(Fmoc)]}-b-Ala-O-Wang resin, Preloaded TentaGel® S Trityl Resins, Preloaded TentaGel® Resins, Preloaded Trityl Resins, Preloaded Wang Resins, Trityl Resins Preloaded with Amino Alcohols);

(19) thiol-functionalized resins (e.g., HypoGel® 200 S-Trt, Polystyrene AM-S-Trityl, TentaGel HL-S-Trityl, TentaGel MB-S-Trityl, TentaGel S-S-Trityl); and

(20) Wang resins (e.g., Fmoc-Ala-Wang resin, Fmoc-Arg (Pbf)-Wang resin, Fmoc-Arg(Pmc)-Wang resin, Fmoc-Asn (Trt)-Wang resin, Fmoc-Asp(OtBu)-Wang resin, Fmoc-Cys (Acm)-Wang resin, Fmoc-Cys(StBu)-Wang resin, Fmoc-Cys (Trt) Wang resin, Fmoc-Gln(Trt)-Wang resin, Fmoc-Glu (OtBu)-Wang resin, Fmoc-Gly-Wang resin, Fmoc-His(Trt)-Wang resin, Fmoc-Ile-Wang resin, Fmoc-Leu-Wang resin, Fmoc-Lys(Boc)-Wang resin, Fmoc-Met-Wang resin, Fmoc-D-Met-Wang resin, Fmoc-Phe-Wang resin, Fmoc-Pro-Wang resin, Fmoc-Ser(tBu)-Wang resin, Fmoc-Ser(Trt)-Wang resin, Fmoc-Thr(tBu)-Wang resin, Fmoc-Trp(Boc) Wang resin, Fmoc-Trp-Wang resin, Fmoc-Tyr(tBu)-Wang resin, Fmoc-Val-Wang resin).

The term "stable moiety," as used herein, preferably refers to a moiety which possess stability sufficient to allow manufacture, and which maintains its integrity for a sufficient period of time to be useful for the purposes detailed herein.

A "suitable amino-protecting group," as used herein, is well known in the art and include those described in detail in *Protecting Groups in Organic Synthesis*, T. W. Greene and P. G. M. Wuts, 3rd edition, John Wiley & Sons, 1999, the entirety of which is incorporated herein by reference. Suitable amino-protecting groups include methyl carbamate, ethyl carbamate, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1- methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitrobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl (o-nitrophenyl)methyl carbamate, phenothiazinyl-(10)-carbonyl derivative, N'-p-toluenesulfonylaminocarbonyl derivative, N'-phenylaminothiocarbonyl derivative, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxycarbonylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium)benzyl carbamate, 2,4,6-trimethylbenzyl carbamate, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxycarbonylamino)acetamide, 3-(p-hydroxyphenyl)propanamide, 3-(o-nitrophenyl) propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide, o-(benzoyloxymethyl)benzamide, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, Ntriphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N-(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl) amine, N-borane derivative, N-diphenylborinic acid derivative, N-[phenyl(pentacarbonylchromium- or tungsten) carbonyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, 3-nitropyridinesulfenamide (Npys), p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

A "suitable carboxylic acid protecting group" or "protected carboxylic acid," as used herein, are well known in the art and include those described in detail in Greene (1999). Examples of suitably protected carboxylic acids further include, but are not limited to, silyl-, alkyl-, alkenyl-, aryl-, and arylalkyl-protected carboxylic acids. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

A "suitable hydroxyl protecting group," as used herein, is well known in the art and include those described in detail in Protecting Groups in Organic Synthesis, T. W. Greene and P. G. M. Wuts, 3$^{rd}$ edition, John Wiley & Sons, 1999, the entirety of which is incorporated herein by reference. Suitable hydroxyl protecting groups include methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl, p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl)ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxycarbonyl)benzoate, α-naphthoate, nitrate, alkyl N,N,N';N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts). For protecting 1,2- or 1,3-diols, the protecting groups include methylene acetal, ethylidene acetal, 1-t-butylethylidene ketal, 1-phenylethylidene ketal, (4-methoxyphenyl)ethylidene acetal, 2,2,2-trichloroethylidene acetal, acetonide, cyclopentylidene ketal, cyclohexylidene ketal, cycloheptylidene ketal, benzylidene acetal, p-methoxybenzylidene acetal, 2,4-dimethoxybenzylidene ketal, 3,4-dimethoxybenzylidene acetal, 2-nitrobenzylidene acetal, methoxymethylene acetal, ethoxymethylene acetal, dimethoxymethylene ortho ester, 1-methoxyethylidene ortho ester, 1-ethoxyethylidine ortho ester, 1,2-dimethoxyethylidene ortho ester, α-methoxybenzylidene ortho ester, 1-(N,N-dimethylamino)ethylidene derivative, α-(N,N'-dimethylamino)benzylidene derivative, 2-oxacyclopentylidene ortho ester, di-t-butylsilylene group (DTBS), 1,3-(1,1,3,3-tetraisopropyldisiloxanylidene) derivative (TIPDS), tetra-t-butoxydisiloxane-1,3-diylidene derivative (TBDS), cyclic carbonates, cyclic boronates, ethyl boronate, and phenyl boronate.

A "suitable thiol protecting group," as used herein, are well known in the art and include those described in detail in *Protecting Groups in Organic Synthesis*, T. W. Greene and P. G. M. Wuts, 3$^{rd}$ edition, John Wiley & Sons, 1999, the entirety of which is incorporated herein by reference. Examples of suitably protected thiol groups further include, but are not limited to, thioesters, carbonates, sulfonates allyl thioethers, thioethers, silyl thioethers, alkyl thioethers, arylalkyl thioethers, and alkyloxyalkyl thioethers. Examples of suitable ester groups include formates, acetates, proprionates, pentanoates, crotonates, and benzoates. Specific examples of suitable ester groups include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)pentanoate, pivaloate (trimethylacetate), crotonate, 4-methoxy-crotonate, benzoate, p-benzylbenzoate, 2,4,6-trimethylbenzoate. Examples of suitable carbonates include 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl carbonate. Examples of suitable silyl groups include trimethylsilyl, triethylsilyl, t-butyldimethylsilyl, t-butyldiphenylsilyl, triisopropylsilyl ether, and other trialkylsilyl ethers. Examples of suitable alkyl groups include methyl, benzyl, p-methoxybenzyl, 3,4-dimethoxybenzyl, trityl, t-butyl, and allyl ether, or derivatives thereof. Examples of suitable arylalkyl groups include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, 2- and 4-picolyl ethers.

The term "thio" or "thiol," as used herein, refers to a group of the formula (—SH). A "substituted thiol" refers to a group of the formula (—SR$^r$), wherein R$^r$ can be any substituent that results in the formation of a stable moiety (e.g., a suitable thiol protecting group; aliphatic, alkyl, alkenyl, alkynyl, heteroaliphatic, heterocyclic, aryl, heteroaryl, acyl, sulfinyl, sulfonyl, cyano, nitro, alkylaryl, arylalkyl, and the like, each of which may or may not be further substituted).

The term "thiooxo," as used herein, refers to a group of the formula (=S).

As used herein, a "pharmaceutically acceptable form thereof" includes any pharmaceutically acceptable salts, prodrugs, tautomers, enantiomers, diastereomers, stereoisomers, isomers, and/or polymorphs of a compound of the present invention, as defined below and herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

As used herein, the term "prodrug" refers to a derivative of a parent compound that requires transformation within the body in order to release the parent compound. In certain cases, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage. In recent years several types of bioreversible derivatives have been exploited for utilization in designing prodrugs. Using esters as a prodrug type for compounds containing a carboxyl or hydroxyl functionality is known in the art as described, for example, in "*The Organic Chemistry of Drug Design and Drug Interaction*" Richard Silverman, published by Academic Press (1992).

As used herein, the term "tautomer" includes two or more interconvertable compounds resulting from at least one formal migration of a hydrogen atom and at least one change in valency (e.g., a single bond to a double bond, a triple bond to a double bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

As used herein, the term "isomers" includes any and all geometric isomers and stereoisomers. For example, "isomers" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

The term "amino acid" refers to a molecule containing both an amino group and a carboxyl group. Amino acids include alpha-amino acids and beta-amino acids, the structures of which are depicted below. In certain embodiments, an amino acid is an alpha amino acid.

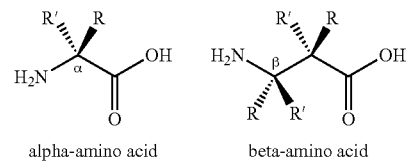

alpha-amino acid   beta-amino acid

Suitable amino acids include, without limitation, natural alpha-amino acids such as D- and L-isomers of the 20 common naturally occurring alpha-amino acids found in peptides and proteins (e.g., A, R, N, C, D, Q, E, G, H, I, L, K, M, F, P, S, T, W, Y, V, as depicted in Table 1 below), unnatural alpha-amino acids (as depicted in Tables 2 and 3 below), natural beta-amino acids (e.g., beta-alanine), and unnatural beta-amino acids.

Amino acids used in the construction of peptides of the present invention may be prepared by organic synthesis, or obtained by other routes, such as, for example, degradation of or isolation from a natural source. In certain embodiments of the present invention, the formula —[$X_{AA}$]— corresponds to the natural and/or unnatural amino acids having the following formulae:

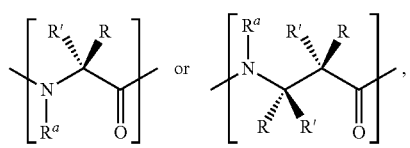

wherein R and R' correspond a suitable amino acid side chain, as defined herein, and $R^a$ is as defined herein.

TABLE 1

| Exemplary natural alpha-amino acids | Suitable amino acid side chains | |
|---|---|---|
| | R | R' |
| L-Alanine (A) | —$CH_3$ | —H |
| L-Arginine (R) | —$CH_2CH_2CH_2$—NHC(=NH)$NH_2$ | —H |
| L-Asparagine (N) | —$CH_2$C(=O)$NH_2$ | —H |
| L-Aspartic acid (D) | —$CH_2CO_2H$ | —H |
| L-Cysteine (C) | —$CH_2SH$ | —H |
| L-Glutamic acid (E) | —$CH_2CH_2CO_2H$ | —H |
| L-Glutamine (Q) | —$CH_2CH_2$C(=O)$NH_2$ | —H |
| Glycine (G) | —H | —H |
| L-Histidine (H) | —$CH_2$-2-(1H-imidazole) | —H |
| L-Isoleucine (I) | -sec-butyl | —H |
| L-Leucine (L) | -iso-butyl | —H |
| L-Lysine (K) | —$CH_2CH_2CH_2CH_2NH_2$ | —H |
| L-Methionine (M) | —$CH_2CH_2SCH_3$ | —H |
| L-Phenylalanine (F) | —$CH_2$Ph | —H |
| L-Proline (P) | -2-(pyrrolidine) | —H |
| L-Serine (S) | —$CH_2OH$ | —H |
| L-Threonine (T) | —$CH_2$CH(OH)($CH_3$) | —H |
| L-Tryptophan (W) | —$CH_2$-3-(1H-indole) | —H |
| L-Tyrosine (Y) | —$CH_2$-(p-hydroxyphenyl) | —H |
| L-Valine (V) | -isopropyl | —H |

TABLE 2

| Exemplary unnatural alpha-amino acids | Suitable amino acid side chains | |
|---|---|---|
| | R | R' |
| D-Alanine | —H | —$CH_3$ |
| D-Arginine | —H | —$CH_2CH_2CH_2$—NHC(=NH)$NH_2$ |
| D-Asparagine | —H | —$CH_2$C(=O)$NH_2$ |
| D-Aspartic acid | —H | —$CH_2CO_2H$ |
| D-Cysteine | —H | —$CH_2SH$ |
| D-Glutamic acid | —H | —$CH_2CH_2CO_2H$ |
| D-Glutamine | —H | —$CH_2CH_2$C(=O)$NH_2$ |
| D-Histidine | —H | —$CH_2$-2-(1H-imidazole) |
| D-Isoleucine | —H | -sec-butyl |
| D-Leucine | —H | -iso-butyl |
| D-Lysine | —H | —$CH_2CH_2CH_2CH_2NH_2$ |
| D-Methionine | —H | —$CH_2CH_2SCH_3$ |
| D-Phenylalanine | —H | —$CH_2$Ph |
| D-Proline | —H | -2-(pyrrolidine) |
| D-Serine | —H | —$CH_2OH$ |
| D-Threonine | —H | —$CH_2$CH(OH)($CH_3$) |
| D-Tryptophan | —H | —$CH_2$-3-(1H-indole) |
| D-Tyrosine | —H | —$CH_2$-(p-hydroxyphenyl) |
| D-Valine | —H | -isopropyl |
| Di-vinyl | —CH=$CH_2$ | —CH=$CH_2$ |

| Exemplary unnatural alpha-amino acids | R and R' are equal to: | |
|---|---|---|
| α-methyl-Alanine (Aib) | —$CH_3$ | —$CH_3$ |
| α-methyl-Arginine | —$CH_3$ | —$CH_2CH_2CH_2$—NHC(=NH)$NH_2$ |
| α-methyl-Asparagine | —$CH_3$ | —$CH_2$C(=O)$NH_2$ |
| α-methyl-Aspartic acid | —$CH_3$ | —$CH_2CO_2H$ |
| α-methyl-Cysteine | —$CH_3$ | —$CH_2SH$ |
| α-methyl-Glutamic acid | —$CH_3$ | —$CH_2CH_2CO_2H$ |
| α-methyl-Glutamine | —$CH_3$ | —$CH_2CH_2$C(=O)$NH_2$ |
| α-methyl-Histidine | —$CH_3$ | —$CH_2$-2-(1H-imidazole) |
| α-methyl-Isoleucine | —$CH_3$ | -sec-butyl |
| α-methyl-Leucine | —$CH_3$ | -iso-butyl |
| α-methyl-Lysine | —$CH_3$ | —$CH_2CH_2CH_2CH_2NH_2$ |
| α-methyl-Methionine | —$CH_3$ | —$CH_2CH_2SCH_3$ |
| α-methyl-Phenylalanine | —$CH_3$ | —$CH_2$Ph |
| α-methyl-Proline | —$CH_3$ | -2-(pyrrolidine) |
| α-methyl-Serine | —$CH_3$ | —$CH_2OH$ |
| α-methyl-Threonine | —$CH_3$ | —$CH_2$CH(OH)($CH_3$) |
| α-methyl-Tryptophan | —$CH_3$ | —$CH_2$-3-(1H-indole) |
| α-methyl-Tyrosine | —$CH_3$ | —$CH_2$-(p-hydroxyphenyl) |
| α-methyl-Valine | —$CH_3$ | -isopropyl |
| Di-vinyl | —CH=$CH_2$ | —CH=$CH_2$ |
| Norleucine | —H | —$CH_2CH_2CH_2CH_3$ |

TABLE 3

| | Suitable amino acid side chains |
|---|---|
| Examplary unnatural alpha-amino acids | R and R' is equal to hydrogen or —$CH_3$, and: |
| Terminally unsaturated alpha-amino acids and bis alpha-amino acids (e.g., modified cysteine, modified lysine, modified tryptophan, modified serine, modified threonine, modified proline, modified histidine, modified alanine, and the like). | —$(CH_2)_g$—S—$(CH_2)_g$CH=$CH_2$, —$(CH_2)_g$—O—$(CH_2)_g$CH=$CH_2$, —$(CH_2)_g$—NH—$(CH_2)_g$CH=$CH_2$, —$(CH_2)_g$—(C=O)—S—$(CH_2)_g$CH=$CH_2$, —$(CH_2)_g$—(C=O)—O—$(CH_2)_g$CH=$CH_2$, —$(CH_2)_g$—(C=O)—NH—$(CH_2)_g$CH=$CH_2$, —$CH_2CH_2CH_2CH_2$—NH—$(CH_2)_g$CH=$CH_2$, —$(C_6H_5)$—p-O—$(CH_2)_g$CH=$CH_2$, —CH($CH_3$)—O—$(CH_2)_g$CH=$CH_2$, —$CH_2$CH(—O—CH=$CH_2$)($CH_3$), -histidine-N(($CH_2)_g$CH=$CH_2$), -tryptophan-N(($CH_2)_g$CH=$CH_2$), and —$(CH_2)_{g+1}$(CH=$CH_2$), wherein: each instance of g is, independently, 0 to 10, inclusive. |

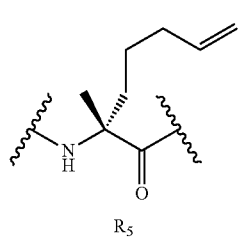

TABLE 3-continued

Suitable amino acid side chains

| Examplary unnatural alpha-amino acids | R and R' is equal to hydrogen or —CH$_3$, and: |

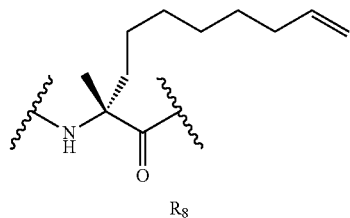

R$_8$

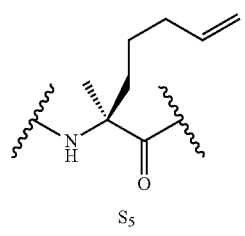 [SMILES: *N[C@@](C)(CCCC=C)C(*)=O ; "S5"]

S$_5$

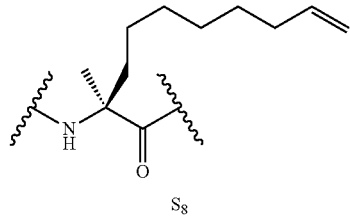 [SMILES: *N[C@@](C)(CCCCCCC=C)C(*)=O ; "S8"]

S$_8$

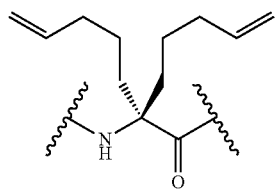

B$_5$

There are many known unnatural amino acids any of which may be included in the peptides of the present invention. See, for example, S. Hunt, *The Non-Protein Amino Acids: In Chemistry and Biochemistry of the Amino Acids*, edited by G. C. Barrett, Chapman and Hall, 1985. Some examples of unnatural amino acids are 4-hydroxyproline, desmosine, gamma-aminobutyric acid, beta-cyanoalanine, norvaline, 4-(E)-butenyl-4(R)-methyl-N-methyl-L-threonine, N-methyl-L-leucine, 1-amino-cyclopropanecarboxylic acid, 1-amino-2-phenyl-cyclopropanecarboxylic acid, 1-aminocyclobutanecarboxylic acid, 4-amino-cyclopentenecarboxylic acid, 3-amino-cyclohexanecarboxylic acid, 4-piperidylacetic acid, 4-amino-1-methylpyrrole-2-carboxylic acid, 2,4-diaminobutyric acid, 2,3-diaminopropionic acid, 2,4-diaminobutyric acid, 2-aminoheptanedioic acid, 4-(aminomethyl)benzoic acid, 4-aminobenzoic acid, ortho-, meta- and para-substituted phenylalanines (e.g., substituted with —C(=O)C$_6$H$_5$; —CF$_3$; —CN; -halo; —NO$_2$; —CH$_3$), disubstituted phenylalanines, substituted tyrosines (e.g., further substituted with —C(=O)C$_6$H$_5$; —CF$_3$; —CN; -halo; —NO$_2$; —CH$_3$), and statine. Additionally, the amino acids suitable for use in the present invention may be derivatized to include amino acid residues that are hydroxylated, phosphorylated, sulfonated, acylated, lipidated, and glycosylated, to name a few.

The term "amino acid side chain" refers to a group attached to the alpha- or beta-carbon of an amino acid. A "suitable amino acid side chain" includes, but is not limited to, any of the suitable amino acid side chains as defined above, and as provided in Tables 1 to 3.

For example, suitable amino acid side chains include methyl (as the alpha-amino acid side chain for alanine is methyl), 4-hydroxyphenylmethyl (as the alpha-amino acid side chain for tyrosine is 4-hydroxyphenylmethyl) and thiomethyl (as the alpha-amino acid side chain for cysteine is thiomethyl), etc. A "terminally unsaturated amino acid side chain" refers to an amino acid side chain bearing a terminal unsaturated moiety, such as a substituted or unsubstituted, double bond (e.g., olefinic) or a triple bond (e.g., acetylenic), that participates in a crosslinking reaction with other terminal unsaturated moieties in the polypeptide chain. In certain embodiments, a "terminally unsaturated amino acid side chain" is a terminal olefinic amino acid side chain. In certain embodiments, a "terminally unsaturated amino acid side chain" is a terminal acetylenic amino acid side chain. In certain embodiments, the terminal moiety of a "terminally unsaturated amino acid side chain" is not further substituted. Terminally unsaturated amino acid side chains include, but are not limited to, side chains as depicted in Table 3.

A "peptide," "protein," "polypeptide," or "peptidic" comprises a polymer of amino acid residues linked together by peptide (amide) bonds. The term(s), as used herein, refers to proteins, polypeptides, and peptide of any size, structure, or function. Typically, a peptide or polypeptide will be at least three amino acids long. A peptide or polypeptide may refer to an individual protein or a collection of proteins. Inventive proteins preferably contain only natural amino acids, although non-natural amino acids (i.e., compounds that do not occur in nature but that can be incorporated into a polypeptide chain) and/or amino acid analogs as are known in the art may alternatively be employed. Also, one or more of the amino acids in a peptide or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A peptide or polypeptide may also be a single molecule or may be a multi-molecular complex. A peptide or polypeptide may be just a fragment of a naturally occurring protein or peptide. A peptide or polypeptide may be naturally occurring, recombinant, or synthetic, or any combination thereof.

The following definitions are more general terms used throughout the present application:

The term "subject," as used herein, refers to any animal. In certain embodiments, the subject is a mammal. In certain embodiments, the term "subject", as used herein, refers to a human (e.g., a man, a woman, or a child) of either sex at any stage of development.

The terms "administer," "administering," or "administration," as used herein refers to implanting, applying, absorbing, ingesting, injecting, or inhaling, the inventive polypeptide or compound.

The terms "treat" or "treating," as used herein, refers to partially or completely alleviating, inhibiting, ameliorating, and/or relieving the disease or condition from which the subject is suffering.

The terms "effective amount" and "therapeutically effective amount," as used herein, refer to the amount or concentration of a biologically active agent conjugated to an inventive polypeptide of the presently claimed invention, or amount or concentration of an inventive polypeptide, that, when administered to a subject, is effective to at least partially treat a condition from which the subject is suffering.

As used herein, when two entities are "associated with" one another they are linked by a direct or indirect covalent or non-covalent interaction. In certain embodiments, the association is covalent and the entities are "conjugated." In other embodiments, the association is non-covalent. Non-covalent interactions include hydrogen bonding, van der Waals interactions, hydrophobic interactions, magnetic interactions, electrostatic interactions, etc. An indirect covalent interaction is when two entities are covalently associated through a linker.

As used herein, a "label" refers to a moiety that has at least one element, isotope, or functional group incorporated into the moiety which enables detection of the inventive polypeptide to which the label is attached. Labels can be directly attached (i.e., via a bond) or can be attached by a tether (such as, for example, a cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene, or any combination thereof, which can make up a tether). It will be appreciated that the label may be attached to or incorporated into the inventive polypeptide at any position.

In general, a label can fall into any one (or more) of five classes: a) a label which contains isotopic moieties, which may be radioactive or heavy isotopes, including, but not limited to, $^{2}H$, $^{3}H$, $^{13}C$, $^{14}C$, $^{15}N$, $^{31}P$, $^{32}P$, $^{35}S$, $^{67}Ga$, $^{99m}Tc$ (Tc-99m), $^{111}In$, $^{123}I$, $^{125}I$, $^{169}Yb$, and $^{186}Re$; b) a label which contains an immune moiety, which may be antibodies or antigens, which may be bound to enzymes (e.g., such as horseradish peroxidase); c) a label which is a colored, luminescent, phosphorescent, or fluorescent moieties (e.g., such as the fluorescent label fluoresceinisothiocyanat (FITC); d) a label which has one or more photo affinity moieties; and e) a label which has a ligand moiety with one or more known binding partners (such as biotin-streptavidin, FK506-FKBP, etc.).

In certain embodiments, a label comprises a radioactive isotope, preferably an isotope which emits detectable particles, such as β particles.

In certain embodiments, the label comprises a fluorescent moiety. In certain embodiments, the label is the fluorescent label fluoresceinisothiocyanat (FITC). In certain embodiments, the label comprises a ligand moiety with one or more known binding partners. In certain embodiments, the label comprises the ligand moiety biotin.

BRIEF DESCRIPTION OF THE DRAWING

Figure/depicts the Wnt/β-catenin signaling pathway [1, 2]. (a) inactive, (b) active.

FIG. 6 shows (a) phage display library with X as randomized position; (b) sequences found in picked colonies after two (entries 1-16) and three (entries 17-33) selection cycles.

FIG. 8 depicts Axin wild type sequence (amino acids 469-484) with a summary of variations found in 33 sequences (FIG. 6*b*) resulting from phage display.

FIG. 9 depicts (a) a selection of peptides synthesized in the course of optimization including $K_d$ with β-catenin (yellow boxes mark varied amino acids, charges at pH 7.5 are calculated values); (b) cell penetration assay: SW480 cells were treated with 10 μM peptide in 10% serum for 24 h; pictures were taken with confocal microscope—blue: nucleus, green: peptides.

FIG. 10 depicts (a) stapled peptide sequences with corresponding $K_d$ to β-catenin (blue boxes mark mutations meant to disrupt binding to (β-catenin, charges at pH 7.5 are calculated values); (b) inhibition of a Wnt-dependent luciferase reporter (dual-luciferase assay: signal was normalized to *Renilla* luciferase control); (c) dose-dependent effect of STAX-147 and STAX-160 in the dual-luciferase assay.

FIG. 14 depicts the chemical structures of STAX-147 and STAX-149.

DETAILED DESCRIPTION OF THE INVENTION

Provided herein are peptides targeting β-catenin that include a stabilized α-helical segment (e.g., a stapled or stitched α-helical segment). In certain embodiments, these peptides are stapled α-helical peptides. In certain embodiments, these peptides may be used to restore the ability to degrade β-catenin, e.g. in cells that have lost their ability to degrade β-catenin. Such cells include cancer cells exhibiting, for example, inactivation of the destruction complex or loss of β-catenin phosphorylation sites [2, 3]. In other embodiments, these peptides may be used to modulate cell lineage determination and/or organ/tissue/cell differentiation.

Figure 3A:
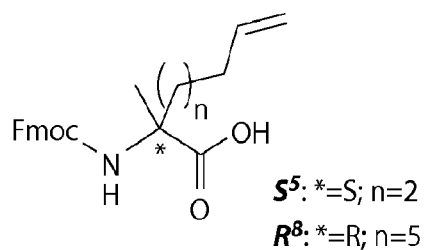
FIG. 3 depicts (a) α,α-disubstituted non-natural amino acids that are used to introduce the olefin function into a peptide sequence; (b) Ru-catalyzed metathesis used to form the olefin staple on solid support [8].
Figure 3B:
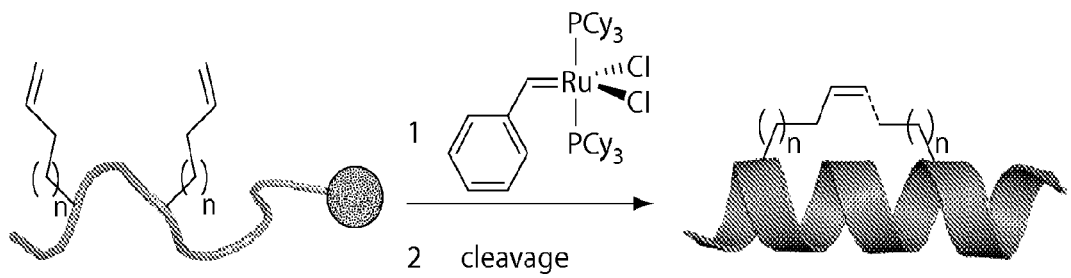

In certain embodiments, the peptides provided herein that target β-catenin comprise sequences that are derived from an α-helical segment of Axin that is known to bind to β-catenin. In certain embodiments, the peptides are modified to render the inventive peptides cell permeable. In certain embodiments, the peptides comprise non-natural amino acids containing olefin-bearing tethers (FIG. 3*a*). Such peptide can be used to generate a staple, for example, by olefin metathesis thereby increasing the helical character of the peptide (FIG. 3*b*).

In certain embodiments, the peptide comprises one or more staples to stabilize the α-helical conformation. In certain embodiments, the peptide is used to antagonize the protein-protein interaction between the transcription factor TCF and the transcriptional regulator β-catenin. In certain embodiments, the β-catenin binding polypeptide comprises an α-helical segment, wherein the polypeptide comprises the amino acid sequence:

$X_1X_2X_3X_4X_5Y_1X_6X_7X_8Y_2X_9X_{10}X_{11}X_{12}X_{13}X_{14}X_{15}$, wherein $X_1$ is selected from the group consisting of R, K, and no amino acid;

$X_2$ is selected from the group consisting of R, K, W, and no amino acid;

$X_3$ is selected from the group consisting of W, Y, and Q;

$X_4$ is selected from the group consisting of P, S, W, A, F, and L;

$X_5$ is selected from the group consisting of E, Q, R, and W;

$X_6$ is selected from the group consisting of I and L;

$X_7$ is selected from the group consisting of I and L;

$X_8$ is selected from the group consisting of D and N;

$X_9$ is selected from the group consisting of H and W;

$X_{10}$ is selected from the group consisting of V, W, L, M, F, and I;

$X_{11}$ is selected from the group consisting of Q, E, L, D, H, R, S, and V;

$X_{12}$ is selected from the group consisting of R, S, and K;

$X_{13}$ is selected from the group consisting of V, I, L, W, F, and H;

$X_{14}$ is selected from the group consisting of M, norleucine, I, L, W, F, and H;

$X_{15}$ is selected from the group consisting of R, G, P, E, H, K, Q, and no amino acid; and $Y_1$ is selected from the group S, $S^5$, $R^5$, and $Y_2$ is selected from the group E, $S^5$, and $R^5$.

In certain embodiments, the polypeptide comprises the amino acid sequence:

$X_1X_2X_3X_4X_5Y_1X_6X_7X_8Y_2X_9X_{10}X_{11}X_{12}X_{13}X_{14}X_{15}$, wherein the amino acid of $X_{1, 2, 11, 12, 15}$ is a positively charged amino acid and/or the amino acid of $X_{3, 4, 5, 6, 7, 9, 10, 13, 14}$ is a bulky, hydrophobic amino acid.

In certain embodiments, the β-catenin binding polypeptide comprises an α-helical segment, wherein the polypeptide comprises the amino acid sequence:

$X_1X_2X_3X_4X_5X_6X_7X_8X_9X_{10}X_{11}X_{12}X_{13}X_{14}X_{15}X_{16}$, wherein $X_1$ is selected from the group consisting of R, V, E, Q, T, K, W, and L;

$X_2$ is selected from the group consisting of W, S, L, N, Y, K, V, and Q;

$X_3$ is selected from the group consisting of P, L, S, W, A, and F;

$X_4$ is selected from the group consisting of E, Q, and W;

$X_5$ is S;

$X_6$ is I;

$X_7$ is L;

$X_8$ is D;

$X_9$ is selected from the group consisting of E and Q;

$X_{10}$ is H;

$X_{11}$ is selected from the group consisting of W, V, F, M, L, and I;

$X_{12}$ is selected from the group consisting of E, Q, H, D, V, and L;

$X_{13}$ is selected from the group consisting of R and K;

$X_{14}$ is selected from the group consisting of V and W;

$X_{15}$ is selected from the group consisting of M, W, F, and E; and $X_{16}$ is selected from the group consisting of R, G, P, E, and Q, with the proviso that the sequence is not the wild-type sequence from Axin, ENPESILDEHVQRVMR (SEQ ID NO: 1) (amino acids 469-484 of rat axin) or ENPESILDEHVQRVLR (SEQ ID NO: 2) (amino acids 465-480 of human axin).

In certain embodiments, the peptides of the amino acid sequence, $X_1X_2X_3X_4X_5X_6X_7X_8X_9X_{10}X_{11}X_{12}X_{13}X_{14}X_{15}X_{16}$, are modified to induce or stabilize an α-helical conformation. In certain embodiments, the modification is a peptide staple, a lactam cross-link, a disulfide cross-link, α-methylation, N-caps, or a hydrogen bond surrogate.

The invention is based, in part, on the discovery that certain alpha-helical polypeptides of Axin have the ability to penetrate cells efficiently and to bind efficiently to β-catenin, thereby providing agents that can be used to modulate Wnt pathway signalling. In certain embodiments, the inventive β-catenin targeting peptide exhibits one or more properties, such as, resistance to proteolytic cleavage, high target binding affinity, in vitro biological activity, capability of cell penetration, that may make them suitable as pharmacological or research agents. In certain embodiments, the polypeptides include a staple between two non-natural amino acids, which significantly enhances the α-helical secondary structure of the polypeptide. Generally, the staple extends across the length of one or two helical turns (i.e., about 3.4 or about 7 amino acids), and amino acids positioned at i and i+3; i and i+4; or i and i+7 may be used for chemical modification and crosslinking. In other embodiments, the amino acids positioned at i and i+5; i and i+6; or i and i+8 may be used for chemical modification and crosslinking. The inventive peptides described herein may include a more than one staple within the polypeptide sequence to further stabilize the sequence and/or facilitate the stabilization of longer polypeptide stretches (stitched peptides).

Structure of an Inventive β-Catenin Targeting Peptide

In certain embodiments, invention peptides comprise any number of amino acids. The number of amino acids can be four or more, 5, 6, 7, 8, 9, 10, 11, 12, 13, 14, 15, 16, 17, 18, 19, 20, 25, 30, 35, 40, 45, 50, 100, or more, or any number of amino acids in between 4 and 100. The peptide may comprise a number of amino acids that are the minimal number of amino acids sufficient to specifically bind or associate with β-catenin.

Recognition between a shallow β-catenin groove and an alpha-helical portion of Axin is thought to occur mainly via hydrophobic interactions. The shallow hydrophobic pocket of β-catenin is thought to be formed by Phe 253, Phe 293, and Tyr 254 (of human β-catenin). Other β-catenin residues thought to interact with Axin are Ser 250, Thr 257 and Ile 296, Trp 338 (Ying Y. et al. *Genes & Dev.* 2003. 17: 2753-2764). In addition to hydrophobic interactions, salt bridges and hydrogen bonds have also been shown to be responsible for the β-catenin/Axin interaction, e.g., Lys 292 in armadillo repeat 4 and His 260 of β-catenin armadillo repeat 3.

In certain embodiments, the peptide is of the general formula (Formula I):

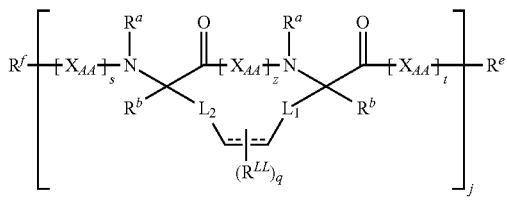

wherein each instance of $L_1$ and $L_2$ is, independently, a bond; cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene;

each instance of $R^a$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; or a suitable amino protecting group;

each instance of $R^b$ is, independently, a suitable amino acid side chain; hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; substituted or unsubstituted hydroxyl; substituted or unsubstituted thiol; substituted or unsubstituted amino; cyano; isocyano; halo; or nitro;

each instance of $R^e$ is, independently, a bond to the linker moiety, $-R^E$, $-OR^E$, $-N(R^E)_2$, or $-SR^E$, wherein each instance of $R^E$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable hydroxyl, amino, or thiol protecting group; or two $R^E$ groups of $-N(R^E)_2$ together form a substituted or unsubstituted 5- to 6-membered heterocyclic or heteroaromatic ring;

each instance of $R^f$ is, independently, a bond to the linker moiety; hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable amino protecting group; a label optionally joined by a tether, wherein the tether is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; or $R^f$ and $R^a$ of a terminal amino acid together form a substituted or unsubstituted 5- to 6-membered heterocyclic or heteroaromatic ring;

each instance of $R^{LL}$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; nitro;

or two adjacent $R^{LL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring;

each instance of $X_{AA}$ is, independently, a natural or unnatural amino acid;

each instance of z is, independently, an integer between 2 to 6;

each instance of j is, independently, an integer between 1 to 10;

each instance of s and t is, independently, an integer between 0 and 100;

each instance of q is, independently, an integer between 0 to 2; and

--------- corresponds to a single or double bond.

In certain embodiments, each instance of $[X_{AA}]_s$ is $X_1X_2X_3X_4X_5$, $[X_{AA}]_z$ is $X_6X_7X_8$, and $[X_{AA}]_t$ is $X_9X_{10}X_{11}X_{12}X_{13}X_{14}X_{15}$ of a β-catenin binding polypeptide that comprises an α-helical segment of Formula I, wherein $X_1$ is selected from the group consisting of R, K and no amino acid;

$X_2$ is selected from the group consisting of R, K, W and no amino acid;

$X_3$ is selected from the group consisting of W, Y and Q;

$X_4$ is selected from the group consisting of P, S, W, A, F and L;

$X_5$ is selected from the group consisting of E, Q, R and W;

$X_6$ is selected from the group consisting of I and L;

$X_7$ is selected from the group consisting of I and L;

$X_8$ is selected from the group consisting of D and N;

$X_9$ is selected from the group consisting of H and W;

$X_{10}$ is selected from the group consisting of V, W, L, M, F, and I;

$X_{11}$ is selected from the group consisting of Q, E, L, D, H, R, S, and V;

$X_{12}$ is selected from the group consisting of R, S, and K;

$X_{13}$ is selected from the group consisting of V, I, L, W, F, and H;

$X_{14}$ is selected from the group consisting of M, Norleucine, I, L, W, F, and H; and $X_{15}$ is selected from the group consisting of R, G, P, E, H, K, Q, and no amino acid.

In certain embodiments, the amino acid of $X_{1, 2, 11, 12, 15}$ is a positively charged amino acid and/or the amino acid of $X_{3, 4, 5, 6, 7, 9, 10, 13, 14}$ is a bulky, hydrophobic amino acid.

In certain embodiments, each instance of $[X_{AA}]_s$ is $X_1X_2X_3X_4X_5$, $[X_{AA}]_z$ is $X_6X_7X_8$, and $[X_{AA}]_t$ is $X_9X_{10}X_{11}X_{12}X_{13}X_{14}X_{15}X_{16}$, wherein $X_1$ is selected from the group consisting of R, V, E, Q, T, K, W, and L;

$X_2$ is selected from the group consisting of W, S, L, N, Y, K, V, and Q;

$X_3$ is selected from the group consisting of P, L, S, W, A, and F;

$X_4$ is selected from the group consisting of E, Q, and W;

$X_5$ is S;

$X_6$ is I;

$X_7$ is L;

$X_8$ is D;

$X_9$ is selected from the group consisting of E and Q;

$X_{10}$ is H;

$X_{11}$ is selected from the group consisting of W, V, F, M, L, and I;

$X_{12}$ is selected from the group consisting of E, Q, H, D, V, and L;

$X_{13}$ is selected from the group consisting of R and K;

$X_{14}$ is selected from the group consisting of V and W;

$X_{15}$ is selected from the group consisting of M, W, F, and E; and $X_{16}$ is selected from the group consisting of R, G, P, E, and Q, with the proviso that the sequence is not the wild-type sequence from Axin, ENPESILDEHVQRVMR (SEQ ID NO: 1) (amino acids 469-484 of rat axin) or ENPESILDEHVQRVLR (SEQ ID NO: 2) (amino acids 465-480 of human axin).

In certain embodiments, the inventive polypeptide of Formula I comprises an amino acid sequence, wherein $[X_{AA}]_s$ is selected from the group consisting of: ENPE (SEQ ID NO:3), PE, PQ, RWPQ (SEQ ID NO:4), RWPR (SEQ ID NO:5), RRWPR (SEQ ID NO:6);

$[X_{AA}]_z$ is ILD (SEQ ID NO:7); and $[X_{AA}]_t$ is selected from the group consisting of: HVQRVM (SEQ ID NO:8), HVRRVMR (SEQ ID NO:9), HVRRWMR (SEQ ID NO:10), HVRRVWR (SEQ ID NO:11), HVRRNleR (SEQ ID NO:12), HVRRRWR (SEQ ID NO:13).

In certain embodiments, the inventive polypeptides comprise an amino acid sequence selected form the group consisting of the sequences: ENPES$^5$ILDS$^5$HVQRVM (SEQ ID NO:14), PES$^5$ILDS$^5$HVQRVM (SEQ ID NO:15), PES$^5$ILDS$^5$HVRRVMR (SEQ ID NO:16), PQS$^5$ILDS$^5$HVRRVMR (SEQ ID NO:17), PQS$^5$ILDS$^5$HVRRWMR (SEQ ID NO:18), PQS$^5$ILDS$^5$HVRRVWR (SEQ ID NO:19), RWPQS$^5$ILDS$^5$HVRRVWR (SEQ ID NO:20), RRWPQS$^5$ILDS$^5$HVRRVWR (SEQ ID NO:21), RWPRS$^5$ILDS$^5$HVRRVWR (SEQ ID NO:22), RRWPRS$^5$ILDS$^5$HVRRVWR (SEQ ID NO:23), RWPQS$^5$ILDS$^5$HVRRWNleR (SEQ ID NO:24), RWPRS$^5$ILDS$^5$HVRRWNleR (SEQ ID NO:25), RWPQS$^5$ILDS$^5$HVRRRWR (SEQ ID NO:26), RWPRS$^5$ILDS$^5$HVRRRWR (SEQ ID NO:27).

In certain embodiments, wherein the invention β-catenin targeting peptide of the sequence $X_1X_2X_3X_4X_5Y_1X_6X_7X_8Y_2X_9X_{10}X_{11}X_{12}X_{13}X_{14}X_{15}$ or $X_1X_2X_3X_4X_5X_6X_7X_8X_9X_{10}X_{11}X_{12}X_{13}X_{14}X_{15}X_{16}$ is extended N-terminally and/or C-terminally and comprises multiple staples, the inventive polypeptide is of the general formula (Formula II):

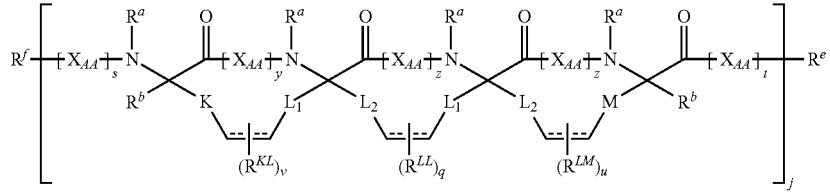

wherein each instance of K, $L_1$, $L_2$, and M, is, independently, a bond; cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene;

each instance of $R^a$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; or a suitable amino protecting group;

each instance of $R^b$ is, independently, a suitable amino acid side chain; hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; cyclic or acyclic, substituted or unsubstituted acyl; substituted or unsubstituted hydroxyl; substituted or unsubstituted thiol; substituted or unsubstituted amino; cyano; isocyano; halo; or nitro;

each instance of $R^e$ is, independently, a bond to the linker moiety, —$R^E$, —$OR^E$, —$N(R^E)_2$, or —$SR^E$, wherein each instance of $R^E$ is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable hydroxyl, amino, or thiol protecting group; or two $R^E$ groups of —$N(R^E)_2$ together form a substituted or unsubstituted 5- to 6-membered heterocyclic or heteroaromatic ring;

each instance of $R^f$ is, independently, a bond to the linker moiety; hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; a resin; a suitable amino protecting group; a label optionally joined by a tether, wherein the tether is selected from cyclic or acyclic, branched or unbranched, substituted or unsubstituted alkylene; cyclic or acyclic, branched or unbranched, substituted or unsubstituted alkenylene; cyclic or acyclic, branched or unbranched, substituted or unsubstituted alkynylene; cyclic or acyclic, branched or unbranched, substituted or unsubstituted heteroalkylene; cyclic or acyclic, branched or unbranched, substituted or unsubstituted heteroalkenylene; cyclic or acyclic, branched or unbranched, substituted or unsubstituted heteroalkynylene; substituted or unsubstituted arylene; substituted or unsubstituted heteroarylene; or substituted or unsubstituted acylene; or $R^f$ and $R^a$ together form a substituted or unsubstituted 5- to 6-membered heterocyclic or heteroaromatic ring;

each instance of $R^{KL}$, $R^{LL}$, and $R^{LM}$, is, independently, hydrogen; cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted thiol; substituted or unsubstituted amino; azido; cyano; isocyano; halo; nitro;

or two adjacent $R^{KL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring; two adjacent $R^{KL}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring; or two adjacent $R^{LM}$ groups are joined to form a substituted or unsubstituted 5- to 8-membered cycloaliphatic ring; substituted or unsubstituted 5- to 8-membered cycloheteroaliphatic ring; substituted or unsubstituted aryl ring; or substituted or unsubstituted heteroaryl ring;

each instance of $X_{AA}$ is, independently, a natural or unnatural amino acid;

each instance of y and z is, independently, an integer between 2 to 6;

each instance of j is, independently, an integer between 1 to 10;

each instance of p is, independently, an integer between 0 to 10;

each instance of s and t is, independently, an integer between 0 and 100;

each instance of u, v, and q, is, independently, an integer between 0 to 2; and

---------- corresponds to a single or double bond.

In certain embodiments, each instance of $[X_{AA}]_s$, $[X_{AA}]_y$, $[X_{AA}]_z$ and $[X_{AA}]_t$ of the β-catenin binding polypeptide comprising multiple staples of Formula II is independently derived from an amino acid sequence of axin-1, axin-2, or $TCF_4$, a random amino acid sequence or an amino acid sequence derived from a protein that is not axin-1, axin-2, or TCF4.

In certain embodiments, the inventive peptide that targets β-catenin is an alpha-helical polypeptide or is substantially alpha-helical. As used herein, the phrase "substantially alpha-helical" refers to a polypeptide adopting, on average, backbone (φ, ψ) dihedral angles in a range from about (−90°,−15° to about (−35°, −70°). Alternatively, the phrase "substantially alpha-helical" refers to a polypeptide adopting dihedral angles such that the ψ dihedral angle of one residue and the φ dihedral angle of the next residue sums, on average, about −80° to about −125°. In certain embodiments, the polypeptide adopts dihedral angles such that the ψ dihedral angle of one residue and the φ dihedral angle of the next residue sums, on average, about −100° to about −110°. In certain embodiments, the polypeptide adopts dihedral angles such that the ψ dihedral angle of one residue and the φ dihedral angle of the next residue sums, on average, about −105°. Furthermore, the phrase "substantially alpha-helical" may also refer to a polypeptide having at least 50%, 60%, 70%, 80%, 90%, or 95% of the amino acids provided in the polypeptide chain in an alpha-helical conformation, or with dihedral angles as specified herein. Confirmation of a polypeptide's alpha-helical secondary structure may be ascertained by known analytical techniques, such as x-ray crystallography, electron crystallography, fiber diffraction, fluorescence anisotropy, circular dichroism (CD), and nuclear magnetic resonance (NMR) spectroscopy.

Uses of β-Catenin Targeting Peptides

β-catenin targeting stapled peptides can be used to alter one or more characteristics of the target β-catenin. In certain embodiments, the characteristics of the β-catenin is altered in such a way that this alteration affects cell fate and/or cell behavior. In certain embodiments, changes in cell fate or cell behavior as a result of changes in one or more characteristics of the target affect the disease state of a subject, such as a mammal, for example, a human. In certain embodiments, β-catenin targeting stapled peptides can be used to treat disease. In certain embodiments β-catenin targeting stapled peptides can be used to probe or elucidate biological pathways in research. The probing of a biological pathway can be performed both in vitro such as in cell or tissue culture, or in vivo, such as in an animal, e.g., humans, mice, rats, hamsters, fish, or primates.

Figure 1:
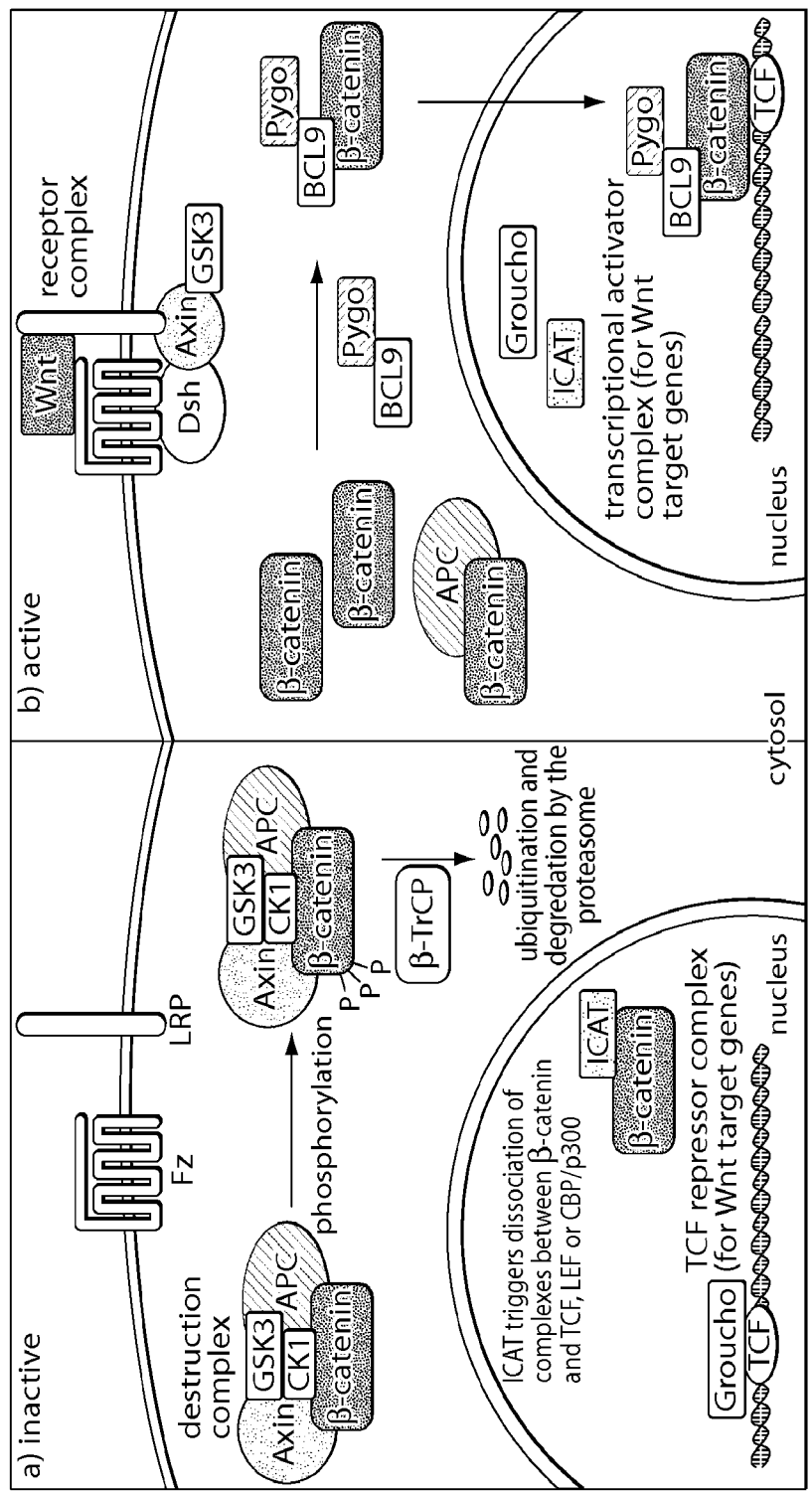
Figure 2:
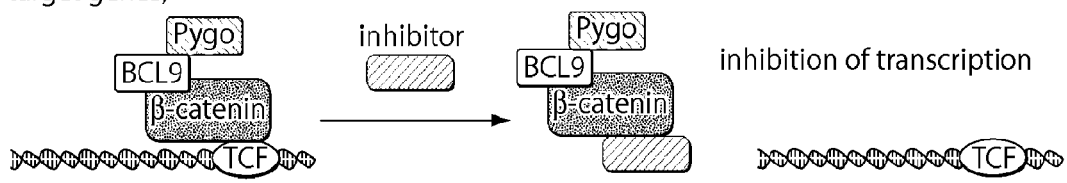
FIG. 2 shows inhibition of Wnt signaling by antagonizing TCF4/β-catenin dimerization.
Figures 4A, 4B:
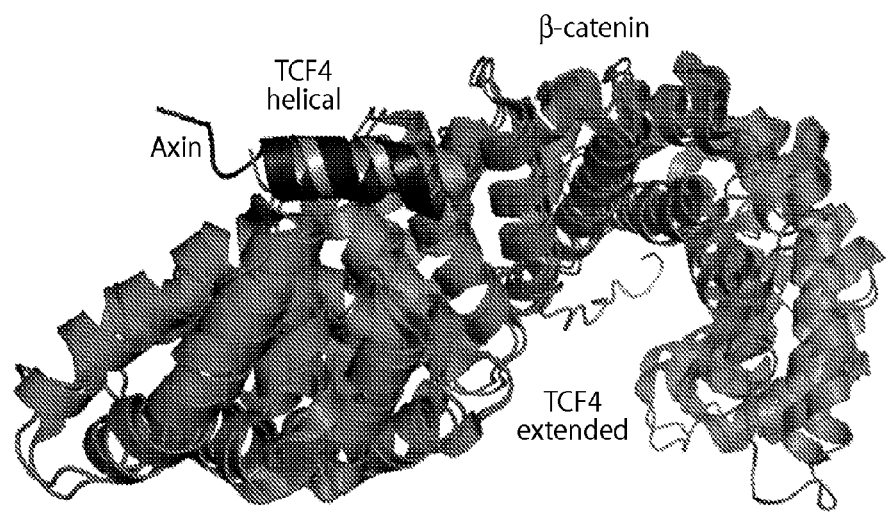
FIG. 4 depicts (a) superimposed crystal structures of TCF4 (PDB ID: 2GL7)[14] and Axin (PDB ID: 1QZ7)[15] bound to β-catenin; (b) sequences of modified peptides with NCBI accession and covered amino acids (* amino acids 29-37 were replaced by two βAla); (c) fluorescence polarization assays using FITC-labeled peptides and N-terminally GST-tagged human β-catenin (with corresponding $K_d$s).
Figures 5A, 5B:
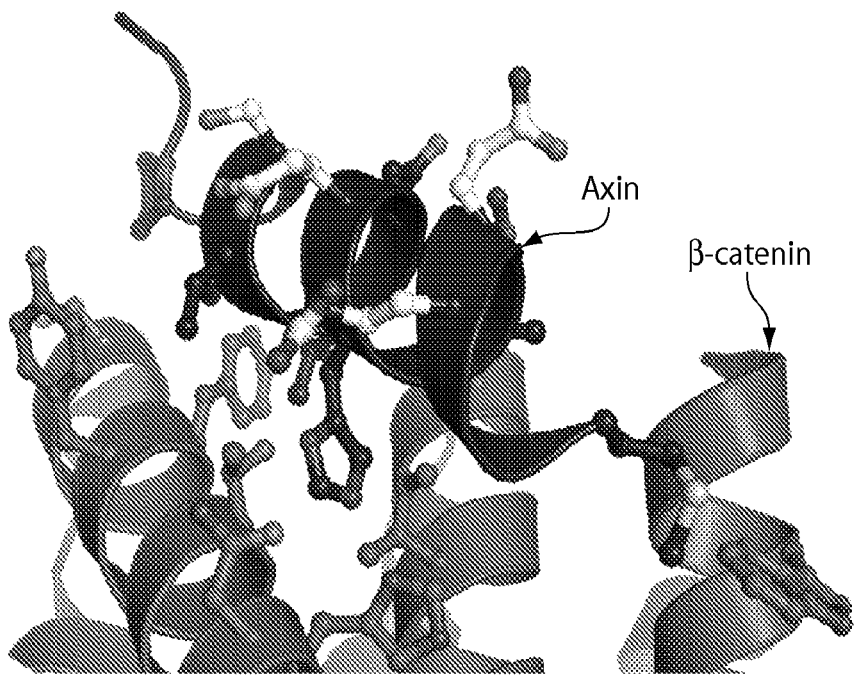
FIG. 5 shows (a) a close up of the interactions between β-catenin (red) and Axin (blue/yellow, residues 469-483, PDB ID: 1QZ7);[15]; (b) Axin (ax-WT) derived stapled peptides (STAX-1 to 3)—for $S^5$ and $R^8$ see FIG. 3; (c) circular dichroism spectra with calculated helicities; (d) Fluorescence polarization assays using FITC-labeled peptides and N-terminally GST-tagged human β-catenin (with corresponding $K_d$s).

The inventive peptides described herein, in certain embodiments, comprise amino acid sequences that bind efficiently to β-catenin. In some embodiments, these peptides may be derived at using an affinity library approach, e.g. a phage library using a portion of the O-catenin binding surface as a "bait" or selector, or may be derived from known β-catenin binding sequences, such as those derived from Axin (Ying Y. et al. *Genes & Dev.* 2003. 17: 2753-2764). One such sequence is ENPESILDEHVQRVMR (SEQ ID NO: 1) amino acids 469-384 of rat axin-1. Other homologous sequences are known in the art from other species, e.g., *Xenopus*, zebrafish, chicken, human or mouse and protein homologs, such as axin-2 (as set forth in Ying Y. et al. *Genes & Dev.* 2003. 17: 2753-2764; FIG. 1). The β-catenin targeting peptides described herein comprise sequences that are approximately 5, 6, 7, 8, 9, 10, 11, 12, 13, 14, 15, 16, 17, 18, 19, 20, 21, 22, 23, 24, 25, 26, 27, 28, 29, or 30 amino acids long. In other embodiments, the peptides are approximately 5-10, 5-20, 5-30, 5-40, 5-50, 5-60, 5-70, 5-80, 5-90, or 5-100 amino acids long. In yet other embodiments, the peptides are approximately 100, 150, 200, 250, 300, 350, 400, 450, or 500 amino acids long. In certain embodiments, these sequences comprise, when correctly folded, secondary structures, such as α-helices (Ying Y. et al. *Genes & Dev.* 2003. 17: 2753-2764; FIG. 1). Small peptides usually exhibit little or no secondary structure when excised from the stabilizing protein context thereby becoming subjected to rapid degradation by proteases under physiological conditions, displaying poor cell permeability, and exhibiting a lack of binding affinity and/or specificity resulting from conformational flexibility. The alpha-helix is one of the major structural components of peptides that has a propensity for unraveling and forming random coils. In certain embodiments, the inventive peptides comprise stapled α-helical portions that are suitable for targeting helical interaction motifs. Such peptide may be used as inhibitory peptides capable of antagonizing intracellular protein protein-interactions. In certain embodiments, the inventive peptides bind to β-catenin. In some embodiments, the peptides that bind to β-catenin can disrupt the interaction of β-catenin with T-cell factor (TCF) by specifically binding to and blocking the interaction site in β-catenin that is facilitates interaction with TCF (as depicted in FIGS. 4a and 5a). In some embodiments, the disruption of the β-catenin/TCF interaction releases the β-catenin/BCL9 (B-cell CLL/lymphoma9)/Pygo activator complex from the TCF DNA-binding factor (as depicted in FIG. 2), thereby limiting or suppressing the activation and expression of TCF/β-catenin target genes, such as, e.g., the cancer-associated genes C-myc; Cyclin D1 (cell proliferation); MDR1/PGP; COX-2; PPARδ (Inhibition of apoptosis); MMPs; uPAR,Upa; CD44; Laminin γ2; Nr-CAM (tumor progression); c-met; VEGF; WISP-1; BMP-4 (growth factors); c-jun, fra-1; ITF-2; Id2; AF17 (transcription factors); Conductin; Tcf-1; Nkd (negative feedback targets). In certain embodiments, the inventive peptides that bind to β-catenin may be derived from axin-1 or axin-2 amino acid sequence. In other embodiments, the inventive peptides that bind to β-catenin may be derived from TCF amino acid sequence. In specific embodiments, the amino acid sequence of the β-catenin targeting peptide may be derived from TCF4. In yet other embodiments, the β-catenin targeting peptide may be derived from a peptide library screening approach. In certain embodiments, the β-catenin targeting peptide may be modified further, e.g., to substitute non-natural amino acids for natural amino acids, to add or substitute positively charged amino acids for uncharged or negatively charged amino acids, or to add N-terminal or C-terminal moieties, such as tags or labels.

In certain embodiments, method of treating a disease, disorder, or condition are provided which include administering to a subject diagnosed with or having susceptibility to the disease, disorder, or condition, a therapeutically effective amount of an inventive β-catenin targeting polypeptide, or pharmaceutically acceptable form thereof. Exemplary diseases, disorders, or conditions which may be treated by administration of an inventive β-catenin targeting polypeptide comprise proliferative, neurological, immunological, endocrinologic, cardiovascular, hematologic, and inflammatory diseases, disorders. In certain embodiments, diseases, disorders, or conditions which may be treated by administration of an inventive β-catenin targeting polypeptide comprise one or more of the diseases listed in Table 4. Table 4 lists some exemplary human diseases that are caused by or associated with aberrant Wnt signaling (Luo J. *Lab Invest* 2007; 87:97-103):

| Wnt signal member | Nature of miscues | Associated diseases/phenotypes | References |
| --- | --- | --- | --- |
| APC | Loss of function | Familial adenomatous polyposis (FAP), >80% sporadic colorectal cancer (CRC) | Kinzler K W et al. *Cell* 1996; 87: 159-170; Morin P J. *Bioessays* 1999; 21: 1021-1030; Polakis P. *Curr Opin Genet Dev* 1999; 9: 15-21 |
| Axin1 | Loss of function | Hepatocellular carcinoma (HCC), sporadic medulloblastomas, CRC, esophageal squamous cell cancinomas | Clevers H. *Cell* 2006; 127: 469-480; Luu H H et al. *Curr Cancer Drug Targets* 2004; 4: 653-671; Moon R T et al. *Nat Rev Genet* 2004; 5: 691-701 |
| Axin2 | Loss of function | Familial tooth agenesis; predisposed to colorectal cancer | Yu H M. et al. *Development* 2005; 132: 1995-2005; Lammi L. et al. *Am J Hum Genet* 2004; 74: 1043-1050 |
| β-Catenin | Oncogenic mutation | CRC, HCC, melanoma, endometrial cancers, prostate cancer; bone/cartilage phenotypes | Morin P J. *Bioessays* 1999; 21: 1021-1030; Polakis P. *Curr Opin Genet Dev* 1999; 9: 15-21 |
| β-Catenin | Reduced activity | Alzheimer's disease | Moon R T. et al. *Nat Rev Genet* 2004; 5: 691-701; Mudher A et al. *Trends Neurosci* 2002; 25: 22-26; Caricasole A. et al. *Trends* |

| Wnt signal member | Nature of miscues | Associated diseases/phenotypes | References |
|---|---|---|---|
| | | | Pharmacol Sci 2003; 24: 233-238 |
| β-Catenin | Increased activity | Dupuytren skin disease | Varallo V M et al. Oncogene 2003; 22: 3680-3684 |
| Dkk1 | Over-expression | Increased osteolytic metastasis of multiple myeloma | Tian E et al. N Engl J Med 2003; 349: 2483-2494 |
| Dvl1 | Loss of function | Myocardial infarction | van Gijn M E et al. Cardiovasc Res 2002; 55: 16-24 |
| FRP1 | Over-expression | Reduced cardiac infarction | Barandon L, et al. Circulation 2003; 108: 2282-2289 |
| FRP3 | Polymorphic SNPs with reduced activity | Higher incidence of osteoarthritis in females | Loughlin J et al. Proc Natl Acad Sci USA 2004; 101: 9757-9762 |
| FRPs | Methylation | CRC | Clevers H. Cell 2006; 127: 469-480; Luu H H et al. Curr Cancer Drug Targets 2004; 4: 653-671; Moon R T et al. Nat Rev Genet 2004; 5: 691-701 |
| Fz2 | Increased expression | Cardiac hypertrophy | van Gijn M E et al. Cardiovasc Res 2002; 55: 16-24 |
| Fz3 | Polymorphic SNPs | Susceptibility to schizophrenia | Katsu T et al. Neurosci Lett 2003; 353: 53-56 |
| GSK3 | Altered activity | Schizophrenia | Kozlovsky N et al. Eur Neuropsychopharmacol 2002; 12: 13-25 |
| LRP5 | Loss of function | OPPG (osteoporosis pseudoglioma syndrome) | Gong Y et al. Cell 2001; 107: 513-523 |
| LRP5 | Gain of function | A high bone mass phenotype | Little R D et al. Am J Hum Genet 2002; 70: 11-19; Boyden L M et al. N Engl J Med 2002; 346: 1513-1521 |
| LRP5 or Fz4 | Loss of function | Familial exudative vitreoretinopathy (FEVR) | Robitaille J et al. Nat Genet 2002; 32: 326-330; Toomes C et al. Am J Hum Genet 2004; 74: 721-730; Kondo H et al. Br J Ophthalmol 2003; 87: 1291-1295 |
| Tcf4/Tcf7L2 | Transcript variants | Risk of type II diabetes | Clevers H. Cell 2006; 127: 469-480; Moon R T et al. Nat Rev Genet 2004; 5: 691-701 |
| Wnt 1 | Increased expression | Schizophrenia | Miyaoka T Schizophr Res 1999; 38: 1-6 |
| Wnt 10B | Loss of function | Associated with early-onset obesity, decreased bone mass | Hartmann C. Trends Cell Biol 2006; 16: 151-158; Christodoulides C et al. Diabetologia 2006; 49: 678-684 |
| Wnt 3 | Homozygous mutation | Tetra-amelia phenotype | Niemann S et al. Am J Hum Genet 2004; 74: 558-563 |
| Wnt 4 | Gene duplication | Mullerian-duct regression and virilization, intersex phenotype, kidney development | Jordan B K et al. Proc Natl Acad Sci USA 2003; 100: 10866-10871; Perantoni A O Semin Cell Dev Biol 2003; 14: 201-208 |
| Wnt 5B | Over-expression | Associated with Susceptibility to type II diabetes, tumor suppressor | Clevers H. Cell 2006; 127: 469-480; Moon R T et al. Nat Rev Genet 2004; 5: 691-701; Liang H et al. Cancer Cell 2003; 4: 349-360 |

In certain embodiments, inventive β-catenin targeting polypeptides are used to treat diseases associated with abberrant β-catenin protein levels and/or β-catenin activity, e.g. in cells disfunctional in degrading β-catenin and/or cells in which TCF/β-catenin target genes are ectopically expressed. In specific embodiments, such cells are cancer cells.

Current strategies targeting Wnt signaling have mostly focused on anticancer therapies (Luu et al. Curr Cancer Drug Targets 2004; 4:653-671). The β-catenin targeting peptides described herein may also be used for treatments of other diseases, such as Wnt-associated neurodegenerative diseases, degenerative bone diseases, and cardiovascular diseases.

Activated Wnt signaling plays a role in cancer development. For example, APC inactivation (Kinzler K W et al. *Cell* 1996; 87:159-170), oncogenic β-catenin mutations (Morin P J. *Bioessays* 1999; 21:1021-1030; Polakis P. *Curr Opin Genet Dev* 1999; 9:15-21) or mutations (loss of expression) of the Axin gene (Clevers H. *Cell* 2006; 127:469-480) have been found in colorectal cancers, and other cancers, such as esophageal squamous cell carcinomas, hepatocellular carcinomas, and medulloblastomas. Over-expression of Dkk1 is associated with multiple myeloma (Tian E. et al. *N Engl J Med* 2003; 349:2483-2494). Hemizygous loss of Wnt5A can lead to myeloid leukemia and B-cell lymphomas (Liang H. et al. *Cancer Cell* 2003; 4:349-360) (Luo J. *Lab Invest* 2007; 87:97-103). A germline APC mutation is the genetic cause of a hereditary cancer syndrome termed Familiar Adenomatous Polyposis (FAP) (Kinzler K W. et al. *Science* 1991; 253:661-665; Nishisho I. et al. *Science* 1991; 253:665-669), associated with colon adenomas that can progress into malignant adenocarcinoma. Constitutively active, oncogenic β-catenin transgenes may induce hair follicle tumors such as pilomatricoma-like lesions (Gat U. et al. *Cell* 1998; 95:605-614) and trichofolliculoma (Lo M C. et al. *Cell* 2004; 117: 95-106). Human sebaceous tumors may exhibit LEF1 mutations, which impair LEF1 binding to β-catenin and transcriptional activation (Takeda H. et al. *Nat. Med.* 2006; 12:395-397). The effects of Wnt pathway components on hematopoietic progenitors suggest that Wnt deregulation may contribute to hematological malignancies. For example, granulocyte-macrophage progenitors from Chronic Myelogenous Leukemia patients and blast crisis cells from patients resistant to therapy display active Wnt signaling (Jamieson C H. et al. *N. Engl. J. Med.* 2004; 351:657-667) (Clevers H. *Cell* 2006; 127:469-480).

Wnt Signaling is involved in developmental disorders. For example, a nonsense mutation in the Wnt3 gene can cause the autosomal recessive disorder Tetra-Amelia (loss of four limbs), (Niemann et al. *Am J Hum Genet.* 2004; 74:558-563), duplication of the Wnt4 gene is linked to ambiguous genitalia (Jordan et al. *Proc Natl Acad Sci USA* 2003; 100:10866-10871), and over-expression of Wnt4 or of active forms of β-catenin are associated with polycystic kidney disease (Perantoni A O, *Semin Cell Dev Biol* 2003; 14:201-208; Rodova M et al. *J Biol Chem* 2002; 277:29577-29583). Loss of function mutations of Fz4 and LRP5 are linked to familial exudative vitreoretinopathy (FEVR) (Robitaille J. et al. *Nat Genet.* 2002; 32:326-330; Toomes C et al. *Am J Hum Genet.* 2004; 74:721-730; Kondo H. et al. *Br J Ophthalmol* 2003; 87:1291-1295) (Lou J. 2007).

Wnt signaling is involved in skeletal disorders. For example, modulation of LRP5 (e.g., loss-of-function or gain-of-function mutations) are linked to the low bone mass (osteoporosis-pseudoglioma syndrome (OPPG) Gong Y. et al. *Cell* 2001; 107:513-523), or result in a high bone density, respectively (Little R D. et al. *Am J Hum Genet.* 2002; 70:11-19; Boyden L M. et al. *N Engl J Med* 2002; 346:1513-1521). Wnt10B mutations or missense variants are associated, respectively, with decrease in bone mass and human obesity (Christodoulides C. et al. *Diabetologia* 2006; 49:678-684). Axin2 loss may lead to craniosynostosis (Yu H M. et al. *Development* 2005; 132:1995-2005), and may be linked to familial tooth agenesis (Lammi L. et al. *Am J Hum Genet.* 2004; 74:1043-1050). Over-expression of Wnt4 or Wnt9A/Wnt14 enhances maturation of chondrocytes (Hartmann C. *Trends Cell Biol* 2006; 16:151-158). FRP3 polymorphs may be associated with higher incidence of osteoarthritis in females (Loughlin J. et al. *Proc Nall Acad Sci USA* 2004; 101:9757-9762) (Lou J. 2007).

Wnt signaling is associated with neuronal diseases. For example, alterations in Wnt1, Fz3, and GSK3 are all associated with schizophrenia (Miyaoka T. et al. *Schizophr Res* 1999; 38:1-6; Katsu T. et al. *Neurosci Lett* 2003; 353:53-56; Kozlovsky N. et al. *Eur Neuropsychopharmacol* 2002; 12:13-25). Attenuated β-catenin signaling is implicated in the development of Alzheimer's disease (Moon R T. et al. *Nat Rev Genet.* 2004; 5:691-701) and loss of Wnt/β-catenin function may underlie the onset and/or development of Alzheimer's disease (Mudher A et al. *Trends Neurosci* 2002; 25:22-26; Caricasole A. et al. *Trends Pharmacol Sci* 2003; 24:233-238) (Lou J. 2007).

Wnt signaling is involved in skin disorders. For example, uncontrolled Wnt signaling may lead to aggressive fibromatosis in wound healing (Cheon S S. et al. *Proc Natl Acad Sci USA* 2002; 99:6973-6978), and ectopic β-catenin signaling is detected in Dupuytren disease (Varallo V M. et al. *Oncogene* 2003; 22:3680-3684) (Lou J. 2007).

Wnt signaling is associated with cardiovascular diseases, such as infarct rupture after induction of myocardial infarction (lack of Dvl1) (Olson EN. Et al. *Genes Dev* 2003; 17:1937-1956; van Gijn M E. et al. *Cardiovasc Res* 2002; 55:16-24) (Lou J. 2007).

Wnt signals play an important role in controlling adult tissue self-renewal, e.g. in controlling cell fate of crypt progenitor cells along the crypt-villus axis (Tcf4, Dkk1) (Clevers H. *Cell* 2006; 127:469-480; Korinek V. et al. *Nat Genet* 1998; 19:379-383) regulating self-renewal of hematopoietic stem cells (β-catenin) (Reya T. et al. *Nature* 2005; 434:843-850); controlling fate determination within the T-lymphoid lineage (Tcf1 or Tcf1/Lef1) (Okamura R M. et al. *Immunity* 1998; 8:11-20); controlling the establishment of hair follicle (Lef1, β-catenin/Tcf) by regulating hair follicle precursor expansion and promoting terminal differentiation of the hair lineage (Fuchs E. et al. *Cell* 2004; 116:769-778; van Genderen C. et al. *Genes Dev* 1994; 8:2691-2703; Zhou P. et al. *Genes Dev* 1995; 9:700-713); modulating mesenchymal stem cell differentiation into osteoblastic, chondrogenic, adipogenic and/or myogenic lineages (Si W. et al. *Mol Cell Biol* 2006; 26:2955-2964; Hartmann C. *Trends Cell Biol* 2006; 16:151-158; Hartmann C. et al. *Development* 2000; 127:3141-3159; Bennett C N. et al. *Proc Natl Acad Sci USA* 2005; 102:3324-3329; Cossu G. et al. *EMBO J.* 1999; 18:6867-6872; Ross S E. et al. *Science* 2000; 289:950-953) (Lou J. 2007).

In certain embodiments, the inventive β-catenin targeting peptides may be used for regenerative medicine, such as for treating osteoporosis by modulating osteoblast differentiation and/or bone formation; they may be used as a treatment of neurodegenerative diseases, or may be used in stem cell-based therapies to modulate organ regeneration, tissue regeneration, and/or injury healing.

As used herein a proliferative disease, condition, or disorder includes, but is not limited to, cancer, hematopoietic neoplastic disorders, proliferative breast disease, proliferative disorders of the lung, proliferative disorders of the colon, proliferative disorders of the liver, and proliferative disorders of the ovary.

Examples of cancers include carcinoma, sarcoma, or metastatic disorders, breast cancer, ovarian cancer, colon cancer, lung cancer, fibrosarcoma, myosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, gastric cancer, esophageal cancer, rectal cancer, pancreatic cancer, ovarian cancer, prostate cancer, uterine cancer, cancer of the head and neck, skin cancer, brain cancer, squamous cell carcinoma, sebaceous gland carcinoma, papillary carcinoma, papillary adenocarcinoma, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular cancer, small cell lung carcinoma, non-small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, retinoblastoma, leukemia, lymphoma, or Kaposi's sarcoma.

Examples of hematopoietic neoplastic disorders include diseases involving hyperplastic/neoplastic cells of hematopoietic origin, e.g., arising from myeloid, lymphoid or erythroid lineages, or precursor cells thereof. In certain embodiments, the diseases arise from poorly differentiated acute leukemias, e.g., erythroblastic leukemia and acute megakaryoblastic leukemia. Additional exemplary myeloid disorders include, but are not limited to, acute promyeloid leukemia (APML), acute myelogenous leukemia (AML) and chronic myelogenous leukemia (CML) (reviewed in Vaickus, L. (1991) *Crit. Rev. in Oncol./Hemotol.* 11:267-97); lymphoid malignancies include, but are not limited to acute lymphoblastic leukemia (ALL) which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

Examples of proliferative breast diseases include epithelial hyperplasia, sclerosing adenosis, and small duct papillomas; tumors, e.g., stromal tumors such as fibroadenoma, phyllodes tumor, and sarcomas, and epithelial tumors such as large duct papilloma; carcinoma of the breast including in situ (noninvasive) carcinoma that includes ductal carcinoma in situ (including Paget's disease) and lobular carcinoma in situ, and invasive (infiltrating) carcinoma including, but not limited to, invasive ductal carcinoma, invasive lobular carcinoma, medullary carcinoma, colloid (mucinous) carcinoma, tubular carcinoma, and invasive papillary carcinoma, and miscellaneous malignant neoplasms. Disorders in the male breast include, but are not limited to, gynecomastia and carcinoma.

Examples of proliferative disorders of the lung include, but are not limited to, bronchogenic carcinoma, including paraneoplastic syndromes, bronchioloalveolar carcinoma, neuroendocrine tumors, such as bronchial carcinoid, miscellaneous tumors, and metastatic tumors; pathologies of the pleura, including inflammatory pleural effusions, non-inflammatory pleural effusions, pneumothorax, and pleural tumors, including solitary fibrous tumors (pleural fibroma) and malignant mesothelioma.

Examples of proliferative disorders of the colon include, but are not limited to, non-neoplastic polyps, adenomas, familial syndromes, colorectal carcinogenesis, colorectal carcinoma, and carcinoid tumors.

Examples of proliferative disorders of the liver include, but are not limited to, nodular hyperplasias, adenomas, and malignant tumors, including primary carcinoma of the liver and metastatic tumors.

Examples of proliferative disorders of the ovary include ovarian tumors such as, tumors of coelomic epithelium, serous tumors, mucinous tumors, endometeriod tumors, clear cell adenocarcinoma, cystadenofibroma, brenner tumor, surface epithelial tumors; germ cell tumors such as mature (benign) teratomas, monodermal teratomas, immature malignant teratomas, dysgerminoma, endodermal sinus tumor, choriocarcinoma; sex cord-stomal tumors such as, granulosatheca cell tumors, thecomafibromas, androblastomas, hill cell tumors, and gonadoblastoma; and metastatic tumors such as Krukenberg tumors.

Examples of neurological diseases and disorders include Alzheimer's disease, Parkinson's disease, amyotrophic lateral sclerosis (ALS) retinitis pigmentosa, spinal muscular atrophy, and various forms of cerebellar degeneration, Down's Syndrome, Dutch Type Hereditary Cerebral Hemorrhage Amyloidosis, Reactive Amyloidosis, Familial Amyloid Nephropathy with Urticaria and Deafness, Muckle-Wells Syndrome, Idiopathic Myeloma; Macroglobulinemia-Associated Myeloma, Familial Amyloid Polyneuropathy, Familial Amyloid Cardiomyopathy, Isolated Cardiac Amyloid, Systemic Senile Amyloidosis, Diabetes, Insulinoma, Isolated Atrial Amyloid, Medullary Carcinoma of the Thyroid, Familial Amyloidosis, Hereditary Cerebral Hemorrhage With Amyloidosis, Familial Amyloidotic Polyneuropathy, Scrapie, Creutzfeldt-Jacob disease, Gerstmann Straussler-Scheinker Syndrome, Bovine Spongiform Encephalitis, a Prion-mediated disease, Huntington's disease, Pick's disease, Amyotrophic Lateral Schlerosis (ALS), Parkinson's disease, and Lewy Body Disease.

Some examples of immunologic disorders include but are not limited to organ transplant rejection, arthritis, lupus, IBD, Crohn's disease, asthma, multiple sclerosis, diabetes, Graft versus host diseases, autoimmune diseases, psoriasis, rheumatoid arthritis, etc.

Examples of cardiovascular disorders include atherosclerosis, myocardial infarction, stroke, thrombosis, aneurism, heart failure, ischemic heart disease, angina pectoris, sudden cardiac death, hypertensive heart disease; non-coronary vessel disease, such as arteriolosclerosis, small vessel disease, nephropathy, hypertriglyceridemia, hypercholesterolemia, hyperlipidemia, xanthomatosis, asthma, hypertension, emphysema, and chronic pulmonary disease.

The inventive β-catenin targeting polypeptides or pharmacutical compositions thereof may serve to treat any the above-described diseases, disorders, or conditions.

Pharmaceutical Compositions

The present invention provides pharmaceutical compositions comprising an inventive β-catenin targeting polypeptide, or a pharmaceutically acceptable form thereof, and a pharmaceutically acceptable excipient. Such pharmaceutical compositions may optionally comprise one or more additional biologically active substances. In accordance with some embodiments, a method of administering a pharmaceutical composition comprising inventive compositions to a subject in need thereof is provided. In some embodiments, inventive compositions are administered to humans. For the purposes of the present invention, the phrase "active ingredient" generally refers to an inventive β-catenin targeting polypeptide, as described herein.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with merely ordinary, if any, experimentation. Subjects to which administration of the pharmaceutical compositions of the invention is contemplated include, but are not limited to, humans and/or other primates; mammals, including commercially relevant mammals such as cattle, pigs, horses, sheep, cats, and/or dogs; and/or birds, including commercially relevant birds, such as chickens, ducks, geese, and/or turkeys.

The formulations of the pharmaceutical compositions described herein may be prepared by any method known or hereafter developed in the art of pharmacology. In general, such preparatory methods include the step of bringing the active ingredient into association with a excipient and/or one or more other accessory ingredients, and then, if necessary and/or desirable, shaping and/or packaging the product into a desired single- or multi-dose unit.

A pharmaceutical composition of the invention may be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

The relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutical formulations of the present invention may additionally comprise a pharmaceutically acceptable excipient, which, as used herein, includes any and all solvents, dispersion media, diluents, or other liquid vehicles, dispersion or suspension aids, surface active agents, isotonic agents, thickening or emulsifying agents, preservatives, solid binders, lubricants and the like, as suited to the particular dosage form desired. *Remington's The Science and Practice of Pharmacy*, 21$^{st}$ Edition, A. R. Gennaro, (Lippincott, Williams & Wilkins, Baltimore, Md., 2006) discloses various excipients used in formulating pharmaceutical compositions and known techniques for the preparation thereof. Except insofar as any conventional excipient medium is incompatible with a substance or its derivatives, such as by producing any undesirable biological effect or otherwise interacting in a deleterious manner with any other component(s) of the pharmaceutical composition, its use is contemplated to be within the scope of this invention.

In some embodiments, the pharmaceutically acceptable excipient is at least 95%, 96%, 97%, 98%, 99%, or 100% pure. In some embodiments, the excipient is approved for use in humans and for veterinary use. In some embodiments, the excipient is approved by United States Food and Drug Administration. In some embodiments, the excipient is pharmaceutical grade. In some embodiments, the excipient meets the standards of the United States Pharmacopoeia (USP), the European Pharmacopoeia (EP), the British Pharmacopoeia, and/or the International Pharmacopoeia.

Pharmaceutically acceptable excipients used in the manufacture of pharmaceutical compositions include, but are not limited to, inert diluents, dispersing and/or granulating agents, surface active agents and/or emulsifiers, disintegrating agents, binding agents, preservatives, buffering agents, lubricating agents, and/or oils. Such excipients may optionally be included in the inventive formulations. Excipients such as cocoa butter and suppository waxes, coloring agents, coating agents, sweetening, flavoring, and perfuming agents can be present in the composition, according to the judgment of the formulator.

Exemplary diluents include, but are not limited to, calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and combinations thereof.

Exemplary granulating and/or dispersing agents include, but are not limited to, potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked polyvinylpyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and combinations thereof.

Exemplary surface active agents and/or emulsifiers include, but are not limited to, natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters {e.g., polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g., polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g., polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include, but are not limited to, starch (e.g., cornstarch and starch paste); gelatin; sugars (e.g., sucrose, glucose, dextrose, dextrin, molasses, lactose, lactitol, mannitol); natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, polyvinylpyrrolidone), magnesium aluminum silicate (Veegum), and larch arabogalactan); alginates; polyethylene oxide; polyethylene glycol; inorganic calcium salts; silicic acid; polymethacrylates; waxes; water; alcohol; and combinations thereof.

Exemplary preservatives may include antioxidants, chelating agents, antimicrobial preservatives, antifungal preservatives, alcohol preservatives, acidic preservatives, and other preservatives. Exemplary antioxidants include, but are not limited to, alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite. Exemplary chelating agents include ethylenediaminetetraacetic acid (EDTA), citric acid monohydrate, disodium edetate, dipotassium edetate, edetic acid, fumaric acid, malic acid, phosphoric acid, sodium edetate, tartaric acid, and trisodium edetate. Exemplary antimicrobial preservatives include, but are not limited to, benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal. Exemplary antifungal preservatives include, but are not limited to, butyl paraben, methyl paraben, ethyl paraben, propyl paraben, benzoic acid, hydroxybenzoic acid, potassium benzoate, potassium sorbate, sodium benzoate, sodium propionate, and sorbic acid. Exemplary alcohol preservatives include, but are not limited to, ethanol, polyethylene glycol, phenol, phenolic compounds, bisphenol, chlorobutanol, hydroxybenzoate, and phenylethyl alcohol. Exemplary acidic preservatives include, but are not limited to, vitamin A, vitamin C, vitamin E, betacarotene, citric acid, acetic acid, dehydroacetic acid, ascorbic acid, sorbic acid, and phytic acid. Other preservatives include, but are not limited to, tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include, but are not limited to, citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and combinations thereof.

Exemplary lubricating agents include, but are not limited to, magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and combinations thereof.

Exemplary oils include, but are not limited to, almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include, but are not limited to, pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as polyethoxylated castor oil (e.g. CREMOPHOR™), alcohols, oils, modified oils, glycols, polysorbates, cyclodextrins, polymers, and combinations thereof.

Injectable preparations, for example, sterile injectable aqueous or oleaginous suspensions may be formulated according to the known art using suitable dispersing or wetting agents and suspending agents. The sterile injectable preparation may be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients, such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type may be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type may be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient may be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a conjugate of this invention may include ointments, pastes, creams, lotions, gels, powders, solutions, sprays, inhalants and/or patches. Generally, the active component is admixed under sterile conditions with a pharmaceutically acceptable excipient and/or any needed preservatives and/or buffers as may be required. Additionally, the present invention contemplates the use of transdermal patches, which often have the added advantage of providing controlled delivery of an active ingredient to the body. Such dosage forms may be prepared, for example, by dissolving and/or dispensing the active ingredient in the proper medium. Alternatively or additionally, the rate may be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions may be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes may be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant may be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations may be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered in the manner in which snuff is taken, i.e., by rapid inhalation through the nasal passage from a container of the powder held close to the nares.

Formulations suitable for nasal administration may, for example, comprise from about as little as 0.1% (w/w) and as much as 100% (w/w) of the active ingredient, and may comprise one or more of the additional ingredients described herein. A pharmaceutical composition of the invention may be prepared, packaged, and/or sold in a formulation suitable for buccal administration. Such formulations may, for example, be in the form of tablets and/or lozenges made using conventional methods, and may, for example, 0.1 to 20% (w/w) active ingredient, the balance comprising an orally dissolvable and/or degradable composition and, optionally, one or more of the additional ingredients described herein. Alternately, formulations suitable for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention may be prepared, packaged, and/or sold in a formulation suitable for ophthalmic administration. Such formulations may, for example, be in the form of eye drops including, for example, a 0.1/1.0% (w/w) solution and/or suspension of the active ingredient in an aqueous or oily liquid excipient. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

General considerations in the formulation and/or manufacture of pharmaceutical agents may be found, for example, in *Remington: The Science and Practice of Pharmacy* $21^{st}$ ed., Lippincott Williams & Wilkins, 2005.

Administration

In some embodiments, a therapeutically effective amount of an inventive pharmaceutical composition is delivered to a patient and/or organism prior to, simultaneously with, and/or after diagnosis with a disease, disorder, and/or condition. In some embodiments, a therapeutic amount of an inventive composition is delivered to a patient and/or organism prior to, simultaneously with, and/or after onset of symptoms of a disease, disorder, and/or condition. In some embodiments, the amount of inventive conjugate is sufficient to treat, alleviate, ameliorate, relieve, delay onset of, inhibit progression of, reduce severity of, and/or reduce incidence of one or more symptoms or features of the disease, disorder, and/or condition.

The compositions, according to the method of the present invention, may be administered using any amount and any route of administration effective for treatment. The exact amount required will vary from subject to subject, depending on the species, age, and general condition of the subject, the severity of the infection, the particular composition, its mode of administration, its mode of activity, and the like. The compositions of the invention are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disorder being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The pharmaceutical compositions of the present invention may be administered by any route. In some embodiments, the pharmaceutical compositions of the present invention are administered variety of routes, including oral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, enteral, sublingual; by intratracheal instillation, bronchial instillation, and/or inhalation; and/or as an oral spray, nasal spray, and/or aerosol. Specifically contemplated routes are systemic intravenous injection, regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration), etc. At present the oral and/or nasal spray and/or aerosol route is most commonly used to deliver therapeutic agents directly to the lungs and/or respiratory system. However, the invention encompasses the delivery of the inventive pharmaceutical composition by any appropriate route taking into consideration likely advances in the sciences of drug delivery.

In certain embodiments, the β-catenin targeting polypeptides of the invention may be administered at dosage levels sufficient to deliver from about 0.001 mg/kg to about 100 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, of subject body weight per day, one or more times a day, to obtain the desired therapeutic effect. The desired dosage may be delivered three times a day, two times a day, once a day, every other day, every third day, every week, every two weeks, every three weeks, or every four weeks. In certain embodiments, the desired dosage may be delivered using multiple administrations (e.g., two, three, four, five, six, seven, eight, nine, ten, eleven, twelve, thirteen, fourteen, or more administrations).

It will be appreciated that inventive β-catenin targeting polypeptides and pharmaceutical compositions of the present invention can be employed in combination therapies. The particular combination of therapies (therapeutics or procedures) to employ in a combination regimen will take into account compatibility of the desired therapeutics and/or procedures and the desired therapeutic effect to be achieved. It will be appreciated that the therapies employed may achieve a desired effect for the same purpose (for example, an inventive conjugate useful for detecting tumors may be administered concurrently with another agent useful for detecting tumors), or they may achieve different effects (e.g., control of any adverse effects).

Pharmaceutical compositions of the present invention may be administered either alone or in combination with one or more other therapeutic agents. By "in combination with," it is not intended to imply that the agents must be administered at the same time and/or formulated for delivery together, although these methods of delivery are within the scope of the invention. The compositions can be administered concurrently with, prior to, or subsequent to, one or more other desired therapeutics or medical procedures. In general, each agent will be administered at a dose and/or on a time schedule determined for that agent. Additionally, the invention encompasses the delivery of the inventive pharmaceutical compositions in combination with agents that may improve their bioavailability, reduce and/or modify their metabolism, inhibit their excretion, and/or modify their distribution within the body.

The particular combination of therapies (therapeutics and/or procedures) to employ in a combination regimen will take into account compatibility of the desired therapeutics and/or procedures and/or the desired therapeutic effect to be achieved. It will be appreciated that the therapies employed may achieve a desired effect for the same disorder (for example, an inventive polypeptide may be administered concurrently with another biologically active agent used to treat the same disorder), and/or they may achieve different effects (e.g., control of any adverse effects). In some embodiments, polypeptides of the invention are administered with a second biologically active agent that is approved by the U.S. Food and Drug Administration.

In will further be appreciated that biologically active agents utilized in this combination may be administered together in a single composition or administered separately in different compositions.

In general, it is expected that biologically active agents utilized in combination be utilized at levels that do not exceed the levels at which they are utilized individually. In some embodiments, the levels utilized in combination will be lower than those utilized individually.

In some embodiments, inventive pharmaceutical compositions may be administered in combination with any biologically active agent or therapeutic regimen that is useful to treat, alleviate, ameliorate, relieve, delay onset of, inhibit progression of, reduce severity of, and/or reduce incidence of one or more symptoms or features of cancer. For example, inventive compositions may be administered in combination with traditional cancer therapies including, but not limited to, surgery, chemotherapy, radiation therapy, hormonal therapy, immunotherapy, complementary or alternative therapy, and any combination of these therapies.

The inventive β-catenin targeting peptides may be used for treatments of any of the diseases described herein, either as single agents or in combination with other agents, that may target additional aspects of the Wnt signaling pathway. For example, Wnt ligands may be targeted by antisense molecules, RNAi-based strategy, and neutralizing antibodies (Luu H H. et al. *Curr Cancer Drug Targets* 2004; 4:653-671). Wnt signaling antagonists, such as FRP and Dkk (e.g., Dkk3), may be used as inhibitors of Wnt signaling in cancer therapy (Tsuji T. et al. *Biochem Biophys Res Commun* 2001; 289:257-263; Hoang B H. et al. *Cancer Res* 2004; 64:2734-2739). Hepatocellular or colorectal cancers may be targeted by wild-type Axinl-induced apoptosis (Satoh S. et al. *Nat Genet.* 2000; 24:245-250). β-catenin may be directly targeted, e.g. by antisense, RNA interference, and/or protein knockdown strategies (Luu H H. et al. 2004; Verma U N. et al. *Clin Cancer Res* 2003; 9:1291-1300). Alternative strategies may involve the acceleration of the turnover rate of oncogenic β-catenin through enhanced recruitment of the cellular SCF ubiquitination machinery for ubiquitination and degradation, e.g. utilizing the expression of chimeric F-box fusion proteins (Cong F. et al. *BMC Mol Biol* 2003; 4:10; Su Y. et al. *Proc Natl Acad Sci USA* 2003; 100:12729-12734; Liu J. et al. *Biochem Biophys Res Commun* 2004; 313:1023-1029). Conditionally replication-competent oncolytic adenoviral vectors that only target tumor cells with aberrantly high β-catenin/Tcf activity may also be used (Luu H H. et al. 2004). It has been shown that tyrosine kinase inhibitors, such as STI-571/Gleevec, down-regulate β-catenin signaling (Zhou L. et al. *Cancer Lett* 2003; 193:161-170; Torrance C J. et al. *Nat Med* 2000; 6:1024-1028). In addition, retinoic acids have been shown to inhibit β-catenin/Tcf activity (Luu H H. et al. 2004) (Lou J. 2007).

Some of the known β-catenin target genes related to cancer are: C-myc; Cyclin D1 (cell proliferation); MDR1/PGP; COX-2; PPARδ (Inhibition of apoptosis); MMPs; uPAR, Upa; CD44; Laminin γ2; Nr-CAM (tumor progression); c-met; VEGF; WISP-1; BMP-4 (growth factors); c-jun, fra-1; ITF-2; Id2; AF17 (transcription factors); Conductin; Tcf-1; Nkd (negative feedback targets). Combination therapies involving the inventive peptides described herein, may include modulation of one or more of β-catenin target genes.

Wnt signaling pathways exhibit cross-talk to other major signaling pathways. This cross-talk can result in disease or can be implemented in disease progression. In certain embodiments, the inventive peptides described herein are used in combination with other agents (e.g., small-molecule compounds and/or human neutralizing antibodies) in combination therapy, for example to increase the efficacy of cancer treatment.

One such example is Wnt and FGF signaling pathways that cross-talk during a variety of cellular processes, such as human colorectal carcinogenesis, Ebb 2A-Pox-induced leukemogenesis, early embryogenesis, body-axis formation, limb-bud formation, and neurogenesis. Coactivation of WNT and FGF signaling pathways in tumors leads to more malignant phenotypes (Katoh et al. Cancer Biol Ther. 2006 5(9): 1059-64.

Another example is transforming growth factor-beta (TGFbeta) and Wnt signaling molecules that represent two distinct families of secreted molecules each of which utilizes different signaling pathways to elicit their biological effects, and mutations in components of both pathways have been described in human cancers, including colorectal carcinomas. Several studies have demonstrated that TGFbeta and Wnt ligands can cooperate to regulate differentiation and cell fate determination by controlling gene expression patterns and appear to cooperate in promoting tumorigenesis (Attisano L et al. Cancer Metastasis Rev. 2004, 23(1-2):53-61).

Other disease-related cross-talks between the Wnt pathway and other major pathway (e.g., EGF/MAPK pathway, Hedgehog (Hh) pathway in gastric cancer) are known in the art and described, for example in Korcsmáros T. et al. Bioinformatics (2010) 26(16): 2042-2050, SignaLink.org, and way2goal.com/crosstalk/.

Other developmentally relevant cross-talks have also been identified, e.g., studies have shown an Id-1 mediated cross-talk of Wnt signaling and bone morphogenetic protein 2 (BMP-2) in osteoblast differentiation (Nakashima A. et al. J. Biol. Chem., 2005 280:37660-68).

In some embodiments, inventive compositions are administered in combination with one or more chemotherapeutic agents. A chemotherapeutic agent may be, for instance, methotrexate, vincristine, adriamycin, cisplatin, non-sugar containing chloroethylnitrosoureas, 5-fluorouracil, mitomycin C, bleomycin, doxorubicin, dacarbazine, taxol, fragyline, Meglamine GLA, valrubicin, carmustaine and poliferposan, MMI270, BAY 12-9566, RAS farnesyl transferase inhibitor, farnesyl transferase inhibitor, MMP, MTA/LY231514, LY264618/Lometexol, Glamolec, CI-994, TNP-470, Hycamtin/Topotecan, PKC412, Valspodar/PSC833, Novantrone/Mitroxantrone, Metaret/Suramin, Batimastat, E7070, BCH-4556, CS-682, 9-AC, AG3340, AG3433, Incel/VX-710, VX-853, ZD0101, IS1641, ODN 698, TA 2516/Marmistat, BB2516/Marmistat, CDP 845, D2163, PD183805, DX8951f, Lemonal DP 2202, FK 317, Picibanil/OK-432, AD 32/Valrubicin, Metastron/strontium derivative, Temodal/Temozolomide, Evacet/liposomal doxorubicin, Yewtaxan/Paclitaxel, Taxol/Paclitaxel, Xeload/Capecitabine, Furtulon/Doxifluridine, Cyclopax/oral paclitaxel, Oral Taxoid, SPU-077/Cisplatin, HMR 1275/Flavopiridol, CP-358 (774)/EGFR, CP-609 (754)/RAS oncogene inhibitor, BMS-182751/oral platinum, UFT(Tegafur/Uracil), Ergamisol/Levamisole, Eniluracil/776C85/5FU enhancer, Campto/Levamisole, Camptosar/Irinotecan, Tumodex/Ralitrexed, Leustatin/Cladribine, Paxex/Paclitaxel, Doxil/liposomal doxorubicin, Caelyx/liposomal doxorubicin, Fludara/Fludarabine, Pharmarubicin/Epirubicin, DepoCyt, ZD1839, LU 79553/Bis-Naphtalimide, LU 103793/Dolastain, Caetyx/liposomal doxorubicin, Gemzar/Gemcitabine, ZD 0473/Anormed, YM 116, iodine seeds, CDK4 and CDK2 inhibitors, PARP inhibitors, D4809/Dexifosamide, Ifes/Mesnex/Ifosamide, Vumon/Teniposide, Paraplatin/Carboplatin, Plantinol/cisplatin, Vepeside/Etoposide, ZD 9331, Taxotere/Docetaxel, prodrug of guanine arabinoside, Taxane Analog, nitrosoureas, alkylating agents such as melphelan and cyclophosphamide, Aminoglutethimide, Asparaginase, Busulfan, Carboplatin, Chlorombucil, Cytarabine HCl, Dactinomycin, Daunorubicin HCl, Estramustine phosphate sodium, Etoposide (VP16-213), Floxuridine, Fluorouracil (5-FU), Flutamide, Hydroxyurea (hydroxycarbamide), Ifosamide, Interferon Alfa-2a, Alfa-2b, Leuprolide acetate (LHRH-releasing factor analogue), Lomustine (CCNU), Mechlorethamine HCl (nitrogen mustard), Mercaptopurine, Mesna, Mitotane (o.p'-DDD), Mitoxantrone HCl, Octreotide, Plicamycin, Procarbazine HCl, Streptozocin, Tamoxifen citrate, Thioguanine, Thiotepa, Vinblastine sulfate, Amsacrine (m-AMSA), Azacitidine, Erthropoietin, Hexamethylmelamine (HMM), Interleukin 2, Mitoguazone (methyl-GAG; methyl glyoxal bis-guanylhydrazone; MGBG), Pentostatin (2'-deoxycoformycin), Semustine (methyl-CCNU), Teniposide (VM-26) or Vindesine sulfate, signal transduction inhibitors (such as MEK, BRAF, AKT, her2, mTOR, and PI3K inhibitors), but it is not so limited.

In some embodiments, inventive compositions are administered in combination with one or more immunotherapeutic agents. An immunotherapeutic agent may be, for instance, Ributaxin, Herceptin, Quadramet, Panorex, IDEC-Y2B8, BEC2, C225, Oncolym, SMART M195, ATRAGEN, Ovarex, Bexxar, LDP-03, ior t6, MDX-210, MDX-11, MDX-22, OV103, 3622W94, anti-VEGF, Zenapax, MDX-220, MDX-447, MELIMMUNE-2, MELIMMUNE-1, CEACIDE, Pretarget, NovoMAb-G2, TNT, Gliomab-H, GNI-250, EMD-72000, LymphoCide, CMA 676, Monopharm-C, 4B5, ior egf.r3, ior c5, BABS, anti-FLK-2, MDX-260, ANA Ab, SMART 1D10 Ab, SMART ABL 364 Ab or ImmuRAIT-CEA, but it is not so limited.

A therapeutic substance may also be any of the following agents: adrenergic agent; adrenocortical steroid; adrenocortical suppressant; agents for treating cognition, antiplatelets, aldosterone antagonist; amino acid; anabolic; analeptic; analgesic; anesthetic; anorectic; anti-acne agent; anti-adrenergic; anti-allergic; anti-Alzheimer's; anti-amebic; anti-anemic; anti-anginal; anti-arthritic; anti-asthmatic; anti-atherosclerotic; antibacterial; anticholinergic; anticoagulant; anticonvulsant; antidepressant; antidiabetic; antidiarrheal; antidiuretic; anti-emetic; anti-epileptic; antifibrinolytic; antifungal; antihemorrhagic; antihistamine; antihyperlipidemia; antihypertensive; antihypotensive; anti-infective; anti-inflammatory; antimicrobial; antimigraine; antimitotic; antimycotic, antinauseant, antineoplastic, antineutropenic, antiparasitic; antiproliferative; antipsychotic; antirheumatic; antiseborrheic; antisecretory; antispasmodic; antithrombotic; anti-ulcerative; antiviral; anxiolytics, appetite suppressant; blood glucose regulator; bone resorption inhibitor; bronchodilator; cardiovascular agent; cholinergic; COX1 inhibitors, COX2 inhibitors, direct thrombin inhibitors, depressant; diagnostic aid; diuretic; dopaminergic agent; estrogen receptor agonist; fibrinolytic; fluorescent agent; free oxygen radical scavenger; gastrointestinal motility effector; glucocorticoid; GPIIbIIIa antagonists, hair growth stimulant; hemostatic; histamine H2 receptor antagonists; hormone; human growth hormone, hypocholesterolemic; hypoglycemic; hypolipidemic; hypnotics, hypotensive; imaging agent; immunological agents such as immunizing agents, immunomodulators, immunoregulators, immunostimulants, and immunosuppressants; keratolytic; LHRH agonist; mood regulator; mucolytic; mydriatic; nasal decongestant; neuromuscular blocking agent; neuroprotective; NMDA antagonist; non-hormonal sterol derivative; plasminogen activator; platelet activating factor antagonist; platelet aggregation inhibitor; proton pump inhibitors, psychotropic; radioactive agent; scabicide; sclerosing agent; sedative; sedative-hypnotic; selective adenosine Al antagonist; serotonin antagonist; serotonin inhibitor; serotonin receptor antagonist; statins, steroid; thyroid hormone; thyroid inhibitor; thyromimetic; tranquilizer; amyotrophic lateral sclerosis agent; cerebral ischemia agent; Paget's disease agent; unstable angina agent; vasoconstrictor; vasodilator; wound healing agent; xanthine oxidase inhibitor, signal transduction inhibitors, but it is not so limited.

In certain embodiments, the inventive peptides described herein can be combined with other therapies, and agents. These therapies and agents may further be combined with yet other therapies and agents. For example, antibody-based therapies can be combined with inhibitors of signal transduction to enhance efficacy of the treatment. The cytotoxic effects of Herceptin® (Trastuzumab, Genentech), which targets HER2, may be enhanced when combined with mTOR inhibitors, EGFR/HER2 inhibitors (e.g., Lapatinib, Tykerb®, GlaxoSmithKline plc). The chemotherapeutic drug fludarabine (Fludara®), may be combined with PI3K and/or mTOR inhibitors to enhance apoptosis of cancer cells, such as leukemia cells. Rapamycin may be combined with paclitaxel (Taxol®, Bristol-Myers Squibb), carboplatin, and/or vinorelbine (Navelbine®) to exert stronger effects on cancers such as cervical cancer and breast cancer. Rapamycin may be combined with the cell cycle check point kinase (ChK1) inhibitor UCN-01 (7-hydroxystaurosporine) in cancer cells that exhibit aberrantly regulated Raf/MEK/ERK, Akt, and/or JNK signal transduction pathways. Farnesyltransferase inhibitors, such as L744832 and R115777 (Zarnestra®) may also be combined with UCN-01 or with agents such as paclitaxel, docetaxel, doxorubicin, 5-fluorouracil, cisplatin, melphalan, mitoxantrone, and/or dexamethasone. PI3K inhibitors, such as PWT-458 (pegylated 17-hydroxywortmannin) can be used to modulate glioma, non-small cell lung cancer (NSCLC) and renal cell carcinoma growth and may be combined with paclitaxel and/or rapamycin (pegylated rapamycin). The PI3K inhibitor LY294002 may be combined with doxorubicin to enhance induction of apoptosis. Perifosine® (KRX-0401, Keryx Biopharmaceuticals) an alkylphospholipid that inhibits Akt, may be combined with dexamethasome, doxorubicin, melphalan (Alkeran®), and/or bortezomib (Valcade®, Millennium Pharmaceuticals) to enhance toxicity, e.g. in multiple myeloma. Akt inhibitors (e.g. A-443654, Abbott) and MEK inhibitors (e.g., CI-1040, PD 184352) may be combined with rapamycin and/or paclitaxel to enhance suppression of tumor growth. MEK inhibitors may enhance apoptosis of cancer cells when combined with arsenic trioxide, and may be combined with UCN-01. Suntinib (Sutent®, Pfizer), which inhibits VEGFR, may be used to chemo-sensitize cancer cells when combined with, e.g., cisplatin. Antibodies, such as Bevacizumab (Avastin®, Genentech/Roche), may be combined with kinase inhibitors, such as Suntinib, Sorafenib (Nexavar®,Bayer), Erlotinib (Tarceva®, an EGFR inhibitor) and also with mTOR inhibitors. Many other such combinations of agents and/or therapies are known in the art.

In some embodiments, inventive compositions are administered in combination with surgery to remove a tumor. Because complete removal of a tumor with minimal or no damage to the rest of a patient's body is typically the goal of cancer treatment, surgery is often performed to physically remove part or all of a tumor. If surgery is unable to completely remove a tumor, additional therapies (e.g., chemotherapy, radiation therapy, hormonal therapy, immunotherapy, complementary or alternative therapy) may be employed.

In some embodiments, inventive compositions are administered in combination with radiation therapy. Radiation therapy (also known as radiotherapy, X-ray therapy, or irradiation) is the use of ionizing radiation to kill cancer cells and shrink tumors. Radiation therapy may be used to treat almost any type of solid tumor, including cancers of the brain, breast, cervix, larynx, lung, pancreas, prostate, skin, stomach, uterus, or soft tissue sarcomas. Radiation can be used to treat leukemia and lymphoma. Radiation therapy can be administered externally via external beam radiotherapy (EBRT) or internally via brachytherapy. Typically, the effects of radiation therapy are localized and confined to the region being treated. Radiation therapy injures or destroys tumor cells in an area being treated (e.g., a target organ, tissue, and/or cell) by damaging their genetic material, preventing tumor cells from growing and dividing. In general, radiation therapy attempts to damage as many tumor cells as possible while limiting harm to nearby healthy tissue. Hence, it is often administered in multiple doses, allowing healthy tissue to recover between fractions.

In some embodiments, inventive compositions are administered in combination with immunotherapy. Immunotherapy is the use of immune mechanisms against tumors which can be used in various forms of cancer, such as breast cancer (e.g., trastuzumab/Herceptin®), leukemia (e.g., gemtuzumab ozogamicin/Mylotarg®), and non-Hodgkin's lymphoma (e.g., rituximab/Rituxan®). In some embodiments, immunotherapy agents are monoclonal antibodies directed against proteins that are characteristic to the cells of the cancer in question. In some embodiments, immunotherapy agents are cytokines that modulate the immune system's response. In some embodiments, immunotherapy agents may be vaccines.

In some embodiments, vaccines can be administered to prevent and/or delay the onset of cancer. In some embodiments, cancer vaccines prevent and/or delay the onset of cancer by preventing infection by oncogenic infectious agents. In some embodiments, cancer vaccines prevent and/or delay the onset of cancer by mounting an immune response against cancer-specific epitopes. To give but one example of a cancer vaccine, an experimental vaccine for HPV types 16 and 18 was shown to be 100% successful at preventing infection with these types of HPV and, thus, are able to prevent the majority of cervical cancer cases (Harper et al., 2004, *Lancet,* 364:1757).

In some embodiments, inventive compositions are administered in combination with complementary and alternative medicine treatments. Some exemplary complementary measures include, but are not limited to, botanical medicine (e.g., use of mistletoe extract combined with traditional chemotherapy for the treatment of solid tumors); acupuncture for managing chemotherapy-associated nausea and vomiting and in controlling pain associated with surgery; prayer; psychological approaches (e.g., "imaging" or meditation) to aid in pain relief or improve mood. Some exemplary alternative measures include, but are not limited to, diet and other lifestyle changes (e.g., plant-based diet, the grape diet, and the cabbage diet).

In some embodiments, inventive compositions are administered in combination with any of the traditional cancer treatments described herein, which are often associated with unpleasant, uncomfortable, and/or dangerous side effects. For example, chronic pain often results from continued tissue damage due to the cancer itself or due to the treatment (i.e., surgery, radiation, chemotherapy). Alternatively or additionally, such therapies are often associated with hair loss, nausea, vomiting, diarrhea, constipation, anemia, malnutrition, depression of immune system, infection, sepsis, hemorrhage, secondary neoplasms, cardiotoxicity, hepatotoxicity, nephrotoxicity, ototoxicity, etc. Thus, inventive compositions which are administered in combination with any of the traditional cancer treatments described herein may be also be administered in combination with any therapeutic agent or therapeutic regimen that is useful to treat, alleviate, ameliorate, relieve, delay onset of, inhibit progression of, reduce severity of, and/or reduce incidence of one or more side effects of cancer treatment. To give but a few examples, pain can be treated with opioids and/or analgesics (e.g., morphine, oxycodone, antiemetics, etc.); nausea and vomiting can be treated with 5-HT$_3$ inhibitors (e.g., dolasetron/Anzemet®, granisetron/Kytril®, ondansetron/Zofran®, palonsetron/Aloxi®) and/or substance P inhibitors (e.g., aprepitant/Emend®); immunosuppression can be treated with a blood transfusion; infection and/or sepsis can be treated with antibiotics (e.g., penicillins, tetracyclines, cephalosporins, sulfonamides, aminoglycosides, etc.); and so forth.

In some embodiments, inventive compositions may be administered and/or inventive diagnostic methods may be performed in combination with any therapeutic agent or therapeutic regimen that is useful to diagnose one or more symptoms or features of cancer (e.g., detect the presence of and/or locate a tumor). In some embodiments, inventive conjugates may be used in combination with one or more other diagnostic agents. To give but one example, conjugates used to detect tumors may be administered in combination with other agents useful in the detection of tumors. For example, inventive conjugates may be administered in combination with traditional tissue biopsy followed by immunohistochemical staining and serological tests (e.g., prostate serum antigen test). Alternatively or additionally, inventive conjugates may be administered in combination with a contrasting agent for use in computed tomography (CT) scans and/or MRI.

Preparation of Stapled β-Catenin Targeting Peptides

In certain embodiments, the β-catenin targeting stapled or stitched peptides of the invention are designed and synthesized de novo. In certain embodiments, β-catenin targeting peptides are designed de novo first without stapling or stitching of the peptides to determine optimal binding sequences to the target (e.g. (β-catenin). The resulting sequences may then be further modified to accommodate non-natural amino acids that may be used to introduce one or more staples into the peptide and/or to change the charge of the peptide (e.g. by introducing additional positively charge residues) to increase cell permeability of the peptide. One method to determine an optimal (e.g. high affinity and/or high specificity) binding sequence of amino acids is phage display. Phage display is widely used to discover ligands from large phage peptide libraries. The recombinant phages in these libraries display cloned non-phage peptides or protein domains fused to one of the phage coat proteins. Libraries of phages displaying diverse peptides may be analyzed by affinity selection, using, for example, immobilized biomolecules as selectors (e.g. a biomolecule immobilized in an ELISA well, a semiconductor surface, etc.). After exposing the library to the selector and washing away unbound phages (e.g. by washing ELISA wells), the bound phages are enriched for clones displaying selector binding peptides. Those phages are recovered by release from the selector and by propagation in fresh host cells in preparation for further rounds of selection or for analysis of individual clones. Release is typically accomplished by breaking bonds (e.g., noncovalent bonds or covalent bonds) between selector and the peptide displayed by the phage (Barbas, C. F. 2001. Phage Display: A Laboratory Manual. *CSH Laboratory Press*, Cold Spring Harbor, N.Y.).

In certain embodiments, peptides are designed that exhibit increased binding affinity to β-catenin. These peptides may compete efficiently with TCF4 for binding to β-catenin. Biased phage display libraries may be used to screen for positions and residues that support increased affinity to β-catenin. In one example, the library is based on wild type Axin sequence with four randomized positions in each primer sequence (as depicted in FIG. 6a).

In certain embodiments, the β-catenin targeting peptides comprise one or more non-natural amino acids (Tables 1 and 2). In certain embodiments, the β-catenin targeting peptides can be stapled or stitched, as described herein and in U.S. Pat. Nos. 7,192,713; 7,723,469; 7,786,072; U.S. Patent Application Publication Nos: 2010-0184645; 2010-0168388; 2010-0081611; 2009-0176964; 2009-0149630; 2006-0008848; PCT Application Publication Nos: WO 2010/011313; WO 2008/121767; WO 2008/095063; WO 2008/061192; WO 2005/044839, by crosslinking moieties to stabilize the secondary structure.

In general, the synthesis of these stabilized secondary structures involves (1) synthesizing a peptide from a selected number of natural or non-natural amino acids, wherein said peptide comprises at least two reactive moieties capable of undergoing a C—C bond forming reaction; and (2) contacting said peptide with a reagent to generate at least one crosslinker and to effect stabilization of a specific secondary structure motif (e.g., an α-helix). (Bernal et al., *J. Am. Chem. Soc.* 2007, 129, 2456-2457).

As one of ordinary skill in the art will realize, the number, stereochemistry, and type of amino acid structures (natural or non-natural) selected will depend upon the size and shape of the secondary structure to be prepared (e.g., length of an α-helix), the ability of the particular amino acids to generate a secondary structural motif that are desirable to mimic. The secondary structure to be prepared depends on the desired biological activity, that is the ability to target a biomolecule with an affinity sufficient to be specific (e.g., TCF).

It will be appreciated, that the number of crosslinking moieties is not limited to one or two, rather the number of crosslinking moieties utilized can be varied with the length of the polypeptide as desired, and as compatible with the desired structure and activity to be generated.

The synthesis of an inventive β-catenin targeting polypeptide first involves the selection of a desired sequence and number of amino acids and amino acid analogues. As one of ordinary skill in the art will realize, the number, stereochemistry, and type of amino acid structures (natural or non-natural) selected will depend upon the size of the polypeptide to be prepared, the ability of the particular amino acids to generate a desired structural motif (e.g., an alpha-helix), and any particular motifs that are desirable to mimic to generate protein domains that effectively bind to the target biomolecule.

Once the amino acids are selected, synthesis of the inventive polypeptide can be achieved using standard deprotection and coupling reactions. Formation of peptide bonds and polypeptide synthesis are techniques well-known to one skilled in the art, and encompass both solid phase and solution phase methods; see generally, Bodanszky and Bodanszky, *The Practice of Peptide Synthesis*, Springer-Verlag, Berlin, 1984; Atherton and Sheppard, *Solid Phase Peptide Synthesis: A Practical Approach*, IRL Press at Oxford University Press Oxford, England, 1989, and Stewart and Young, *Solid phase Peptide Synthesis,* 2nd edition, Pierce Chemical Company, Rockford, 1984, the entire contents of each of which are incorporated herein by reference. In both solution phase and solid phase techniques, the choice of the protecting groups must be considered, as well as the specific coupling techniques to be utilized. For a detailed discussion of peptide synthesis techniques for solution phase and solid phase reactions, see, *Bioorganic chemistry: Peptides and Proteins*, Hecht, Oxford University Press, New York: 1998, the entire contents of which are incorporated herein by reference.

In certain embodiments, the method comprises a solution phase synthesis of an inventive β-catenin targeting polypeptide. Solution phase synthesis, as mentioned above, is a well-known technique for the construction of polypeptides. An exemplary solution phase synthesis comprises the steps of: (1) providing an amino acid protected at the N-terminus with a suitable amino protecting group; (2) providing an amino acid protected at the C-terminus with a suitable carboxylic acid protecting group; (3) coupling the N-protected amino acid to the C-protected amino acid; (4) deprotecting the product of the coupling reaction; and (5) repeating steps (3) to (4) until a desired polypeptide is obtained, wherein at least two of the amino acids coupled at any of the above steps each comprise at least one terminally unsaturated amino acid side chain, and at least one α,α-disubstituted amino acid comprises two terminally unsaturated amino acid side chains. During the course of the above synthesis, various parameters can be varied, including, but not limited to placement of amino acids with terminally unsaturated side chains, stereochemistry of amino acids, terminally unsaturated side chain length and functionality, and amino acid residues utilized.

In certain embodiments, the method comprises a solid phase synthesis of an inventive β-catenin targeting polypeptide or portion thereof. Solid phase synthesis, as mentioned above, is a well-known technique for the construction of polypeptides. An exemplary solid phase synthesis comprises the steps of: (1) providing a resin-bound amino acid; (2) deprotecting the resin bound amino acid; (3) coupling an amino acid to the deprotected resin-bound amino acid; (4) repeating steps (3) until a desired peptide is obtained, wherein at least two of the amino acids coupled at any of the above steps each comprise at least one terminally unsaturated amino acid side chain, and at least one α,α-disubstituted amino acid comprises two terminally unsaturated amino acid side chains. During the course of the above synthesis, various parameters can be varied, including, but not limited to placement of amino acids with terminally unsaturated side chains, stereochemistry of amino acids, terminally unsaturated side chain length and functionality, and amino acid residues utilized.

After a desired polypeptide is synthesized using an appropriate technique, the polypeptide is contacted with a specific catalyst to promote "stapling" or "stitching" of the polypeptide. (Bernal et al., *J. Am. Chem. Soc.* 2007, 129, 2456-2457). For example, the resin-bound polypeptide may be contacted with a catalyst to promote "stapling" or "stitching," or may first be cleaved from the resin, and then contacted with a catalyst to promote "stitching."

Different amino acids have different propensities for forming different secondary structures. For example, methionine (M), alanine (A), leucine (L), glutamate (E), and lysine (K) all have especially high alpha-helix forming propensities. In contrast, proline (P) and glycine (G) are alpha-helix disruptors.

In certain embodiments, the one or more reaction steps further comprise the use of a coupling reagent. Exemplary coupling reagents include, but are not limited to, benzotriazol-1-yloxy-tris(dimethylamino)-phosphonium hexafluorophosphate (BOP), benzotriazole-1-yl-oxy-tris-pyrrolidino-phosphonium hexafluorophosphate (PyB OP), bromo-tris-pyrrolidino phosphonium hexafluorophosphate (PyBroP), 1-ethyl-3-(3-dimethyllaminopropyl) carbodiimide (EDC), N,N'-carbonyldiimidazole (CDI), 3-(diethoxyphosphoryloxy)-1,2,3-benzotriazin-4(3H)-one (DEPBT), 1-hydroxy-7-azabenzotriazole (HOAt), 1-hydroxy-7-benzotriazole (HOBt), 2-(7-aza-1H-benzotriazole-1-yl)-1,1,3,3-tetramethyluronium hexafluorophosphate (HATU), 2-(6-chloro-1H-benzotriazole-1-yl)-1,1,3,3-tetramethylaminium hexafluorophosphate (HCTU), 2-(1H-benzotriazole-1-yl)-1,1,3,3-tetramethyluronium hexafluorophosphate (HBTU), 0-(7-azabenzotriazole-1-yl)-N,N,N',N-tetramethyluronium tetrafluoroborate (TATU), 2-(1H-benzotriazole-1-yl)-1,1,3,3-tetramethyluronium tetrafluoroborate (TBTU), N,N,N',N'-tetramethyl-O-(3,4-dihydro-4-oxo-1,2,3-benzotriazin-3-yl) uranium tetrafluoroborate (TDBTU), and O—(N-succinimidyl)-1,1,3,3-tetramethyl uranium tetrafluoroborate (TSTU)).

In certain embodiments, the above reaction of step (iv) further comprises a suitable base. Suitable bases include, but are not limited to, potassium carbonate, potassium hydroxide, sodium hydroxide, tetrabutylammonium hydroxide, benzyltrimethylammonium hydroxide, triethylbenzylammonium hydroxide, 1,1,3,3-tetramethylguanidine, 1,8-diazabicyclo [5.4.0]undec-7-ene (DBU), N-methylmorpholine, diisopropylethylamine (DIPEA), tetramethylethylenediamine (TMEDA), pyridine (Py), 1,4-diazabicyclo[2.2.2]octane (DABCO), N,N-dimethylamino pyridine (DMAP), or triethylamine (NEt₃).

In certain embodiments, one or more reaction steps are carried out in a suitable medium. A suitable medium is a solvent or a solvent mixture that, in combination with the combined reacting partners and reagents, facilitates the progress of the reaction there between. A suitable solvent may solubilize one or more of the reaction components, or, alternatively, the suitable solvent may facilitate the suspension of one or more of the reaction components; see generally, *March's Advanced Organic Chemistry: Reactions, Mechanisms, and Structure*, M. B. Smith and J. March, 5th Edition, John Wiley & Sons, 2001, and *Comprehensive Organic Transformations*, R. C. Larock, 2nd Edition, John Wiley & Sons, 1999, the entire contents of each of which are incorporated herein by reference. Suitable solvents for include ethers, halogenated hydrocarbons, aromatic solvents, polar aprotic solvents, or mixtures thereof. In other embodiments, the solvent is diethyl ether, dioxane, tetrahydrofuran (THF), dichloromethane (DCM), dichloroethane (DCE), acetonitrile (ACN), chloroform, toluene, benzene, dimethylformamide (DMF), dimethylacetamide (DMA), dimethylsulfoxide (DMSO), N-methylpyrrolidinone (NMP), or mixtures thereof.

In other embodiments, one or more reaction steps are conducted at suitable temperature, such as between about 0° C. and about 100° C.

In certain embodiments, one or more reaction steps involve a catalyst. One of ordinary skill in the art will realize that a variety of catalysts can be utilized. Selection of a particular catalyst will vary with the reaction conditions utilized and the functional groups present in the particular peptide. In certain embodiments, the catalyst is a ring closing metathesis (RCM) catalyst. In certain embodiments, the RCM catalyst is a tungsten (W), molybdenum (Mo), or ruthenium (Ru) catalyst. In certain embodiments, the RCM catalyst is a ruthenuim catalyst. Suitable RCM catalysts are described in see Grubbs et al., *Acc. Chem. Res.* 1995, 28, 446-452; U.S. Pat. No. 5,811, 515; Schrock et al., *Organometallics* (1982) 1 1645; Gallivan et al., *Tetrahedron Letters* (2005) 46:2577-2580; Furstner et al., *J. Am. Chem. Soc.* (1999) 121:9453; and *Chem. Eur. J.* (2001) 7:5299; the entire contents of each of which are incorporated herein by reference.

In certain embodiments, the RCM catalyst is a Schrock catalyst, a Grubbs catalyst, a Grubbs-Hoveyda catalyst, a Blechart Catalyst; a Neolyst™ Ml; or a Furstner catalyst.

It will also be appreciated, that in addition to RCM catalysts, other reagents capable of promoting carbon-carbon bond formation can also be utilized. For example, other reactions that can be utilized, include, but are not limited to palladium coupling reactions, transition metal catalyzed cross coupling reactions, pinacol couplings (terminal aldehydes), hydrozirconation (terminal alkynes), nucleophilic addition reactions, and NHK (Nozaki-Hiyama-Kishi (Furstner et al., *J. Am. Chem. Soc.* 1996, 118, 12349)) coupling reactions. Thus, the appropriate reactive moieties are first incorporated into desired amino acids or unnatural amino acids, and then the peptide is subjected to reaction conditions to effect "stapling" or "stitching" and subsequent stabilization of a desired secondary structure.

In another aspect, the present invention provides a method of synthesizing an inventive polypeptide comprising the steps of: (1) providing a selected number of amino acids comprising (i) at least two amino acids, each comprising at least one terminally unsaturated amino acid side chain, and (ii) at least one α,α-disubstituted amino acid comprising two terminally unsaturated amino acid side chains; (2) coupling the selected number of amino acids together to generate a first peptide; and (3) treating the first peptide with a suitable catalyst to provide a stapled or stitched peptide.

In certain embodiments, divinyl amino acid as "an α,α-disubstituted amino acid comprising two terminally unsaturated amino acid side chains" is specifically excluded.

In certain embodiments, each terminally unsaturated amino acid side chain is reactive toward ring closing metathesis. In certain embodiments, the suitable catalyst is a ring metathesis catalyst. In certain embodiments, the ring closing metathesis catalyst may generate at least two cross-linked rings by the above method. Depending upon the nature of the selected amino acids and their specific location in the peptide chain, stitched peptides of the present invention may comprise at least 2, 3, 4, 5, 6, or 7, cross-links, and may comprise one or more constitutional/structural isomers (i.e., compounds with the same molecular weight but having different connectivity).

In certain embodiments, the synthetic method generates one stitched product as a preferred product. As used herein a "preferred product" refers to one constitutional isomer present as the major constituent in a mixture of isomers. In certain embodiments, a "preferred product" refers to one constitutional isomer present as a component in at least about 50%, 55%, 60%, 65%, 70%, 75%, 80%, 85%, 90%, 95%, 98%, or 99%, of an isomeric mixture.

The synthetic method may be further modified to include at least three cross-linking staples by: (1) providing a selected number of natural or unnatural amino acids, wherein said number comprises: (i) at least four amino acids, each comprising at least one terminally unsaturated amino acid side chain, and (ii) at least one α,α-disubstituted amino acid comprising two terminally unsaturated amino acid side chains; (2) coupling the selected number of amino acids together to generate a first peptide; and (3) treating the first peptide with a suitable catalyst.

Additionally, the synthetic method may be modified to include at least three cross-linking staples by: (1) providing a selected number of natural or unnatural amino acids, wherein said number comprises: (i) at least two amino acids, each comprising at least one terminally unsaturated amino acid side chain, and (ii) at least two α,α-disubstituted amino acids, each comprising two terminally unsaturated amino acid side chains; (2) coupling the selected number of amino acids together to generate a first peptide; and (3) treating the first peptide with a suitable catalyst.

The present invention contemplates any and all types of modifications in order to provide at least 2, 3, 4, 5, 6, or 7 staples into the polypeptides of the invention.

The above amino acids comprising one to two terminally unsaturated amino acid side chains are so incorporated into the polypeptide chain in order to provide proximal terminally unsaturated side chains. These proximal terminally unsaturated side chains may be in the same plane as, or same side of the polypeptide chain as, each other in any given conformation of the polypeptide. Upon treatment with a suitable catalyst, these proximal side chains react with each other via "stapling" to provide a stitched, conformationally stabilized, polypeptide. In certain embodiments, the proximal terminally unsaturated side chains are arranged such that the resulting "staple" does not interfere with the biological/therapeutic activity of the stitched polypeptide.

Additional Synthetic Modifications

After "stitching" of the polypeptide, as described above, the method may further comprise additional synthetic modification(s). Any chemical or biological modification may be made. In certain embodiments, such modifications include reduction, oxidation, and nucleophilic or electrophilic additions to a functional group (e.g., a double bond provided from a metathesis reaction) of the cross-link to provide a synthetically modified stitched polypeptide. Other modifications may include conjugation of a stitched polypeptide, or a synthetically modified stitched polypeptide, with a biologically active agent, label or diagnostic agent anywhere on the stitched polypeptide scaffold, e.g., such as at the N-terminus of the stitched polypeptide, the C-terminus of the stitched polypeptide, on an amino acid side chain of the stitched polypeptide, or at one or more modified or unmodified stitched sites (i.e., to a staple). Such modification may be useful in delivery of the peptide or biologically active agent to a cell, tissue, or organ. Such modifications may allow for targeting to a particular type of cell or tissue.

Thus, in certain embodiments, the above synthetic method further comprises: (vii) treating the polypeptide with a suitably reactive agent under suitable conditions to provide a synthetically modified stitched polypeptide.

One of ordinary skill in the art will appreciate that a wide variety of reactions, conditions, and "suitably reactive agent(s)" may be employed to promote such a transformation, therefore, a wide variety of reactions, conditions, and reactive agents are envisioned; see generally, *March's Advanced Organic Chemistry: Reactions, Mechanisms, and Structure*, M. B. Smith and J. March, 5$^{th}$ Edition, John Wiley & Sons, 2001; *Advanced Organic Chemistry, Part B: Reactions and Synthesis*, Carey and Sundberg, 3$^{rd}$ Edition, Plenum Press, New York, 1993; and *Comprehensive Organic Transformations*, R. C. Larock, 2$^{nd}$ Edition, John Wiley & Sons, 1999, the entirety of each of which is hereby incorporated herein by reference. Exemplary "suitably reactive agents" may be any agent reactive with a multiple bond (e.g., a double or triple bond). In certain embodiments, suitably reactive agents are able to react with a double bond or triple bond, for example, via a hydrogenation, osmylation, hydroxylation (mono- or di-), amination, halogenation, cycloaddition (e.g., cyclopropanation, aziridination, epoxidation), oxy-mercuration, and/or a hydroboronation reaction, to provide a functionalized single bond or double bond. As one of ordinary skill in the art will clearly recognize, these above-described transformations will introduce functionalities compatible with the particular stabilized structures and the desired biological interactions; such functionalities include, but are not limited to, hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted amino; substituted or unsubstituted thiol, halo; cyano; nitro; azido; imino; oxo; and thiooxo.

In another aspect, in certain embodiments, the method further comprises treating the polypeptide with a suitably reactive agent to provide a synthetically modified stitched polypeptide, and treating the modified stitched polypeptide with a biologically active agent to provide a modified stitched polypeptide conjugated to a biologically-active agent.

In another aspect, in certain embodiments, the above method further comprises treating the polypeptide with a suitable reagent to provide a synthetically modified stitched polypeptide, and treating the modified stitched polypeptide with a diagnostic agent to provide a modified stitched polypeptide conjugated to a diagnostic agent.

Conjugation of an agent (e.g., a label, a diagnostic agent, a biologically active agent) to the inventive polypeptide may be achieved in a variety of different ways. The agent may be covalently conjugated, directly or indirectly, to the polypeptide at the site of stapling, or to the N-terminus or the C-terminus of the polypetide chain. Alternatively, the agent may be noncovalently conjugated, directly or indirectly, to the polypeptide at the site of stapling, or to the N-terminus or the C-terminus of the polypetide chain. Indirect covalent conjugation is by means of one or more covalent bonds. Indirect noncovalent conjugation is by means of one or more noncovalent bonds. Conjugation may also be via a combination of non-covalent and covalent forces/bonds. The agent may also be conjugated through a covalent or noncovalent linking group.

Any suitable bond may be used in the conjugation of a biologically active agent and/or diagnostic agent to the inventive polypeptide present invention. Such bonds include amide linkages, ester linkages, disulfide linkages, carbon-carbon bonds, carbamate, carbonate, urea, hydrazide, and the like. In some embodiments, the bond is cleavable under physiological conditions (e.g., enzymatically cleavable, cleavable with a high or low pH, with heat, light, ultrasound, x-ray, etc.). However, in some embodiments, the bond is not cleavable.

Combinatorial Synthesis of Novel Stapled or Stitched Polypeptides

It will also be appreciated by one of ordinary skill in the art that the synthetic methods as described above can also be applied to combinatorial synthesis of stapled or stitched polypeptides. Although combinatorial synthesis techniques can be applied in solution, it is more typical that combinatorial techniques are performed on the solid phase using split-and-pool techniques. During the course of the combinatorial synthesis, various parameters can be varied, including, but not limited to, placement of amino acids with terminally unsaturated side chains, stereochemistry of amino acids, terminally unsaturated side chain length and functionality, and amino acid residues utilized.

The present invention, in one aspect, provides methods for the synthesis of libraries of stapled or stitched polypeptides, as described above, comprising (1) providing a collection of resin-bound amino acids; (2) deprotecting each of said resin bound amino acids; (3) separating said collection of deprotected resin bound amino acids into n equal portions, wherein n represents the number of different types of amino acids to be coupled; (4) coupling of each of n types of amino acids to the deprotected amino acid; (5) combining each of the n portions together; and (6) repeating steps (2)-(5) until a desired polypeptide is obtained, wherein at least two of the amino acids coupled at any of the above steps each comprise at least one terminally unsaturated amino acid side chain, and at least one α,α-disubstituted amino acid comprises two terminally unsaturated amino acid side chains. After a desired polypeptide is synthesized, the resin-bound polypeptide may be contacted with a catalyst to promote "stitching," or may first be cleaved from the resin, and then contacted with a catalyst to promote "stitching."

It will be appreciated by one of ordinary skill in the art that the libraries of compounds having stabilized secondary structures can be further diversified at specific functional moieties after the desired stabilized structures are formed. For example, free or latent amino acid functionalities may be diversified, or alternatively or additionally, free or latent functionality present on the cross-linkers may be diversified. In particularly preferred embodiments, in but one example, the hydrophilicity of stabilized structures may be increased by the introduction of hydroxyl moieties. As one of ordinary skill in the art will realize, the diversification reactions will be selected to introduce functionalities compatible with the particular stabilized structures and the desired biological interactions, and these functionalities include, but are not limited to hydrogen, cyclic or acyclic, branched or unbranched, substituted or unsubstituted aliphatic; cyclic or acyclic, branched or unbranched, substituted or unsubstituted heteroaliphatic; substituted or unsubstituted aryl; substituted or unsubstituted heteroaryl; substituted or unsubstituted acyl; substituted or unsubstituted hydroxyl; substituted or unsubstituted amino; substituted or unsubstituted thiol; halo; cyano; nitro; azido; imino; oxo; and thiooxo.

EXAMPLES

Deregulation of Wnt/β-catenin signaling is associated with several types of cancer. Especially, a reduced ability to degrade β-catenin, e.g., by the inactivation of the destruction complex or by loss of β-catenin phosphorylation sites, can be involved in the formation of cancer.[2, 3] Restoring this ability would contribute to target cancers that depend on deregulated Wnt signaling to grow. The manipulation of requisite protein-protein interactions offers a strategy to interfere with this pathway, e.g., targeting the signaling cascade downstream by inhibiting the interaction of β-catenin with TCF transcription factors (FIG. 2). This setup may allow for inhibition of Wnt signaling independent of the site of deregulation within the pathway.

Due to large interaction areas, the precise manipulation of protein-protein interactions is complicated.[6] In principle, an isolated bioactive helix of a protein could be used to interfere with such interactions. However, small peptides usually exhibit little or no helical character when excised from the stabilizing protein context, thereby losing their protease resistance and affinity to the target. It was shown that hydrocarbon-stapled α-helical peptides[7, 8] are suitable for targeting helical interaction motifs[8-13] and they have proven capable of antagonizing intracellular protein-protein interactions.[10-13] This strategy applies non-natural amino acids containing olefin-bearing tethers (FIG. 3a) to generate an all-hydrocarbon staple by ruthenium-catalyzed olefin metathesis thereby increasing the helical character of the peptide (FIG. 3b). This stapling approach was used to stabilize bioactive α-helical peptides and to antagonize the protein-protein interaction between the transcription factor TCF4 and the transcriptional regulator β-catenin.

The crystal structure can form the basis for the design of protein binding peptides as it allows the exact assignment of protein binding sites and the identification of peptide residues suitable for modification. FIG. 4a shows superimposed structures of β-catenin binding domains of TCF4 (green)[14] and Axin (blue)[15] in complex with β-catenin. The binding domain of TCF4 (green) contains an N-terminal extended region, a disordered spacer (9 amino acids; not visible in crystal structure) and a C-terminal α-helix. The α-helical binding domain of Axin (blue) shares the binding region with the α-helix of TCF4. Even though both helixes have opposite orientation (their N- and C-termini are swapped) a competition for β-catenin binding might be expected.

Figure 4C:
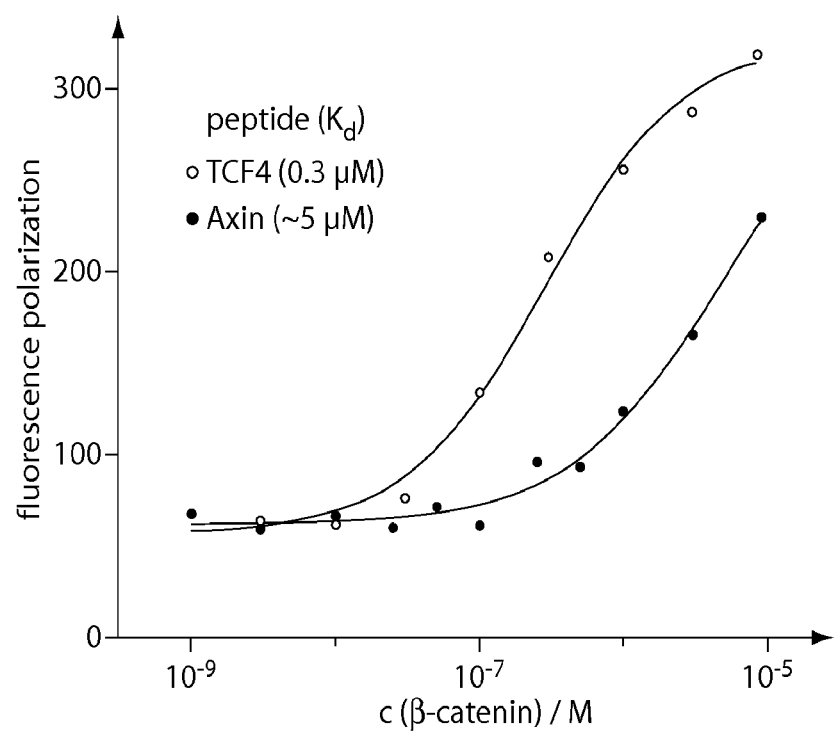

Peptide sequences derived from TCF4 and Axin were synthesized and fluorescently labeled (FIG. 4b) and the affinity of both binding domains to β-catenin was assessed. The sequence of TCF4 was modified in such a way that the loop (9 amino acids; not visible in the crystal structure) between the extended region and the α-helix was replaced by two β-alanines ((3Ala). Labeled peptides and GST-tagged human β-catenin were used in a fluorescence polarization assay enabling the determination of the stability of these peptide/13-catenin complexes (FIG. 4c). Observed Kds for TCF4 and Axin derived peptides are 0.3 µM and ~5 µM, respectively. Initial attempts to optimize the TCF4 sequence were dismissed since the presence of the extended region, which might hinder cell permeability and decrease proteolytic stability, was determined to be a prerequisite for affine binding of β-catenin. Therefore, the Axin derivative was considered to be the most promising candidate for the hydrocarbon stapling approach. It combines a relatively short and helical peptide sequence (15 amino acids) with moderate binding of β-catenin ($K_d$ of ~5 µM).

Figure 5C:
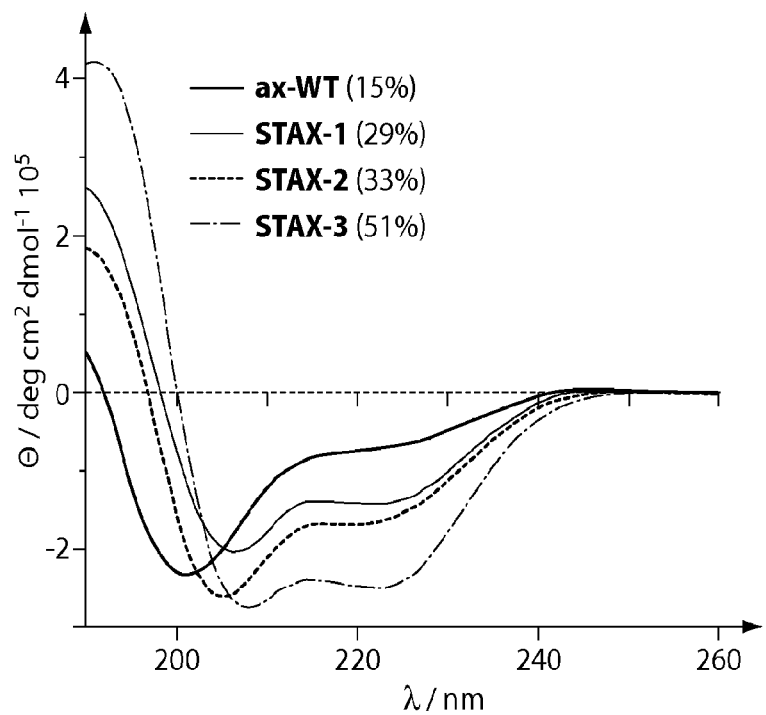
Figure 5D:
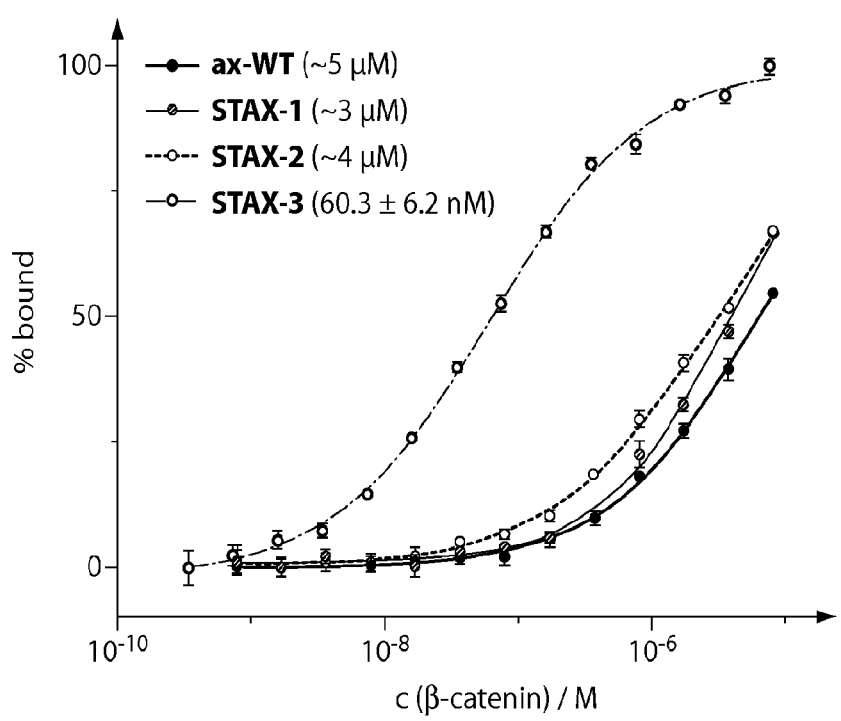

Based on the crystal structure of the Axin/β-catenin complex there are four residues (yellow, FIG. 5a) that are not involved in β-catenin binding[15] and should be suitable for modification without affecting binding. Taking into consideration that only i,i+4 (one helix turn) and i,i+7 5 (two helix turns) positioning of modified residues allows sufficient cross-linking[8] three hydrocarbon stapled sequences (STAX-1, 2 and 3, FIG. 5b) were designed. Circular dichroism spectra of the fluorescently labeled peptides were recorded allowing the calculation of helicities (FIG. 5c). In addition, a fluorescence polarization assay revealed affinities to β-catenin (FIG. 5d). For all stapled peptides (STAX-1, 2 and 3) helicity as well as affinity increased compared to the wild type sequence (ax-WT). i,i+4 Stapled STAX-3 showed the highest increase in both helicity (51%, 3.4 fold) and affinity (60.3±6.2 nM, 80 fold). Therefore, STAX-3 was chosen as starting point for further optimizations.

The following attempts aimed at a modification of the peptide sequence in order to achieve increased binding affinity to β-catenin, allowing the peptide to compete with TCF4 for binding. A biased library in a phage display was used to screen for positions and residues that support increased affinity to β-catenin. The library (FIG. 6a) is based on wild type Axin sequence with four randomized positions in each primer sequence.

Figures 7A, 7B:
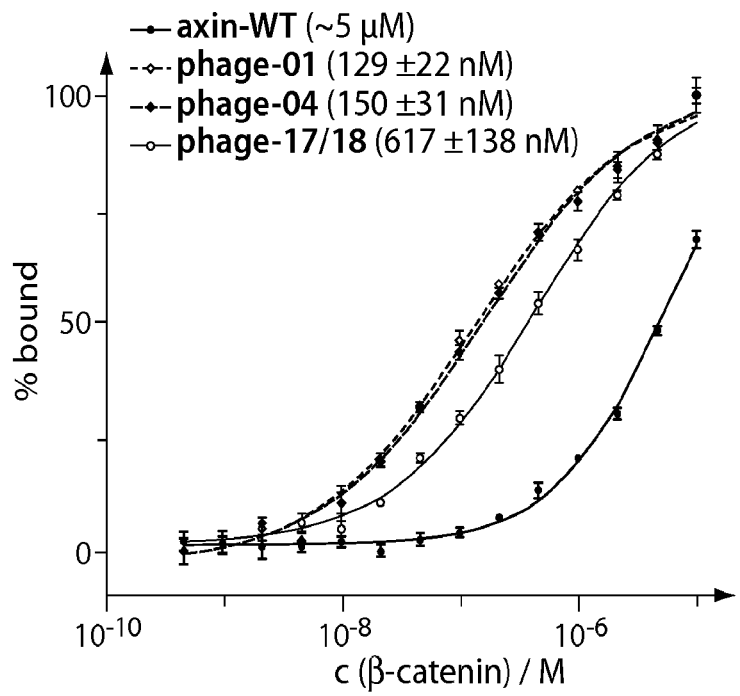
FIG. 7 depicts (a) fluorescently labeled peptide sequences resulting from phage display affinity optimization (entries 1, 4 and 17/18 in FIG. 6*b*); (b) fluorescence polarization assay with fluorescently labeled peptides and N-terminally GST-tagged human β-catenin (with corresponding $K_d$s).

The library members were selected against human β-catenin. Colonies were picked after two and three selection cycles and phage DNA was sequenced to provide the results shown in FIG. 6b. Initially, three of 33 found sequences (entry 1, 4 and 17/18; FIG. 7a) were synthesized and fluorescently labeled. These peptides were tested regarding their affinity to β-catenin and compared to Axin wild type sequence axin-WT. All three peptides showed improved binding to β-catenin ranging from an 8 fold increase for phage-17/18 (617±138 nM) to a 39 fold increase for phage-01 (129±22 nM). These findings indicated a high significance of the variations found in the sequences resulting from phage display.

Figure 8:
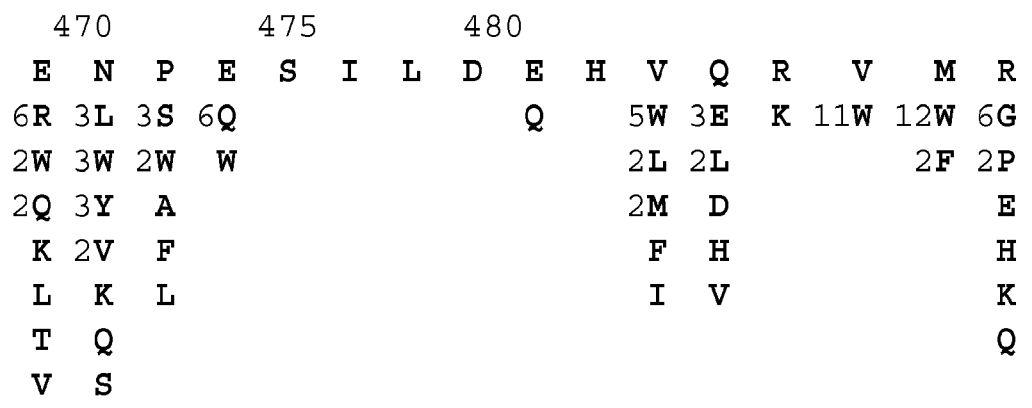

These results were used to modify the sequence of stapled peptide STAX-3. Thereby the focus lay on increasing the affinity to β-catenin as well as rendering the non cell permeable stapled peptide cell permeable. To achieve the second goal the overall charge of the peptide was increased and multiple arginines (R) were incorporated into the sequence as arginine rich peptides are known to be good cell penetrators. [16] FIG. 8 gives a summary of variations found in the 33 sequences resulting from affinity optimization with phage display. The substitutions accumulated in the N- and C-terminal region. There are two areas showing significant incorporation of bulky and hydrophobic residues. One is around N(479) and another at V(482) and M(483). Interestingly, there are also indications that position 469 might allow an E to R and position 472 an E to Q mutation. Both variations would increase the overall charge of the peptide.

FIG. 9a shows a set of STAX-3 derived stapled peptides that bear modifications mainly deduced form the phage display findings. The elimination of N(469) and E(470) in STAX-058 did not affect binding whereas substitution of E(472) and Q(480) by Q and R, respectively (STAX-081) slightly reduced affinity to β-catenin. The introduction of W for V(482) and M(483), respectively increased binding affinity significantly (STAX-083, 11 fold, α-082, 8 fold). Another two fold increase was observed upon addition of R and W at positions 469 and 470 (STAX-090). Overall, the incorporation of an all-hydrocarbon cross-link in combination with phage display-based sequence optimization yielded stapled peptides with more than 600 fold increased binding affinity (ax-090, $K_d$=7.5±1.1 nM) compared to the wild type sequence (ax-WT, $K_d$~5 µM).

Besides its affinity to β-catenin it is cell permeability that impacts the capability of a peptide to interfere with the intracellular target. Therefore, the ability to penetrate cells was tested by monitoring fluorescence of the fluorescein(FITC)-labeled peptides. Negatively charged peptides (FIG. 9a) did not penetrate cells. For positively charged peptides STAX-082 and STAX-083 cell permeability was observed that increased further for STAX-090. FIG. 9b shows confocal pictures of SW480 cells after treatment with 10 µM peptide. The green fluorescent cells indicate the good permeability of peptide STAX-090.

The cell penetrating stapled peptides were tested for their effects on transcriptional activity using an established reporter gene assay. In this dual-luciferase assay firefly luciferase is transcriptionally regulated by constitutively activated Wnt signaling. The firefly signal is normalized to the *Renilla* luciferase control. Treatment with STAX-090 and STAX-147, respectively resulted in repression of luciferase activity (FIG. 10b). At 15 µM STAX-147 the signal is almost completely repressed. Reporter gene expression showed dose dependence upon treatment with STAX-147, with an $IC_{50}$ of about 10 µM (FIG. 10c). Peptide STAX-160 having an altered sequence that results in reduced affinity to β-catenin ($K_d$~9 µM) did not show activity in this reporter gene assay.

Figures 11A, 11B:
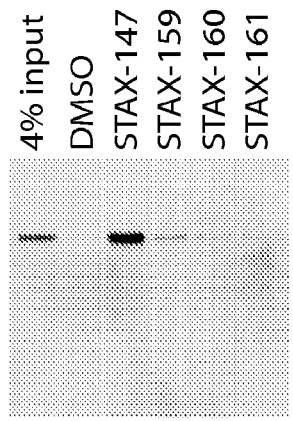
FIG. 11 depicts (a) biotinylated stapled peptides with $K_d$ of the corresponding FITC-labeled analog (blue boxes mark mutations meant to disrupt binding to (β-catenin); (b) pull-down assay with biotinylated STAX-147 and STAX-159-161 in DLD1 lysates. Bound protein fractions were probed with β-catenin specific antibody.

Binding of STAX-147 to endogenous β-catenin was determined by performing pull-down assays in DLD1 cellular lysates. Biotinylated stapled peptides STAX-147 and STAX-159 to STAX-161 (FIG. 11a) were synthesized. Control peptides STAX-159, STAX-160 and STAX-161 were modified (indicated by blue boxes) in order to have reduced affinity to β-catenin. Binding affinities were determined for FITC-labeled analogs and prove a decreasing affinity to β-catenin with an increasing number of modifications. In the pull down assay, cellular lysate was incubated with biotinylated peptides and subsequently treated with streptavidin conjugated beads to immobilize the peptides. For STAX-147 western blots probing with β-catenin specific antibodies showed pull down of β-catenin thereby indicating the formation an STAX- 147/13-catenin complex. Treatment with control peptides STAX-159, STAX-160 and STAX-161 resulted in only small signals for β-catenin.

Figure 12:
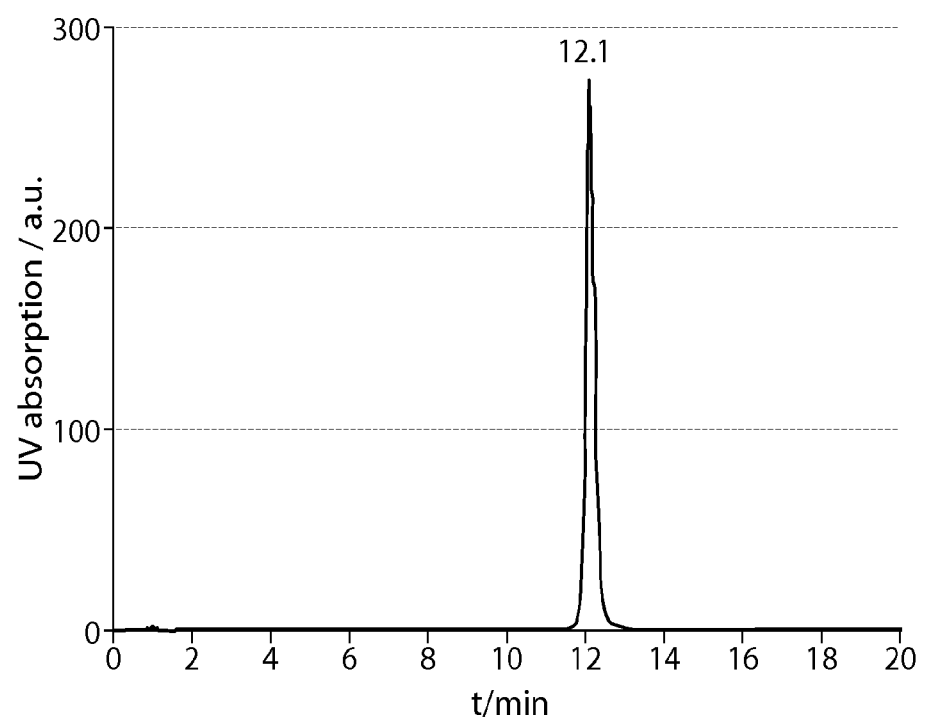
FIG. 12 depicts a UV absorption graph characterizing FITC-PEG1-STAX-147.
Figure 13:
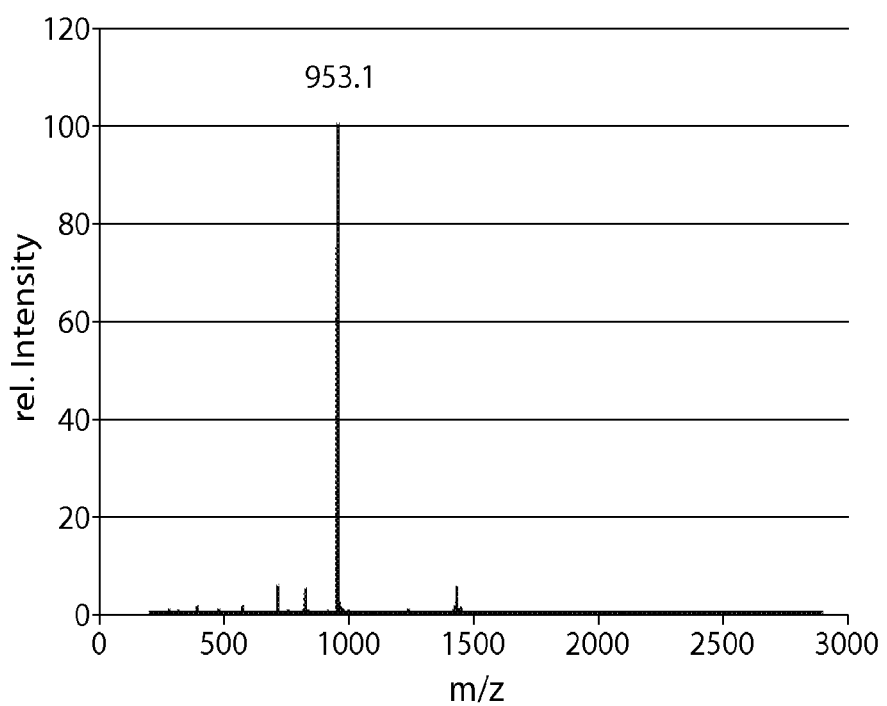
FIG. 13 depicts a relative intensity graph characterizing FITC-PEG1-STAX-147.

FIGS. 12 and 13 show a characterization of FITC-PEG1-STAX-147, with an HPLC gradient of 10-70% CH3CN in 20 min (@ 280 nm). MS: ESI (HPLC/MS) calculated: C135 H194 N40 O28 S; MW: 2857.3008; Exact Mass: 2855.4701; multiply charged: [M+4H]4+:715.33; [M+3H]3+:953.44; [M+2H]2+: 1429.66; [M+1H] 1+:2858.31.

FIG. 14 is a drawing of the structure of STAX-147 and STAX-149.

References

[1] R. T. Moon, A. D. Kohn, G. V. De Ferrari, A. Kaykas, *Nat. Rev. Genet.* 2004, 5, 689-699.

[2] H. Clevers, *Cell* 2006, 127, 469-480.

[3] C. Y. Logan, R. Nusse, *Annu. Rev. Cell Dev. Biol.* 2004, 20, 781-810.

[4] B. Z. Chen, M. E. Dodge, W. Tang, J. M. Lu, Z. Q. Ma, C. W. Fan, S. G. Wei, W. N. Hao, J. Kilgore, N. S. Williams, M. G. Roth, J. F. Amatruda, C. Chen, L. Lum, *Nat. Chem. Biol.* 2009, 5, 100-107.

[5] S. M. A. Huang, Y. M. Mishina, S. M. Liu, A. Cheung, F. Stegmeier, G. A. Michaud, O. Charlat, E. Wiellette, Y. Zhang, S. Wiessner, M. Hild, X. Y. Shi, C. J. Wilson, C. Mickanin, V. Myer, A. Fazal, R. Tomlinson, F. Serluca, W. L. Shao, H. Cheng, M. Shultz, C. Rau, M. Schirle, J. Schlegl, S. Ghidelli, S. Fawell, C. Lu, D. Curtis, M. W. Kirschner, C. Lengauer, P. M. Finan, J. A. Tallarico, T. Bouwmeester, J. A. Porter, A. Bauer, F. Cong, *Nature* 2009, 461, 614-620.

[6] C. W. Xi, M. Balberg, S. A. Boppart, L. Raskin, *Appl. Environ. Microbiol.* 2003, 69, 5673-5678.

[7] H. E. Blackwell, R. H. Grubbs, *Angew. Chem.-Int. Edit.* 1998, 37, 3281-3284.

[8] C. E. Schafineister, J. Po, G. L. Verdine, *J. Am. Chem. Soc.* 2000, 122, 5891-5892.

[9] F. Bernal, A. F. Tyler, S. J. Korsmeyer, L. D. Walensky, G. L. Verdine, *J. Am. Chem. Soc.* 2007, 129, 2456-2457.

[10] L. D. Walensky, A. L. Kung, I. Escher, T. J. Malia, S. Barbuto, R. D. Wright, G. Wagner, G. L. Verdine, S. J. Korsmeyer, *Science* 2004, 305, 1466-1470.

[11] L. D. Walensky, K. Pitter, J. Morash, K. J. Oh, S. Barbuto, J. Fisher, E. Smith, G. L.

Verdine, S. J. Korsmeyer, *Mol. Cell.* 2006, 24, 199-210.

[12] R. E. Moellering, M. Cornejo, T. N. Davis, C. Del Bianco, J. C. Aster, S. C. Blacklow, A., L. Kung, D. G. Gilliland, G. L. Verdine, J. E. Bradner, *Nature* 2009, 462, 182-188.

[13] E. Gavathiotis, M. Suzuki, M. L. Davis, K. Pitter, G. H. Bird, S. G. Katz, H. C. Tu, H. Kim, E. H. Y. Cheng, N. Tjandra, L. D. Walensky, *Nature* 2008, 455, 1076-U1076.

[14] J. Sampietro, C. L. Dahlberg, U.S. Cho, T. R. Hinds, D. Kimelman, W. Q. Xu, *Mol. Cell.* 2006, 24, 293-300.

[15] Y. Xing, W. K. Clements, D. Kimelman, W. Q. Xu, *Genes Dev.* 2003, 17, 2753-2764.

[16] E. A. Goun, T. H. Pillow, L. R. Jones, J. B. Rothbard, P. A. Wender, *Chembiochem* 2006, 7, 1497-1515.

Equivalents and Scope

Those skilled in the art will recognize or be able to ascertain using no more than routine experimentation many equivalents to the specific embodiments described herein. The scope of the present invention is not intended to be limited to the above Description, but rather is as set forth in the appended claims.

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process. Furthermore, it is to be understood that the invention encompasses all variations, combinations, and permutations in which one or more limitations, elements, clauses, descriptive terms, etc., from one or more of the listed claims is introduced into another claim. For example, any claim that is dependent on another claim can be modified to include one or more limitations found in any other claim that is dependent on the same base claim. Furthermore, where the claims recite a composition, it is to be understood that methods of using the composition for any of the purposes disclosed herein are included, and methods of making the composition according to any of the methods of making disclosed herein or other methods known in the art are included, unless otherwise indicated or unless it would be evident to one of ordinary skill in the art that a contradiction or inconsistency would arise.

Where elements are presented as lists, e.g., in Markush group format, it is to be understood that each subgroup of the elements is also disclosed, and any element(s) can be removed from the group. It should it be understood that, in general, where the invention, or aspects of the invention, is/are referred to as comprising particular elements, features, etc., certain embodiments of the invention or aspects of the invention consist, or consist essentially of, such elements, features, etc. For purposes of simplicity those embodiments have not been specifically set forth in haec verba herein. It is also noted that the term "comprising" is intended to be open and permits the inclusion of additional elements or steps.

Where ranges are given, endpoints are included. Furthermore, it is to be understood that unless otherwise indicated or otherwise evident from the context and understanding of one of ordinary skill in the art, values that are expressed as ranges can assume any specific value or subrange within the stated ranges in different embodiments of the invention, to the tenth of the unit of the lower limit of the range, unless the context clearly dictates otherwise.

In addition, it is to be understood that any particular embodiment of the present invention that falls within the prior art may be explicitly excluded from any one or more of the claims. Since such embodiments are deemed to be known to one of ordinary skill in the art, they may be excluded even if the exclusion is not set forth explicitly herein. Any particular embodiment of the compositions of the invention can be excluded from any one or more claims, for any reason, whether or not related to the existence of prior art.

What is claimed is:

1. A β-catenin binding polypeptide comprising an α-helical segment, wherein the polypeptide comprises the amino acid sequence:

$X_1X_2X_3XL_4X_5Y_1X_6X_7X_8Y_2X_9X_{10}X_{11}A_{12}X_{13}X_{14}X_{15}$, wherein $X_1$ is selected from the group consisting of R, K and no amino acid;

$X_2$ is selected from the group consisting of R, K, W and no amino acid;

$X_3$ is selected from the group consisting of W, Y and Q;

$X_4$ is selected from the group consisting of P, S, W, A, F and L;

$X_5$ is selected from the group consisting of E, Q, R and W;

$X_6$ is selected from the group consisting of I and L;

$X_7$ is selected from the group consisting of I and L;

$X_8$ is selected from the group consisting of D and N;

$X_9$ is selected from the group consisting of H and W;

$X_{10}$ is selected from the group consisting of V, W, L, M, F, and I;

$X_{11}$ is selected from the group consisting of Q, E, L, D, H, R, S, and V;

$X_{12}$ is selected from the group consisting of R, S, and K;

$X_{13}$ is selected from the group consisting of V, I, L, W, F and H;

$X_{14}$ is selected from the group consisting of M, Norleucine, I, L, W, F and H;

$X_{15}$ is selected from the group consisting of R, G, P, E, H, K, Q, and no amino acid; and $Y_1$ is selected from the group S, $S^5$, $R^5$, and $Y_2$ is selected from the group E, $S^5$, and $R^5$.

2. The polypeptide of claim 1, wherein the amino acid of $X_1$, $X_2$, $X_{11}$, $X_{12}$, or $X_{15}$ is a positively charged amino acid and/or the amino acid of $X_3$, $X_4$, $X_5$, $X_6$, $X_7$, $X_9$, $X_{10}$, $X_{13}$ or $X_{14}$ is a bulky, hydrophobic amino acid.

3. The polypeptide of claim 1, wherein $Y_1$ and $Y_2$ are $S^5$.

4. The polypeptide of claim 1 comprising a free N-terminus, an acetylated N-terminus, a linker molecule, a labeling moiety, an affinity tag, and/or a targeting moiety.

5. The polypeptide of claim 4, wherein the linker molecule is β-Ala or $PEG_1$.

6. The polypeptide of claim 4, wherein the labeling moiety is FITC.

7. The polypeptide of claim 4, wherein the affinity tag is biotin, FLAG, 6×His, or myc.

8. The polypeptide of claim 4, wherein the targeting moiety is integrin, antibody, or antibody fragment.

9. A pharmaceutical composition comprising the polypeptide of claim 1.

10. A method of treating a cancer that exhibits Wnt-signaling dependent growth in a subject, the method comprising administering to a subject the pharmaceutical composition of claim 9 in an amount sufficient to treat the cancer.

11. A method of modulating Wnt-mediated transcription, the method comprising contacting a cell with the polypeptide of claim 1.

12. A method to inhibit cell proliferation that is dependent on aberrant Wnt-signaling, the method comprising contacting the cell with a polypeptide of claim 1.

13. A β-catenin binding polypeptide comprising an α-helical segment, wherein the polypeptide comprises the amino acid sequence:
$X_1X_2X_3X_4X_5X_6X_7X_8X_9X_{10}X_{11}X_{12}X_{13}X_{14}X_{15}X_{16}$,
wherein
   $X_1$ is selected from the group consisting of R, V, E, Q, T, K, W, and L;
   $X_2$ is selected from the group consisting of W, S, L, N, Y, K, V, and Q;
   $X_3$ is selected from the group consisting of P, L, S, W, A, and F;
   $X_4$ is selected from the group consisting of E, Q, and W;
   $X_5$ is S;
   $X_6$ is I;
   $X_7$ is L;
   $X_8$ is D;
   $X_9$ is selected from the group consisting of E and Q;
   $X_{10}$ is H;
   $X_{11}$ is selected from the group consisting of W, V, F, M, L, and I;
   $X_{12}$ is selected from the group consisting of E, Q, H, D, V, and L;
   $X_{13}$ is selected from the group consisting of R and K;
   $X_{14}$ is selected from the group consisting of V and W;
   $X_{15}$ is selected from the group consisting of M, W, F, and E; and
   $X_{16}$ is selected from the group consisting of R, G, P, E, and Q, with the proviso that the sequence is not the wild-type sequence from Axin.

14. The polypeptide of claim 13, wherein $X_1X_2X_3X_4X_5X_6X_7X_8X_9X_{10}X_{11}X_{12}X_{13}X_{14}X_{15}X_{16}$ is modified to induce and/or stabilize an α-helical conformation.

15. The polypeptide of claim 14, wherein the amino acids positioned at i, i+4 and/or i, i+7 are cross-linked by a hydrocarbon cross-link.

16. The polypeptide of claim 14, wherein the modification is selected from the group consisting of a peptide staple, a lactam cross-link, a disulfide cross-link, α-methylation, N-caps, and a hydrogen bond surrogate.

17. The polypeptide of claim 16, wherein the modification is a peptide staple.

18. The polypeptide of claim 17, wherein the amino acids positioned at i, i+4 and/or i, i+7 are stapled.

19. The polypeptide of claim 13, wherein the sequence is not ENPESILDEHVQRVMR (SEQ ID NO: 1) (amino acids 469-484 of rat axin).

20. A β-catenin binding polypeptide comprising an amino acid sequence of any one of SEQ ID NOs.: 28-58.

21. An isolated polypeptide comprising an α-helical segment, wherein the peptide binds β-catenin and comprises an amino acid sequence selected form the group consisting of the sequences: ENPES$^5$ILDS$^5$HVQRVM (SEQ ID NO:14), PES$^5$ILDS$^5$HVQRVM (SEQ ID NO:15), PES$^5$ILDS$^5$HVRRVMR (SEQ ID NO:16), PQS$^5$ILDS$^5$HVRRVMR (SEQ ID NO:17), PQS$^5$ILDS$^5$HVRRWMR (SEQ ID NO:18), PQS$^5$ILDS$^5$HVRRVWR (SEQ ID NO:19), RWPQS$^5$ILDS$^5$HVRRVWR (SEQ ID NO:20), RRWPQS$^5$ILDS$^5$HVRRVWR (SEQ ID NO:21), RWPRS$^5$ILDS$^5$HVRRVWR (SEQ ID NO:22), RRWPRS$^5$ILDS$^5$HVRRVWR (SEQ ID NO:23), RWPQS$^5$ILDS$^5$HVRRWNleR (SEQ ID NO:24), RWPRS$^5$ILDS$^5$HVRRWNleR (SEQ ID NO:25), RWPQS$^5$ILDS$^5$HVRRRWR (SEQ ID NO:26), RWPRS$^5$ILDS$^5$HVRRRWR (SEQ ID NO:27).

* * * * *

SEQUENCE LISTING

<160> NUMBER OF SEQ ID NOS: 66

<210> SEQ ID NO 1
<211> LENGTH: 16

```
<212> TYPE: PRT
<213> ORGANISM: Rattus norvegicus

<400> SEQUENCE: 1

Glu Asn Pro Glu Ser Ile Leu Asp Glu His Val Gln Arg Val Met Arg
1               5                   10                  15

<210> SEQ ID NO 2
<211> LENGTH: 16
<212> TYPE: PRT
<213> ORGANISM: Homo sapiens

<400> SEQUENCE: 2

Glu Asn Pro Glu Ser Ile Leu Asp Glu His Val Gln Arg Val Leu Arg
1               5                   10                  15

<210> SEQ ID NO 3
<211> LENGTH: 4
<212> TYPE: PRT
<213> ORGANISM: Artificial Sequence
<220> FEATURE:
<223> OTHER INFORMATION: one embodiment of [XAA]s

<400> SEQUENCE: 3

Glu Asn Pro Glu
1

<210> SEQ ID NO 4
<211> LENGTH: 4
<212> TYPE: PRT
<213> ORGANISM: Artificial Sequence
<220> FEATURE:
<223> OTHER INFORMATION: one embodiment of [XAA]s

<400> SEQUENCE: 4

Arg Trp Pro Gln
1

<210> SEQ ID NO 5
<211> LENGTH: 4
<212> TYPE: PRT
<213> ORGANISM: Artificial Sequence
<220> FEATURE:
<223> OTHER INFORMATION: one embodiment of [XAA]s

<400> SEQUENCE: 5

Arg Trp Pro Arg
1

<210> SEQ ID NO 6
<211> LENGTH: 5
<212> TYPE: PRT
<213> ORGANISM: Artificial Sequence
<220> FEATURE:
<223> OTHER INFORMATION: one embodiment of [XAA]s

<400> SEQUENCE: 6

Arg Arg Trp Pro Arg
1               5

<210> SEQ ID NO 7
<211> LENGTH: 3
<212> TYPE: PRT
<213> ORGANISM: Artificial Sequence
<220> FEATURE:
<223> OTHER INFORMATION: one embodiment of [XAA]z
```

```
<400> SEQUENCE: 7

Ile Leu Asp
1

<210> SEQ ID NO 8
<211> LENGTH: 6
<212> TYPE: PRT
<213> ORGANISM: Artificial Sequence
<220> FEATURE:
<223> OTHER INFORMATION: one embodiment of [XAA]t

<400> SEQUENCE: 8

His Val Gln Arg Val Met
1               5

<210> SEQ ID NO 9
<211> LENGTH: 7
<212> TYPE: PRT
<213> ORGANISM: Artificial Sequence
<220> FEATURE:
<223> OTHER INFORMATION: one embodiment of [XAA]t

<400> SEQUENCE: 9

His Val Arg Arg Val Met Arg
1               5

<210> SEQ ID NO 10
<211> LENGTH: 7
<212> TYPE: PRT
<213> ORGANISM: Artificial Sequence
<220> FEATURE:
<223> OTHER INFORMATION: one embodiment of [XAA]t

<400> SEQUENCE: 10

His Val Arg Arg Trp Met Arg
1               5

<210> SEQ ID NO 11
<211> LENGTH: 7
<212> TYPE: PRT
<213> ORGANISM: Artificial Sequence
<220> FEATURE:
<223> OTHER INFORMATION: one embodiment of [XAA]t

<400> SEQUENCE: 11

His Val Arg Arg Val Trp Arg
1               5

<210> SEQ ID NO 12
<211> LENGTH: 7
<212> TYPE: PRT
<213> ORGANISM: Artificial Sequence
<220> FEATURE:
<223> OTHER INFORMATION: one embodiment of [XAA]t

<400> SEQUENCE: 12

His Val Arg Arg Trp Asn Arg
1               5

<210> SEQ ID NO 13
<211> LENGTH: 7
<212> TYPE: PRT
<213> ORGANISM: Artificial Sequence
<220> FEATURE:
<223> OTHER INFORMATION: one embodiment of [XAA]t

<400> SEQUENCE: 13
```

```
His Val Arg Arg Arg Trp Arg
1               5

<210> SEQ ID NO 14
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (9)..(9)
<223> OTHER INFORMATION: (S)-2-amino-2-methylhept-6-enoic acid or a
      stapled derivative thereof

<400> SEQUENCE: 14

Glu Asn Pro Glu Xaa Ile Leu Asp Xaa His Val Gln Arg Val Met
1               5                   10                  15

<210> SEQ ID NO 15
<211> LENGTH: 13
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (7)..(7)
<223> OTHER INFORMATION: (S)-2-amino-2-methylhept-6-enoic acid or a
      stapled derivative thereof

<400> SEQUENCE: 15

Pro Glu Xaa Ile Leu Asp Xaa His Val Gln Arg Val Met
1               5                   10

<210> SEQ ID NO 16
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (7)..(7)
<223> OTHER INFORMATION: (S)-2-amino-2-methylhept-6-enoic acid or a
      stapled derivative thereof

<400> SEQUENCE: 16

Pro Glu Xaa Ile Leu Asp Xaa His Val Arg Arg Val Met Arg
1               5                   10

<210> SEQ ID NO 17
<211> LENGTH: 14
<212> TYPE: PRT
<213> ORGANISM: Artificial Sequence
<220> FEATURE:
```

```
<223> OTHER INFORMATION: synthetic peptide
<220> FEATURE:
<221> NAME/KEY: MISC_FEATURE
<222> LOCATION: (3)..(3)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (7)..(7)
<223> OTHER INFORMATION: (S)-2-amino-2-methylhept-6-enoic acid or a
      stapled derivative thereof

<400> SEQUENCE: 17

Pro Gln Xaa Ile Leu Asp Xaa His Val Arg Arg Val Met Arg
1               5                   10

<210> SEQ ID NO 18
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (7)..(7)
<223> OTHER INFORMATION: (S)-2-amino-2-methylhept-6-enoic acid or a
      stapled derivative thereof

<400> SEQUENCE: 18

Pro Gln Xaa Ile Leu Asp Xaa His Val Arg Arg Trp Met Arg
1               5                   10

<210> SEQ ID NO 19
<211> LENGTH: 14
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (3)..(3)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (7)..(7)
<223> OTHER INFORMATION: (S)-2-amino-2-methylhept-6-enoic acid or a
      stapled derivative thereof

<400> SEQUENCE: 19

Pro Gln Xaa Ile Leu Asp Xaa His Val Arg Arg Val Trp Arg
1               5                   10

<210> SEQ ID NO 20
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (9)..(9)
<223> OTHER INFORMATION: (S)-2-amino-2-methylhept-6-enoic acid or a
``` stapled derivative thereof

<400> SEQUENCE: 20

Arg Trp Pro Gln Xaa Ile Leu Asp Xaa His Val Arg Arg Val Trp Arg
1               5                   10                  15

<210> SEQ ID NO 21
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (6)..(6)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (10)..(10)
<223> OTHER INFORMATION: (S)-2-amino-2-methylhept-6-enoic acid or a
      stapled derivative thereof

<400> SEQUENCE: 21

Arg Arg Trp Pro Gln Xaa Ile Leu Asp Xaa His Val Arg Arg Val Trp
1               5                   10                  15

Arg

<210> SEQ ID NO 22
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (9)..(9)
<223> OTHER INFORMATION: (S)-2-amino-2-methylhept-6-enoic acid or a
      stapled derivative thereof

<400> SEQUENCE: 22

Arg Trp Pro Arg Xaa Ile Leu Asp Xaa His Val Arg Arg Val Trp Arg
1               5                   10                  15

<210> SEQ ID NO 23
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (6)..(6)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (10)..(10)
<223> OTHER INFORMATION: (S)-2-amino-2-methylhept-6-enoic acid or a
      stapled derivative thereof

<400> SEQUENCE: 23

Arg Arg Trp Pro Arg Xaa Ile Leu Asp Xaa His Val Arg Arg Val Trp
1               5                   10                  15

Arg

```
<210> SEQ ID NO 24
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (9)..(9)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (15)..(15)
<223> OTHER INFORMATION: norleucine

<400> SEQUENCE: 24

Arg Trp Pro Gln Xaa Ile Leu Asp Xaa His Val Arg Arg Trp Xaa Arg
1               5                   10                  15

<210> SEQ ID NO 25
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (9)..(9)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (15)..(15)
<223> OTHER INFORMATION: norleucine

<400> SEQUENCE: 25

Arg Trp Pro Arg Xaa Ile Leu Asp Xaa His Val Arg Arg Trp Xaa Arg
1               5                   10                  15

<210> SEQ ID NO 26
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (9)..(9)
<223> OTHER INFORMATION: (S)-2-amino-2-methylhept-6-enoic acid or a
      stapled derivative thereof

<400> SEQUENCE: 26

Arg Trp Pro Gln Xaa Ile Leu Asp Xaa His Val Arg Arg Arg Trp Arg
1               5                   10                  15
```

```
<210> SEQ ID NO 27
<211> LENGTH: 16
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (9)..(9)
<223> OTHER INFORMATION: (S)-2-amino-2-methylhept-6-enoic acid or a
      stapled derivative thereof

<400> SEQUENCE: 27

Arg Trp Pro Arg Xaa Ile Leu Asp Xaa His Val Arg Arg Arg Trp Arg
1               5                   10                  15

<210> SEQ ID NO 28
<211> LENGTH: 16
<212> TYPE: PRT
<213> ORGANISM: Artificial Sequence
<220> FEATURE:
<223> OTHER INFORMATION: phage peptide

<400> SEQUENCE: 28

Arg Trp Pro Glu Ser Ile Leu Asp Glu His Trp Glu Arg Val Met Arg
1               5                   10                  15

<210> SEQ ID NO 29
<211> LENGTH: 16
<212> TYPE: PRT
<213> ORGANISM: Artificial Sequence
<220> FEATURE:
<223> OTHER INFORMATION: phage peptide

<400> SEQUENCE: 29

Val Ser Pro Glu Ser Ile Leu Asp Glu His Val Gln Arg Val Trp Gly
1               5                   10                  15

<210> SEQ ID NO 30
<211> LENGTH: 16
<212> TYPE: PRT
<213> ORGANISM: Artificial Sequence
<220> FEATURE:
<223> OTHER INFORMATION: phage peptide

<400> SEQUENCE: 30

Glu Trp Pro Glu Ser Ile Leu Asp Glu His Trp His Arg Val Met Arg
1               5                   10                  15

<210> SEQ ID NO 31
<211> LENGTH: 16
<212> TYPE: PRT
<213> ORGANISM: Artificial Sequence
<220> FEATURE:
<223> OTHER INFORMATION: phage peptide

<400> SEQUENCE: 31

Arg Leu Pro Glu Ser Ile Leu Asp Glu His Val Gln Arg Val Trp Pro
1               5                   10                  15

<210> SEQ ID NO 32
<211> LENGTH: 16
<212> TYPE: PRT
<213> ORGANISM: Artificial Sequence
```

<220> FEATURE:
<223> OTHER INFORMATION: phage peptide

<400> SEQUENCE: 32

Glu Asn Leu Gln Ser Ile Leu Asp Glu His Val Gln Arg Trp Met Arg
1               5                   10                  15

<210> SEQ ID NO 33
<211> LENGTH: 16
<212> TYPE: PRT
<213> ORGANISM: Artificial Sequence
<220> FEATURE:
<223> OTHER INFORMATION: phage peptide

<400> SEQUENCE: 33

Glu Asn Pro Glu Ser Ile Leu Asp Glu His Phe Asp Lys Trp Met Arg
1               5                   10                  15

<210> SEQ ID NO 34
<211> LENGTH: 16
<212> TYPE: PRT
<213> ORGANISM: Artificial Sequence
<220> FEATURE:
<223> OTHER INFORMATION: phage peptide

<400> SEQUENCE: 34

Glu Asn Pro Glu Ser Ile Leu Asp Gln His Trp Val Arg Trp Met Arg
1               5                   10                  15

<210> SEQ ID NO 35
<211> LENGTH: 16
<212> TYPE: PRT
<213> ORGANISM: Artificial Sequence
<220> FEATURE:
<223> OTHER INFORMATION: phage peptide

<400> SEQUENCE: 35

Glu Asn Ser Trp Ser Ile Leu Asp Glu His Val Gln Arg Val Trp Gly
1               5                   10                  15

<210> SEQ ID NO 36
<211> LENGTH: 16
<212> TYPE: PRT
<213> ORGANISM: Artificial Sequence
<220> FEATURE:
<223> OTHER INFORMATION: phage peptide

<400> SEQUENCE: 36

Arg Tyr Pro Glu Ser Ile Leu Asp Glu His Val Gln Arg Trp Met Arg
1               5                   10                  15

<210> SEQ ID NO 37
<211> LENGTH: 16
<212> TYPE: PRT
<213> ORGANISM: Artificial Sequence
<220> FEATURE:
<223> OTHER INFORMATION: phage peptide

<400> SEQUENCE: 37

Gln Lys Pro Glu Ser Ile Leu Asp Glu His Val Gln Arg Val Trp Pro
1               5                   10                  15

<210> SEQ ID NO 38
<211> LENGTH: 16
<212> TYPE: PRT
<213> ORGANISM: Artificial Sequence
<220> FEATURE:

```
<223> OTHER INFORMATION: phage peptide

<400> SEQUENCE: 38

Thr Trp Pro Glu Ser Ile Leu Asp Glu His Trp Glu Arg Val Met Arg
1               5                   10                  15

<210> SEQ ID NO 39
<211> LENGTH: 16
<212> TYPE: PRT
<213> ORGANISM: Artificial Sequence
<220> FEATURE:
<223> OTHER INFORMATION: phage peptide

<400> SEQUENCE: 39

Glu Asn Trp Gln Ser Ile Leu Asp Glu His Met Gln Arg Val Phe Arg
1               5                   10                  15

<210> SEQ ID NO 40
<211> LENGTH: 16
<212> TYPE: PRT
<213> ORGANISM: Artificial Sequence
<220> FEATURE:
<223> OTHER INFORMATION: phage peptide

<400> SEQUENCE: 40

Arg Leu Pro Glu Ser Ile Leu Asp Glu His Val Gln Arg Trp Met Arg
1               5                   10                  15

<210> SEQ ID NO 41
<211> LENGTH: 16
<212> TYPE: PRT
<213> ORGANISM: Artificial Sequence
<220> FEATURE:
<223> OTHER INFORMATION: phage peptide

<400> SEQUENCE: 41

Gln Val Pro Glu Ser Ile Leu Asp Glu His Val Gln Arg Val Trp Gly
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: phage peptide

<400> SEQUENCE: 42

Glu Asn Pro Glu Ser Ile Leu Asp Glu His Val Gln Arg Trp Met Arg
1               5                   10                  15

<210> SEQ ID NO 43
<211> LENGTH: 16
<212> TYPE: PRT
<213> ORGANISM: Artificial Sequence
<220> FEATURE:
<223> OTHER INFORMATION: phage peptide

<400> SEQUENCE: 43

Glu Asn Pro Glu Ser Ile Leu Asp Glu His Val Gln Arg Trp Met Arg
1               5                   10                  15

<210> SEQ ID NO 44
<211> LENGTH: 16
<212> TYPE: PRT
<213> ORGANISM: Artificial Sequence
<220> FEATURE:
<223> OTHER INFORMATION: phage peptide
```

```
<400> SEQUENCE: 44

Glu Asn Ser Gln Ser Ile Leu Asp Glu His Val Gln Arg Val Trp Gly
1               5                   10                  15

<210> SEQ ID NO 45
<211> LENGTH: 16
<212> TYPE: PRT
<213> ORGANISM: Artificial Sequence
<220> FEATURE:
<223> OTHER INFORMATION: phage peptide

<400> SEQUENCE: 45

Glu Asn Trp Gln Ser Ile Leu Asp Glu His Val Gln Arg Val Trp Arg
1               5                   10                  15

<210> SEQ ID NO 46
<211> LENGTH: 16
<212> TYPE: PRT
<213> ORGANISM: Artificial Sequence
<220> FEATURE:
<223> OTHER INFORMATION: phage peptide

<400> SEQUENCE: 46

Arg Tyr Pro Glu Ser Ile Leu Asp Glu His Val Gln Arg Trp Met Arg
1               5                   10                  15

<210> SEQ ID NO 47
<211> LENGTH: 16
<212> TYPE: PRT
<213> ORGANISM: Artificial Sequence
<220> FEATURE:
<223> OTHER INFORMATION: phage peptide

<400> SEQUENCE: 47

Lys Asn Pro Glu Ser Ile Leu Asp Glu His Val Gln Arg Trp Met Arg
1               5                   10                  15

<210> SEQ ID NO 48
<211> LENGTH: 16
<212> TYPE: PRT
<213> ORGANISM: Artificial Sequence
<220> FEATURE:
<223> OTHER INFORMATION: phage peptide

<400> SEQUENCE: 48

Glu Asn Pro Glu Ser Ile Leu Asp Glu His Trp Glu Arg Val Met Arg
1               5                   10                  15

<210> SEQ ID NO 49
<211> LENGTH: 16
<212> TYPE: PRT
<213> ORGANISM: Artificial Sequence
<220> FEATURE:
<223> OTHER INFORMATION: phage peptide

<400> SEQUENCE: 49

Glu Asn Ala Gln Ser Ile Leu Asp Glu His Val Gln Arg Trp Met Arg
1               5                   10                  15

<210> SEQ ID NO 50
<211> LENGTH: 16
<212> TYPE: PRT
<213> ORGANISM: Artificial Sequence
<220> FEATURE:
<223> OTHER INFORMATION: phage peptide
```

```
<400> SEQUENCE: 50

Glu Asn Pro Glu Ser Ile Leu Asp Glu His Met Gln Arg Val Phe Glu
1               5                   10                  15

<210> SEQ ID NO 51
<211> LENGTH: 16
<212> TYPE: PRT
<213> ORGANISM: Artificial Sequence
<220> FEATURE:
<223> OTHER INFORMATION: phage peptide

<400> SEQUENCE: 51

Glu Asn Ser Glu Ser Ile Leu Asp Glu His Val Gln Arg Val Trp Gly
1               5                   10                  15

<210> SEQ ID NO 52
<211> LENGTH: 16
<212> TYPE: PRT
<213> ORGANISM: Artificial Sequence
<220> FEATURE:
<223> OTHER INFORMATION: phage peptide

<400> SEQUENCE: 52

Glu Asn Pro Glu Ser Ile Leu Asp Glu His Leu Gln Arg Val Trp Gln
1               5                   10                  15

<210> SEQ ID NO 53
<211> LENGTH: 16
<212> TYPE: PRT
<213> ORGANISM: Artificial Sequence
<220> FEATURE:
<223> OTHER INFORMATION: phage peptide

<400> SEQUENCE: 53

Glu Asn Phe Gln Ser Ile Leu Asp Glu His Val Gln Arg Trp Met Arg
1               5                   10                  15

<210> SEQ ID NO 54
<211> LENGTH: 16
<212> TYPE: PRT
<213> ORGANISM: Artificial Sequence
<220> FEATURE:
<223> OTHER INFORMATION: phage peptide

<400> SEQUENCE: 54

Arg Leu Pro Glu Ser Ile Leu Asp Glu His Val Gln Arg Val Trp Arg
1               5                   10                  15

<210> SEQ ID NO 55
<211> LENGTH: 16
<212> TYPE: PRT
<213> ORGANISM: Artificial Sequence
<220> FEATURE:
<223> OTHER INFORMATION: phage peptide

<400> SEQUENCE: 55

Trp Tyr Pro Glu Ser Ile Leu Asp Glu His Leu Leu Arg Val Met Arg
1               5                   10                  15

<210> SEQ ID NO 56
<211> LENGTH: 16
<212> TYPE: PRT
<213> ORGANISM: Artificial Sequence
<220> FEATURE:
<223> OTHER INFORMATION: phage peptide

<400> SEQUENCE: 56
```

```
Glu Asn Pro Glu Ser Ile Leu Asp Glu His Ile Leu Arg Val Glu Lys
1               5                   10                  15

<210> SEQ ID NO 57
<211> LENGTH: 16
<212> TYPE: PRT
<213> ORGANISM: Artificial Sequence
<220> FEATURE:
<223> OTHER INFORMATION: phage peptide

<400> SEQUENCE: 57

Trp Val Pro Glu Ser Ile Leu Asp Glu His Val Gln Arg Val Trp Gly
1               5                   10                  15

<210> SEQ ID NO 58
<211> LENGTH: 16
<212> TYPE: PRT
<213> ORGANISM: Artificial Sequence
<220> FEATURE:
<223> OTHER INFORMATION: phage peptide

<400> SEQUENCE: 58

Leu Gln Pro Glu Ser Ile Leu Asp Glu His Val Gln Arg Val Trp His
1               5                   10                  15

<210> SEQ ID NO 59
<211> LENGTH: 28
<212> TYPE: PRT
<213> ORGANISM: Artificial Sequence
<220> FEATURE:
<223> OTHER INFORMATION: TCF4* NP_110383: 16-50
<220> FEATURE:
<221> NAME/KEY: MISC_FEATURE
<222> LOCATION: (14)..(14)
<223> OTHER INFORMATION: beta-alanine
<220> FEATURE:
<221> NAME/KEY: MISC_FEATURE
<222> LOCATION: (15)..(15)
<223> OTHER INFORMATION: beta-alanine

<400> SEQUENCE: 59

Asp Glu Leu Ile Ser Phe Lys Asp Glu Gly Glu Gln Glu Xaa Xaa Glu
1               5                   10                  15

Arg Asp Leu Ala Asp Val Lys Ser Ser Leu Val Asn
            20                  25

<210> SEQ ID NO 60
<211> LENGTH: 15
<212> TYPE: PRT
<213> ORGANISM: Artificial Sequence
<220> FEATURE:
<223> OTHER INFORMATION: Axin NP_077381: 469-483

<400> SEQUENCE: 60

Glu Asn Pro Glu Ser Ile Leu Asp Glu His Val Gln Arg Val Met
1               5                   10                  15

<210> SEQ ID NO 61
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: (R)-2-amino-2-methyldec-9-enoic acid or a
      stapled derivative thereof
```

```
<220> FEATURE:
<221> NAME/KEY: MISC_FEATURE
<222> LOCATION: (12)..(12)
<223> OTHER INFORMATION: (S)-2-amino-2-methylhept-6-enoic acid or a
      stapled derivative thereof

<400> SEQUENCE: 61

Glu Asn Pro Glu Xaa Ile Leu Asp Glu His Val Xaa Arg Val Met
1               5                   10                  15

<210> SEQ ID NO 62
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (9)..(9)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (13)..(13)
<223> OTHER INFORMATION: (S)-2-amino-2-methylhept-6-enoic acid or a
      stapled derivative thereof

<400> SEQUENCE: 62

Glu Asn Pro Glu Ser Ile Leu Asp Xaa His Val Gln Xaa Val Met
1               5                   10                  15

<210> SEQ ID NO 63
<211> LENGTH: 15
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (5)..(5)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (9)..(9)
<223> OTHER INFORMATION: (S)-2-amino-2-methylhept-6-enoic acid or a
      stapled derivative thereof

<400> SEQUENCE: 63

Glu Asn Pro Glu Xaa Ile Leu Asp Xaa His Val Gln Arg Val Met
1               5                   10                  15

<210> SEQ ID NO 64
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (6)..(6)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (10)..(10)
<223> OTHER INFORMATION: (S)-2-amino-2-methylhept-6-enoic acid or a
      stapled derivative thereof

<400> SEQUENCE: 64

Arg Arg Trp Pro Gln Xaa Ile Leu His Xaa Asp Val Arg Arg Val Trp
1               5                   10                  15
```

Arg

<210> SEQ ID NO 65
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (6)..(6)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (10)..(10)
<223> OTHER INFORMATION: (S)-2-amino-2-methylhept-6-enoic acid or a
      stapled derivative thereof

<400> SEQUENCE: 65

Arg Arg Trp Pro Gln Xaa Ile Leu His Xaa Asp Val Arg Arg Val Ala
1               5                   10                  15

Arg

<210> SEQ ID NO 66
<211> LENGTH: 17
<212> TYPE: PRT
<213> ORGANISM: Artificial Sequence
<220> FEATURE:
<223> OTHER INFORMATION: synthetic peptide
<220> FEATURE:
<221> NAME/KEY: MISC_FEATURE
<222> LOCATION: (6)..(6)
<223> OTHER INFORMATION: (S)-2-amino-2-methylhept-6-enoic acid or a
      stapled derivative thereof
<220> FEATURE:
<221> NAME/KEY: MISC_FEATURE
<222> LOCATION: (10)..(10)
<223> OTHER INFORMATION: (S)-2-amino-2-methylhept-6-enoic acid or a
      stapled derivative thereof

<400> SEQUENCE: 66

Arg Arg Ala Pro Gln Xaa Ile Leu His Xaa Asp Val Arg Arg Val Ala
1               5                   10                  15

Arg